(12) United States Patent
Brahmasandra et al.

(10) Patent No.: US 11,254,927 B2
(45) Date of Patent: Feb. 22, 2022

(54) POLYNUCLEOTIDE CAPTURE MATERIALS, AND SYSTEMS USING SAME

(71) Applicant: HANDYLAB, INC., Franklin Lakes, NJ (US)

(72) Inventors: Sundaresh N. Brahmasandra, Ann Arbor, MI (US); Elizabeth Craig, Ypsilanti, MI (US)

(73) Assignee: HANDYLAB, INC., Franklin Lakes, NJ (US)

( * ) Notice: Subject to any disclaimer, the term of this patent is extended or adjusted under 35 U.S.C. 154(b) by 0 days.

(21) Appl. No.: 16/890,752

(22) Filed: Jun. 2, 2020

(65) Prior Publication Data

US 2020/0291388 A1    Sep. 17, 2020

Related U.S. Application Data

(63) Continuation of application No. 16/818,458, filed on Mar. 13, 2020, now Pat. No. 11,060,082, which is a
(Continued)

(51) Int. Cl.
*C12Q 1/6813* (2018.01)
*C08G 83/00* (2006.01)
(Continued)

(52) U.S. Cl.
CPC ........ *C12N 15/1013* (2013.01); *C07C 233/36* (2013.01); *C07H 1/08* (2013.01); *C08G 83/003* (2013.01); *C12Q 1/6813* (2013.01)

(58) Field of Classification Search
CPC ..... C07H 1/08; C12Q 1/6813; C12N 15/1013
See application file for complete search history.

(56) References Cited

U.S. PATENT DOCUMENTS

| D189,404 S | 12/1960 | Nicolle |
|---|---|---|
| 3,050,239 A | 8/1962 | Williams |

(Continued)

FOREIGN PATENT DOCUMENTS

| AU | 1357102 | 3/2002 |
|---|---|---|
| AU | 3557502 | 7/2002 |

(Continued)

OTHER PUBLICATIONS

Devarakonda et al., "The effect of PAMAM dendrimer generation size and surface functional group on the aqueous solubility of nifedipine" International Journal of Pharmaceutics vol. 284 pp. 133-140 (Year: 2004).*

(Continued)

*Primary Examiner* — Eric Olson
(74) *Attorney, Agent, or Firm* — Knobbe, Martens, Olson & Bear, LLP

(57) ABSTRACT

Methods for processing polynucleotide-containing biological samples, and materials for capturing polynucleotide molecules such as RNA and/or DNA from such samples. The RNA and/or DNA is captured by polyamindoamine (PAMAM (Generation 0)) bound to a surface, such as the surface of magnetic particles. The methods and materials have high efficiency of binding RNA and of DNA, and of release, and thereby permit quantitative determinations.

23 Claims, 9 Drawing Sheets

Related U.S. Application Data continuation of application No. 16/158,752, filed on Oct. 12, 2018, now Pat. No. 10,590,410, which is a continuation of application No. 14/976,746, filed on Dec. 21, 2015, now Pat. No. 10,100,302, which is a continuation of application No. 14/262,525, filed on Apr. 25, 2014, now Pat. No. 9,217,143, which is a continuation of application No. 13/692,980, filed on Dec. 3, 2012, now Pat. No. 8,710,211, which is a continuation of application No. 12/172,214, filed on Jul. 11, 2008, now Pat. No. 8,324,372.

(60) Provisional application No. 60/959,437, filed on Jul. 13, 2007.

(51) Int. Cl.
 *C07C 233/36* (2006.01)
 *C12N 15/10* (2006.01)
 *C07H 1/08* (2006.01)

(56) References Cited

U.S. PATENT DOCUMENTS

| | | |
|---|---|---|
| 3,905,772 A | 9/1975 | Hartnett et al. |
| 3,985,649 A | 10/1976 | Eddelman |
| 4,018,089 A | 4/1977 | Dzula et al. |
| 4,018,652 A | 4/1977 | Lanham et al. |
| 4,038,192 A | 7/1977 | Serur |
| 4,055,395 A | 10/1977 | Honkawa et al. |
| D249,706 S | 9/1978 | Adamski |
| 4,139,005 A | 2/1979 | Dickey |
| D252,157 S | 6/1979 | Kronish et al. |
| D252,341 S | 7/1979 | Thomas |
| D254,687 S | 4/1980 | Fadler et al. |
| 4,212,744 A | 7/1980 | Oota |
| D261,033 S | 9/1981 | Armbruster |
| D261,173 S | 10/1981 | Armbruster |
| 4,301,412 A | 11/1981 | Hill et al. |
| 4,439,526 A | 3/1984 | Columbus |
| 4,457,329 A | 7/1984 | Werley et al. |
| 4,466,740 A | 8/1984 | Kano et al. |
| 4,472,357 A | 9/1984 | Levy et al. |
| 4,504,582 A | 3/1985 | Swann |
| 4,522,786 A | 6/1985 | Ebersole |
| D279,817 S | 7/1985 | Chen et al. |
| D282,208 S | 1/1986 | Lowry |
| 4,599,315 A | 7/1986 | Terasaki et al. |
| 4,612,873 A | 9/1986 | Eberle |
| 4,612,959 A | 9/1986 | Costello |
| D288,478 S | 2/1987 | Carlson et al. |
| 4,647,432 A | 3/1987 | Wakatake |
| 4,654,127 A | 3/1987 | Baker et al. |
| 4,673,657 A | 6/1987 | Christian |
| 4,678,752 A | 7/1987 | Thorne et al. |
| 4,683,195 A | 7/1987 | Mullis et al. |
| 4,683,202 A | 7/1987 | Mullis |
| 4,698,302 A | 10/1987 | Whitehead et al. |
| D292,735 S | 11/1987 | Lovborg |
| 4,720,374 A | 1/1988 | Ramachandran |
| 4,724,207 A | 2/1988 | Hou et al. |
| 4,795,698 A | 1/1989 | Owen et al. |
| 4,798,693 A | 1/1989 | Mase et al. |
| 4,800,022 A | 1/1989 | Leonard |
| 4,827,944 A | 5/1989 | Nugent |
| 4,841,786 A | 6/1989 | Schulz |
| D302,294 S | 7/1989 | Hillman |
| 4,855,110 A | 8/1989 | Marker et al. |
| 4,871,779 A | 10/1989 | Killat et al. |
| 4,889,818 A | 12/1989 | Gelfand et al. |
| 4,895,650 A | 1/1990 | Wang |
| 4,902,624 A | 2/1990 | Columbus et al. |
| 4,914,710 A | 4/1990 | Ward et al. |
| 4,919,829 A | 4/1990 | Gates et al. |
| 4,921,809 A | 5/1990 | Schiff et al. |
| 4,935,342 A | 6/1990 | Seligson et al. |
| 4,946,562 A | 8/1990 | Guruswamy |
| 4,948,561 A | 8/1990 | Hinckley et al. |
| 4,949,742 A | 8/1990 | Rando et al. |
| D310,413 S | 9/1990 | Bigler et al. |
| 4,963,498 A | 10/1990 | Hillman |
| 4,965,188 A | 10/1990 | Mullis et al. |
| 4,967,950 A | 11/1990 | Legg et al. |
| D312,692 S | 12/1990 | Bradley |
| 4,978,502 A | 12/1990 | Dole et al. |
| 4,978,622 A | 12/1990 | Mishell et al. |
| 4,989,626 A | 2/1991 | Takagi et al. |
| 4,994,373 A | 2/1991 | Stavrianopoulos et al. |
| 4,997,772 A | 3/1991 | Sutton et al. |
| 5,001,417 A | 3/1991 | Pumphrey et al. |
| 5,004,583 A | 4/1991 | Guruswamy et al. |
| 5,048,554 A | 9/1991 | Kremer |
| 5,053,199 A | 10/1991 | Keiser et al. |
| 5,060,823 A | 10/1991 | Perlman |
| 5,061,336 A | 10/1991 | Soane |
| 5,064,618 A | 11/1991 | Baker et al. |
| 5,071,531 A | 12/1991 | Soane |
| 5,089,233 A | 2/1992 | DeVaney, Jr. et al. |
| 5,091,328 A | 2/1992 | Miller |
| D324,426 S | 3/1992 | Fan et al. |
| 5,096,669 A | 3/1992 | Lauks et al. |
| D325,638 S | 4/1992 | Sloat et al. |
| 5,126,002 A | 6/1992 | Iwata et al. |
| 5,126,022 A | 6/1992 | Soane et al. |
| D328,135 S | 7/1992 | Fan et al. |
| D328,794 S | 8/1992 | Frenkel et al. |
| 5,135,627 A | 8/1992 | Soane |
| 5,135,872 A | 8/1992 | Pouletty et al. |
| 5,147,606 A | 9/1992 | Charlton et al. |
| 5,147,777 A | 9/1992 | Sutton et al. |
| 5,155,166 A | 10/1992 | Danielson et al. |
| 5,169,512 A | 12/1992 | Wiedenmann et al. |
| 5,173,269 A | 12/1992 | Mon et al. |
| D333,522 S | 2/1993 | Gianino |
| 5,186,339 A | 2/1993 | Heissler |
| 5,192,507 A | 3/1993 | Taylor et al. |
| 5,208,163 A | 5/1993 | Charlton et al. |
| 5,217,694 A | 6/1993 | Gibler et al. |
| 5,223,226 A | 6/1993 | Wittmer et al. |
| 5,229,297 A | 7/1993 | Schnipelsky et al. |
| 5,231,015 A | 7/1993 | Cummins et al. |
| D338,275 S | 8/1993 | Fischer et al. |
| 5,234,809 A | 8/1993 | Boom et al. |
| 5,250,263 A | 10/1993 | Manz |
| 5,252,743 A | 10/1993 | Barrett et al. |
| 5,256,376 A | 10/1993 | Callan et al. |
| 5,273,716 A | 12/1993 | Northrup et al. |
| 5,275,787 A | 1/1994 | Yuguchi et al. |
| 5,282,950 A | 2/1994 | Dietze et al. |
| 5,296,375 A | 3/1994 | Kricka et al. |
| 5,304,477 A | 4/1994 | Nagoh et al. |
| 5,304,487 A | 4/1994 | Wilding et al. |
| D347,478 S | 5/1994 | Pinkney |
| 5,311,896 A | 5/1994 | Kaartinen et al. |
| 5,311,996 A | 5/1994 | Duffy et al. |
| 5,316,727 A | 5/1994 | Suzuki et al. |
| 5,327,038 A | 7/1994 | Culp |
| 5,334,499 A | 8/1994 | Burdick et al. |
| 5,338,671 A | 8/1994 | Scalice et al. |
| 5,339,486 A | 8/1994 | Persic, Jr. |
| D351,475 S | 10/1994 | Gerber |
| D351,913 S | 10/1994 | Hieb et al. |
| 5,364,591 A | 11/1994 | Green et al. |
| 5,372,946 A | 12/1994 | Cusak et al. |
| 5,374,395 A | 12/1994 | Robinson |
| 5,384,499 A | 1/1995 | Pedersen et al. |
| 5,389,339 A | 2/1995 | Petschek et al. |
| D356,232 S | 3/1995 | Armstrong et al. |
| 5,397,709 A | 3/1995 | Berndt |
| 5,401,465 A | 3/1995 | Smethers et al. |
| 5,411,708 A | 5/1995 | Moscetta et al. |
| 5,414,245 A | 5/1995 | Hackleman |
| 5,415,839 A | 5/1995 | Zaun et al. |
| 5,416,000 A | 5/1995 | Allen et al. |

(56) References Cited

U.S. PATENT DOCUMENTS

| | | |
|---|---|---|
| 5,422,271 A | 6/1995 | Chen et al. |
| 5,422,284 A | 6/1995 | Lau |
| 5,427,946 A | 6/1995 | Kricka et al. |
| 5,443,791 A | 8/1995 | Cathcart et al. |
| 5,466,574 A | 11/1995 | Liberti et al. |
| 5,474,796 A | 12/1995 | Brennan |
| 5,475,487 A | 12/1995 | Mariella, Jr. et al. |
| D366,116 S | 1/1996 | Biskupski |
| 5,486,335 A | 1/1996 | Wilding et al. |
| 5,494,639 A | 2/1996 | Grzegorzewski |
| 5,498,392 A | 3/1996 | Wilding et al. |
| 5,503,803 A | 4/1996 | Brown |
| 5,516,410 A | 5/1996 | Schneider et al. |
| 5,519,635 A | 5/1996 | Miyake et al. |
| 5,529,677 A | 6/1996 | Schneider et al. |
| 5,559,432 A | 9/1996 | Logue |
| 5,565,171 A | 10/1996 | Dovichi et al. |
| 5,569,364 A | 10/1996 | Hooper et al. |
| 5,578,270 A | 11/1996 | Reichler et al. |
| 5,578,818 A | 11/1996 | Kain et al. |
| 5,579,928 A | 12/1996 | Anukwuem |
| 5,580,523 A | 12/1996 | Bard |
| 5,582,884 A | 12/1996 | Ball et al. |
| 5,582,988 A | 12/1996 | Backus et al. |
| 5,585,069 A | 12/1996 | Zanucchi et al. |
| 5,585,089 A | 12/1996 | Queen et al. |
| 5,585,242 A | 12/1996 | Bouma et al. |
| 5,587,128 A | 12/1996 | Wilding et al. |
| 5,589,136 A | 12/1996 | Northrup et al. |
| 5,593,838 A | 1/1997 | Zanzucchi et al. |
| 5,595,708 A | 1/1997 | Berndt |
| 5,599,432 A | 2/1997 | Manz et al. |
| 5,599,503 A | 2/1997 | Manz et al. |
| 5,599,667 A | 2/1997 | Arnold, Jr. et al. |
| 5,601,727 A | 2/1997 | Bormann et al. |
| 5,603,351 A | 2/1997 | Cherukuri et al. |
| 5,605,662 A | 2/1997 | Heller et al. |
| 5,609,910 A | 3/1997 | Hackleman |
| D378,782 S | 4/1997 | LaBarbera et al. |
| 5,628,890 A | 5/1997 | Carter et al. |
| 5,630,920 A | 5/1997 | Friese et al. |
| 5,631,337 A | 5/1997 | Sassi et al. |
| 5,632,876 A | 5/1997 | Zanzucchi et al. |
| 5,632,957 A | 5/1997 | Heller et al. |
| 5,635,358 A | 6/1997 | Wilding et al. |
| 5,637,469 A | 6/1997 | Wilding et al. |
| 5,639,423 A | 6/1997 | Northrup et al. |
| 5,639,428 A | 6/1997 | Cottingham |
| 5,643,738 A | 7/1997 | Zanzucchi et al. |
| 5,645,801 A | 7/1997 | Bouma et al. |
| 5,646,039 A | 7/1997 | Northrup et al. |
| 5,646,049 A | 7/1997 | Tayi |
| 5,647,994 A | 7/1997 | Tuunanen et al. |
| 5,651,839 A | 7/1997 | Rauf |
| 5,652,141 A | 7/1997 | Henco et al. |
| 5,652,149 A | 7/1997 | Mileaf et al. |
| D382,346 S | 8/1997 | Buhler et al. |
| D382,647 S | 8/1997 | Staples et al. |
| 5,654,141 A | 8/1997 | Mariani et al. |
| 5,658,515 A | 8/1997 | Lee et al. |
| 5,667,976 A | 9/1997 | Van Ness et al. |
| 5,671,303 A | 9/1997 | Shieh et al. |
| 5,674,394 A | 10/1997 | Whitmore |
| 5,674,742 A | 10/1997 | Northrup et al. |
| 5,681,484 A | 10/1997 | Zanzucchi et al. |
| 5,681,529 A | 10/1997 | Taguchi et al. |
| 5,683,657 A | 11/1997 | Mian |
| 5,683,659 A | 11/1997 | Hovatter |
| 5,699,157 A | 12/1997 | Parce et al. |
| 5,700,637 A | 12/1997 | Southern |
| 5,705,813 A | 1/1998 | Apffel et al. |
| 5,721,136 A | 2/1998 | Finney et al. |
| 5,725,831 A | 3/1998 | Reichler et al. |
| 5,726,026 A | 3/1998 | Wilding et al. |
| 5,726,404 A | 3/1998 | Brody |
| 5,726,944 A | 3/1998 | Pelley et al. |
| 5,731,212 A | 3/1998 | Gavin et al. |
| 5,744,366 A | 4/1998 | Kricka et al. |
| 5,746,978 A | 5/1998 | Bienhaus et al. |
| 5,747,666 A | 5/1998 | Willis |
| 5,750,015 A | 5/1998 | Soane et al. |
| 5,755,942 A | 5/1998 | Zanzucchi et al. |
| 5,762,874 A | 6/1998 | Seaton et al. |
| 5,763,262 A | 6/1998 | Wong et al. |
| 5,770,029 A | 6/1998 | Nelson et al. |
| 5,770,388 A | 6/1998 | Vorpahl |
| 5,772,966 A | 6/1998 | Maracas et al. |
| 5,779,868 A | 7/1998 | Parce et al. |
| 5,783,148 A | 7/1998 | Cottingham et al. |
| 5,787,032 A | 7/1998 | Heller et al. |
| 5,788,814 A | 8/1998 | Sun et al. |
| 5,800,600 A | 9/1998 | Lima-Marques et al. |
| 5,800,690 A | 9/1998 | Chow et al. |
| 5,804,436 A | 9/1998 | Okun et al. |
| D399,959 S | 10/1998 | Prokop et al. |
| 5,819,749 A | 10/1998 | Lee et al. |
| 5,827,481 A | 10/1998 | Bente et al. |
| 5,842,106 A | 11/1998 | Thaler et al. |
| 5,842,787 A | 12/1998 | Kopf-Sill et al. |
| 5,846,396 A | 12/1998 | Zanzucchi et al. |
| 5,846,493 A | 12/1998 | Bankier et al. |
| 5,849,208 A | 12/1998 | Hayes et al. |
| 5,849,486 A | 12/1998 | Heller et al. |
| 5,849,489 A | 12/1998 | Heller |
| 5,849,598 A | 12/1998 | Wilson et al. |
| 5,852,495 A | 12/1998 | Parce |
| 5,856,174 A | 1/1999 | Lipshutz et al. |
| 5,858,187 A | 1/1999 | Ramsey et al. |
| 5,858,188 A | 1/1999 | Soane et al. |
| 5,863,502 A | 1/1999 | Southgate et al. |
| 5,863,708 A | 1/1999 | Zanzucchi et al. |
| 5,863,801 A | 1/1999 | Southgate et al. |
| 5,866,345 A | 2/1999 | Wilding et al. |
| 5,869,004 A | 2/1999 | Parce et al. |
| 5,869,244 A | 2/1999 | Martin et al. |
| 5,872,010 A | 2/1999 | Karger et al. |
| 5,872,623 A | 2/1999 | Stabile et al. |
| 5,874,046 A | 2/1999 | Megerle |
| 5,876,675 A | 3/1999 | Kennedy |
| 5,880,071 A | 3/1999 | Parce et al. |
| 5,882,465 A | 3/1999 | McReynolds |
| 5,883,211 A | 3/1999 | Sassi et al. |
| 5,885,432 A | 3/1999 | Hooper et al. |
| 5,885,470 A | 3/1999 | Parce et al. |
| 5,895,762 A | 4/1999 | Greenfield et al. |
| 5,900,130 A | 5/1999 | Benvegnu et al. |
| 5,911,737 A | 6/1999 | Lee et al. |
| 5,912,124 A | 6/1999 | Kumar |
| 5,912,134 A | 6/1999 | Shartle |
| 5,914,229 A | 6/1999 | Loewy |
| 5,916,522 A | 6/1999 | Boyd et al. |
| 5,916,776 A | 6/1999 | Kumar |
| 5,919,646 A | 7/1999 | Okun et al. |
| 5,919,711 A | 7/1999 | Boyd et al. |
| 5,922,591 A | 7/1999 | Anderson et al. |
| 5,927,547 A | 7/1999 | Papen et al. |
| 5,928,161 A | 7/1999 | Krulevitch et al. |
| 5,928,880 A | 7/1999 | Wilding et al. |
| 5,929,208 A | 7/1999 | Heller et al. |
| D413,391 S | 8/1999 | Lapeus et al. |
| 5,932,799 A | 8/1999 | Moles |
| 5,935,401 A | 8/1999 | Amigo |
| 5,939,291 A | 8/1999 | Loewy et al. |
| 5,939,312 A | 8/1999 | Baier et al. |
| 5,942,443 A | 8/1999 | Parce et al. |
| 5,944,717 A | 8/1999 | Lee et al. |
| D413,677 S | 9/1999 | Dumitrescu et al. |
| D414,271 S | 9/1999 | Mendoza |
| 5,948,227 A | 9/1999 | Dubrow |
| 5,948,363 A | 9/1999 | Gaillard |
| 5,948,673 A | 9/1999 | Cottingham |
| 5,955,028 A | 9/1999 | Chow |
| 5,955,029 A | 9/1999 | Wilding et al. |
| 5,957,579 A | 9/1999 | Kopf-Sill et al. |

(56) References Cited

U.S. PATENT DOCUMENTS

| | | |
|---|---|---|
| 5,958,203 A | 9/1999 | Parce et al. |
| 5,958,349 A | 9/1999 | Petersen et al. |
| 5,958,694 A | 9/1999 | Nikiforov |
| 5,959,221 A | 9/1999 | Boyd et al. |
| 5,959,291 A | 9/1999 | Jensen |
| 5,935,522 A | 10/1999 | Swerdlow et al. |
| 5,964,995 A | 10/1999 | Nikiforov et al. |
| 5,964,997 A | 10/1999 | McBride |
| 5,965,001 A | 10/1999 | Chow et al. |
| 5,965,410 A | 10/1999 | Chow et al. |
| 5,965,886 A | 10/1999 | Sauer et al. |
| 5,968,745 A | 10/1999 | Thorp et al. |
| 5,972,187 A | 10/1999 | Parce et al. |
| 5,973,138 A | 10/1999 | Collis |
| D417,009 S | 11/1999 | Boyd |
| 5,976,336 A | 11/1999 | Dubrow et al. |
| 5,980,704 A | 11/1999 | Cherukuri et al. |
| 5,980,719 A | 11/1999 | Cherukuri et al. |
| 5,981,735 A | 11/1999 | Thatcher et al. |
| 5,985,651 A | 11/1999 | Hunicke-Smith |
| 5,989,402 A | 11/1999 | Chow et al. |
| 5,992,820 A | 11/1999 | Fare et al. |
| 5,993,611 A | 11/1999 | Moroney, III et al. |
| 5,993,750 A | 11/1999 | Ghosh et al. |
| 5,997,708 A | 12/1999 | Craig |
| 6,001,229 A | 12/1999 | Ramsey |
| 6,001,231 A | 12/1999 | Kopf-Sill |
| 6,001,307 A | 12/1999 | Naka et al. |
| 6,004,450 A | 12/1999 | Northrup et al. |
| 6,004,515 A | 12/1999 | Parce et al. |
| 6,007,690 A | 12/1999 | Nelson et al. |
| 6,010,607 A | 1/2000 | Ramsey |
| 6,010,608 A | 1/2000 | Ramsey |
| 6,010,627 A | 1/2000 | Hood, III |
| 6,012,902 A | 1/2000 | Parce |
| D420,747 S | 2/2000 | Dumitrescu et al. |
| D421,130 S | 2/2000 | Cohen et al. |
| 6,024,920 A | 2/2000 | Cunanan |
| D421,653 S | 3/2000 | Purcell |
| 6,033,546 A | 3/2000 | Ramsey |
| 6,033,880 A | 3/2000 | Haff et al. |
| 6,043,080 A | 3/2000 | Lipshutz et al. |
| 6,043,880 A | 3/2000 | Andrews et al. |
| 6,046,056 A | 4/2000 | Parce et al. |
| 6,048,734 A | 4/2000 | Burns et al. |
| 6,054,034 A | 4/2000 | Soane et al. |
| 6,054,277 A | 4/2000 | Furcht et al. |
| 6,056,860 A | 5/2000 | Amigo et al. |
| 6,057,149 A | 5/2000 | Burns et al. |
| 6,062,261 A | 5/2000 | Jacobson et al. |
| 6,063,341 A | 5/2000 | Fassbind et al. |
| 6,063,589 A | 5/2000 | Kellogg et al. |
| 6,068,751 A | 5/2000 | Neukermans |
| 6,068,752 A | 5/2000 | Dubrow et al. |
| 6,071,478 A | 6/2000 | Chow |
| 6,074,725 A | 6/2000 | Kennedy |
| 6,074,827 A | 6/2000 | Nelson et al. |
| D428,497 S | 7/2000 | Lapeus et al. |
| 6,086,740 A | 7/2000 | Kennedy |
| 6,096,509 A | 8/2000 | Okun et al. |
| 6,100,541 A | 8/2000 | Nagle et al. |
| 6,102,897 A | 8/2000 | Lang |
| 6,103,537 A | 8/2000 | Ullman et al. |
| 6,106,685 A | 8/2000 | McBride et al. |
| 6,110,343 A | 8/2000 | Ramsey et al. |
| 6,117,398 A | 9/2000 | Bienhaus et al. |
| 6,123,205 A | 9/2000 | Dumitrescu et al. |
| 6,123,798 A | 9/2000 | Gandhi et al. |
| 6,130,098 A | 10/2000 | Handique et al. |
| 6,132,580 A | 10/2000 | Mathies et al. |
| 6,132,684 A | 10/2000 | Marino |
| 6,133,436 A | 10/2000 | Koster et al. |
| D433,759 S | 11/2000 | Mathis et al. |
| 6,143,250 A | 11/2000 | Tajima |
| 6,143,547 A | 11/2000 | Hsu |
| 6,149,787 A | 11/2000 | Chow et al. |
| 6,149,872 A | 11/2000 | Mack et al. |
| 6,156,199 A | 12/2000 | Zuk, Jr. |
| 6,158,269 A | 12/2000 | Dorenkott et al. |
| 6,167,910 B1 | 1/2001 | Chow |
| 6,168,948 B1 | 1/2001 | Anderson et al. |
| 6,171,850 B1 | 1/2001 | Nagle et al. |
| 6,174,675 B1 | 1/2001 | Chow et al. |
| 6,180,950 B1 | 1/2001 | Olsen |
| D438,311 S | 2/2001 | Yamanishi et al. |
| 6,190,619 B1 | 2/2001 | Kilcoin et al. |
| 6,194,563 B1 | 2/2001 | Cruickshank |
| D438,632 S | 3/2001 | Miller |
| D438,633 S | 3/2001 | Miller |
| D439,673 S | 3/2001 | Brophy et al. |
| 6,197,595 B1 | 3/2001 | Anderson et al. |
| 6,211,989 B1 | 4/2001 | Wulf et al. |
| 6,213,151 B1 | 4/2001 | Jacobson et al. |
| 6,221,600 B1 | 4/2001 | MacLeod et al. |
| 6,228,635 B1 | 5/2001 | Armstrong et al. |
| 6,232,072 B1 | 5/2001 | Fisher |
| 6,235,175 B1 | 5/2001 | Dubrow et al. |
| 6,235,313 B1 | 5/2001 | Mathiowitz et al. |
| 6,235,471 B1 | 5/2001 | Knapp et al. |
| 6,236,456 B1 | 5/2001 | Giebeler et al. |
| 6,236,581 B1 | 5/2001 | Foss et al. |
| 6,238,626 B1 | 5/2001 | Higuchi et al. |
| 6,251,343 B1 | 6/2001 | Dubrow et al. |
| 6,254,826 B1 | 7/2001 | Acosta et al. |
| 6,259,635 B1 | 7/2001 | Khouri et al. |
| 6,261,431 B1 | 7/2001 | Mathies et al. |
| 6,267,858 B1 | 7/2001 | Parce et al. |
| D446,306 S | 8/2001 | Ochi et al. |
| 6,271,021 B1 | 8/2001 | Burns et al. |
| 6,274,089 B1 | 8/2001 | Chow et al. |
| 6,280,967 B1 | 8/2001 | Ransom et al. |
| 6,281,008 B1 | 8/2001 | Komai et al. |
| 6,284,113 B1 | 9/2001 | Bjornson et al. |
| 6,284,470 B1 | 9/2001 | Bitner et al. |
| 6,287,254 B1 | 9/2001 | Dodds |
| 6,287,774 B1 | 9/2001 | Nikiforov |
| 6,291,248 B1 | 9/2001 | Haj-Ahmad |
| 6,294,063 B1 | 9/2001 | Becker et al. |
| 6,300,124 B1 | 10/2001 | Blumenfeld et al. |
| 6,302,134 B1 | 10/2001 | Kellogg et al. |
| 6,302,304 B1 | 10/2001 | Spencer |
| 6,303,343 B1 | 10/2001 | Kopf-Sill |
| 6,306,273 B1 | 10/2001 | Wainright et al. |
| 6,306,590 B1 | 10/2001 | Mehta et al. |
| 6,310,199 B1 | 10/2001 | Smith et al. |
| 6,316,774 B1 | 11/2001 | Giebeler et al. |
| 6,319,469 B1 | 11/2001 | Mian et al. |
| 6,319,474 B1 | 11/2001 | Krulevitch et al. |
| 6,322,683 B1 | 11/2001 | Wolk et al. |
| 6,326,083 B1 | 12/2001 | Yang et al. |
| 6,326,147 B1 | 12/2001 | Oldham et al. |
| 6,326,211 B1 | 12/2001 | Anderson et al. |
| 6,334,980 B1 | 1/2002 | Hayes et al. |
| 6,337,435 B1 | 1/2002 | Chu et al. |
| 6,353,475 B1 | 3/2002 | Jensen et al. |
| 6,358,387 B1 | 3/2002 | Kopf-sill et al. |
| 6,366,924 B1 | 4/2002 | Parce |
| 6,368,561 B1 | 4/2002 | Rutishauser et al. |
| 6,368,871 B1 | 4/2002 | Christel et al. |
| 6,370,206 B1 | 4/2002 | Schenk |
| 6,375,185 B1 | 4/2002 | Lin |
| 6,375,901 B1 | 4/2002 | Robotti et al. |
| 6,379,884 B2 | 4/2002 | Wada et al. |
| 6,379,929 B1 | 4/2002 | Burns et al. |
| 6,379,974 B1 | 4/2002 | Parce et al. |
| 6,382,254 B1 | 5/2002 | Yang et al. |
| 6,391,541 B1 | 5/2002 | Petersen et al. |
| 6,391,623 B1 | 5/2002 | Besemer et al. |
| 6,395,161 B1 | 5/2002 | Schneider et al. |
| 6,398,956 B1 | 6/2002 | Coville et al. |
| 6,399,025 B1 | 6/2002 | Chow |
| 6,399,389 B1 | 6/2002 | Parce et al. |
| 6,399,952 B1 | 6/2002 | Maher et al. |
| 6,401,552 B1 | 6/2002 | Elkins |

(56) References Cited

U.S. PATENT DOCUMENTS

| | | |
|---|---|---|
| 6,403,338 B1 | 6/2002 | Knapp et al. |
| 6,408,878 B2 | 6/2002 | Unger et al. |
| 6,413,401 B1 | 7/2002 | Chow et al. |
| 6,416,642 B1 | 7/2002 | Alajoki et al. |
| 6,420,143 B1 | 7/2002 | Kopf-sill |
| 6,425,972 B1 | 7/2002 | McReynolds |
| D461,906 S | 8/2002 | Pham |
| 6,428,987 B2 | 8/2002 | Franzen |
| 6,430,512 B1 | 8/2002 | Gallagher |
| 6,432,366 B2 | 8/2002 | Ruediger et al. |
| 6,440,725 B1 | 8/2002 | Pourahmadi et al. |
| D463,031 S | 9/2002 | Slomski et al. |
| 6,444,461 B1 | 9/2002 | Knapp et al. |
| 6,447,661 B1 | 9/2002 | Chow et al. |
| 6,447,727 B1 | 9/2002 | Parce et al. |
| 6,448,047 B2 | 9/2002 | Dattagupta et al. |
| 6,448,064 B1 | 9/2002 | Vo-Dinh et al. |
| 6,453,928 B1 | 9/2002 | Kaplan et al. |
| 6,458,259 B1 | 10/2002 | Parce et al. |
| 6,461,570 B2 | 10/2002 | Ishihara et al. |
| 6,465,257 B1 | 10/2002 | Parce et al. |
| 6,468,761 B2 | 10/2002 | Yang et al. |
| 6,472,141 B2 | 10/2002 | Nikiforov |
| D466,219 S | 11/2002 | Wynschenk et al. |
| 6,475,364 B1 | 11/2002 | Dubrow et al. |
| D467,348 S | 12/2002 | McMichael et al. |
| D467,349 S | 12/2002 | Niedbala et al. |
| 6,488,897 B2 | 12/2002 | Dubrow et al. |
| 6,495,104 B1 | 12/2002 | Unno et al. |
| 6,498,497 B1 | 12/2002 | Chow et al. |
| 6,500,323 B1 | 12/2002 | Chow et al. |
| 6,500,390 B1 | 12/2002 | Boulton et al. |
| D468,437 S | 1/2003 | McMenamy et al. |
| 6,506,609 B1 | 1/2003 | Wada et al. |
| 6,509,186 B1 | 1/2003 | Zou et al. |
| 6,509,193 B1 | 1/2003 | Tajima |
| 6,511,853 B1 | 1/2003 | Kopf-sill et al. |
| D470,595 S | 2/2003 | Crisanti et al. |
| 6,515,753 B2 | 2/2003 | Maher |
| 6,517,783 B2 | 2/2003 | Horner et al. |
| 6,520,197 B2 | 2/2003 | Deshmukh et al. |
| 6,521,181 B1 | 2/2003 | Northrup et al. |
| 6,521,188 B1 | 2/2003 | Webster |
| 6,524,456 B1 | 2/2003 | Ramsey et al. |
| 6,524,532 B1 | 2/2003 | Northrup |
| 6,524,790 B1 | 2/2003 | Kopf-sill et al. |
| D472,324 S | 3/2003 | Rumore et al. |
| 6,534,295 B2 | 3/2003 | Tai et al. |
| 6,537,432 B1 | 3/2003 | Schneider et al. |
| 6,537,771 B1 | 3/2003 | Farinas et al. |
| 6,540,896 B1 | 4/2003 | Manz et al. |
| 6,544,734 B1 | 4/2003 | Briscoe et al. |
| 6,547,942 B1 | 4/2003 | Parce et al. |
| 6,555,389 B1 | 4/2003 | Ullman et al. |
| 6,556,923 B2 | 4/2003 | Gallagher et al. |
| D474,279 S | 5/2003 | Mayer et al. |
| D474,280 S | 5/2003 | Niedbala et al. |
| 6,558,916 B2 | 5/2003 | Veerapandian et al. |
| 6,558,945 B1 | 5/2003 | Kao |
| 6,565,815 B1 | 5/2003 | Chang et al. |
| 6,569,607 B2 | 5/2003 | McReynolds |
| 6,572,830 B1 | 6/2003 | Burdon et al. |
| 6,575,188 B2 | 6/2003 | Parunak |
| 6,576,459 B2 | 6/2003 | Miles et al. |
| 6,579,453 B1 | 6/2003 | Bächler et al. |
| 6,589,729 B2 | 7/2003 | Chan et al. |
| 6,592,821 B1 | 7/2003 | Wada et al. |
| 6,597,450 B1 | 7/2003 | Andrews et al. |
| 6,602,474 B1 | 8/2003 | Tajima |
| 6,613,211 B1 | 9/2003 | Mccormick et al. |
| 6,613,512 B1 | 9/2003 | Kopf-sill et al. |
| 6,613,580 B1 | 9/2003 | Chow et al. |
| 6,613,581 B1 | 9/2003 | Wada et al. |
| 6,614,030 B2 | 9/2003 | Maher et al. |
| 6,620,625 B2 | 9/2003 | Wolk et al. |
| 6,623,860 B2 | 9/2003 | Hu et al. |
| 6,627,406 B1 | 9/2003 | Singh et al. |
| D480,814 S | 10/2003 | Lafferty et al. |
| 6,632,655 B1 | 10/2003 | Mehta et al. |
| 6,633,785 B1 | 10/2003 | Kasahara et al. |
| D482,796 S | 11/2003 | Oyama et al. |
| 6,640,981 B2 | 11/2003 | Lafond et al. |
| 6,649,358 B1 | 11/2003 | Parce et al. |
| 6,664,104 B2 | 12/2003 | Pourahmadi et al. |
| 6,669,831 B2 | 12/2003 | Chow et al. |
| 6,670,133 B2 | 12/2003 | Knapp et al. |
| 6,670,153 B2 | 12/2003 | Stern |
| D484,989 S | 1/2004 | Gebrian |
| 6,672,458 B2 | 1/2004 | Hansen et al. |
| 6,681,616 B2 | 1/2004 | Spaid et al. |
| 6,681,788 B2 | 1/2004 | Parce et al. |
| 6,685,813 B2 | 2/2004 | Williams et al. |
| 6,692,700 B2 | 2/2004 | Handique |
| 6,695,009 B2 | 2/2004 | Chien et al. |
| 6,699,713 B2 | 3/2004 | Benett et al. |
| 6,706,519 B1 | 3/2004 | Kellogg et al. |
| 6,720,148 B1 | 4/2004 | Nikiforov |
| 6,730,206 B2 | 5/2004 | Ricco et al. |
| 6,733,645 B1 | 5/2004 | Chow |
| 6,734,401 B2 | 5/2004 | Bedingham et al. |
| 6,737,026 B1 | 5/2004 | Bergh et al. |
| 6,740,518 B1 | 5/2004 | Duong et al. |
| D491,272 S | 6/2004 | Alden et al. |
| D491,273 S | 6/2004 | Biegler et al. |
| D491,276 S | 6/2004 | Langille |
| 6,750,661 B2 | 6/2004 | Brooks et al. |
| 6,752,966 B1 | 6/2004 | Chazan |
| 6,756,019 B1 | 6/2004 | Dubrow et al. |
| 6,762,049 B2 | 7/2004 | Zou et al. |
| 6,764,859 B1 | 7/2004 | Kreuwel et al. |
| 6,766,817 B2 | 7/2004 | da Silva |
| 6,773,567 B1 | 8/2004 | Wolk |
| 6,777,184 B2 | 8/2004 | Nikiforov et al. |
| 6,783,962 B1 | 8/2004 | Olander et al. |
| D495,805 S | 9/2004 | Lea et al. |
| 6,787,015 B2 | 9/2004 | Lackritz et al. |
| 6,787,016 B2 | 9/2004 | Tan et al. |
| 6,787,111 B2 | 9/2004 | Roach et al. |
| 6,790,328 B2 | 9/2004 | Jacobson et al. |
| 6,790,330 B2 | 9/2004 | Gascoyne et al. |
| 6,811,668 B1 | 11/2004 | Berndt et al. |
| 6,818,113 B2 | 11/2004 | Williams et al. |
| 6,819,027 B2 | 11/2004 | Saraf |
| 6,824,663 B1 | 11/2004 | Boone |
| D499,813 S | 12/2004 | Wu |
| D500,142 S | 12/2004 | Crisanti et al. |
| D500,363 S | 12/2004 | Fanning et al. |
| 6,827,831 B1 | 12/2004 | Chow et al. |
| 6,827,906 B1 | 12/2004 | Bjornson et al. |
| 6,838,156 B1 | 1/2005 | Neyer et al. |
| 6,838,680 B2 | 1/2005 | Maher et al. |
| 6,852,287 B2 | 2/2005 | Ganesan |
| 6,858,185 B1 | 2/2005 | Kopf-sill et al. |
| 6,859,698 B2 | 2/2005 | Schmeisser |
| 6,861,035 B2 | 3/2005 | Pham et al. |
| 6,878,540 B2 | 4/2005 | Pourahmadi et al. |
| 6,878,755 B2 | 4/2005 | Singh et al. |
| 6,884,628 B2 | 4/2005 | Hubbell et al. |
| 6,887,693 B2 | 5/2005 | McMillan et al. |
| 6,893,879 B2 | 5/2005 | Petersen et al. |
| 6,900,889 B2 | 5/2005 | Bjornson et al. |
| 6,905,583 B2 | 6/2005 | Wainright et al. |
| 6,905,612 B2 | 6/2005 | Dorian et al. |
| 6,906,797 B1 | 6/2005 | Kao et al. |
| 6,908,594 B1 | 6/2005 | Schaevitz et al. |
| 6,911,183 B1 | 6/2005 | Handique et al. |
| 6,914,137 B2 | 7/2005 | Baker |
| 6,915,679 B2 | 7/2005 | Chien et al. |
| 6,918,404 B2 | 7/2005 | da Silva |
| D508,999 S | 8/2005 | Fanning et al. |
| 6,939,451 B2 | 9/2005 | Zhao et al. |
| 6,940,598 B2 | 9/2005 | Christel et al. |
| 6,942,771 B1 | 9/2005 | Kayyem |
| 6,951,632 B2 | 10/2005 | Unger et al. |

(56) References Cited

U.S. PATENT DOCUMENTS

| | | |
|---|---|---|
| 6,958,392 B2 | 10/2005 | Fomovskaia et al. |
| D512,155 S | 11/2005 | Matsumoto |
| 6,964,747 B2 | 11/2005 | Banerjee et al. |
| 6,977,163 B1 | 12/2005 | Mehta |
| 6,979,424 B2 | 12/2005 | Northrup et al. |
| 6,984,516 B2 | 1/2006 | Briscoe et al. |
| D515,707 S | 2/2006 | Sinohara et al. |
| D516,221 S | 2/2006 | Wohlstadter et al. |
| 7,001,853 B1 | 2/2006 | Brown et al. |
| 7,004,184 B2 | 2/2006 | Handique et al. |
| D517,554 S | 3/2006 | Yanagisawa et al. |
| 7,010,391 B2 | 3/2006 | Handique et al. |
| 7,023,007 B2 | 4/2006 | Gallagher |
| 7,024,281 B1 | 4/2006 | Unno |
| 7,036,667 B2 | 5/2006 | Greenstein et al. |
| 7,037,416 B2 | 5/2006 | Parce et al. |
| 7,038,472 B1 | 5/2006 | Chien |
| 7,039,527 B2 | 5/2006 | Tripathi et al. |
| 7,040,144 B2 | 5/2006 | Spaid et al. |
| 7,049,558 B2 | 5/2006 | Baer et al. |
| D523,153 S | 6/2006 | Akashi et al. |
| 7,055,695 B2 | 6/2006 | Greenstein et al. |
| 7,060,171 B1 | 6/2006 | Nikiforov et al. |
| 7,066,586 B2 | 6/2006 | da Silva |
| 7,069,952 B1 | 7/2006 | McReynolds et al. |
| 7,072,036 B2 | 7/2006 | Jones et al. |
| 7,099,778 B2 | 8/2006 | Chien |
| D528,215 S | 9/2006 | Malmsater |
| 7,101,467 B2 | 9/2006 | Spaid |
| 7,105,304 B1 | 9/2006 | Nikiforov et al. |
| D531,321 S | 10/2006 | Godfrey et al. |
| 7,118,892 B2 | 10/2006 | Ammann et al. |
| 7,118,910 B2 | 10/2006 | Unger et al. |
| 7,122,799 B2 | 10/2006 | Hsieh et al. |
| 7,135,144 B2 | 11/2006 | Christel et al. |
| 7,138,032 B2 | 11/2006 | Gandhi et al. |
| D534,280 S | 12/2006 | Gomm et al. |
| 7,150,814 B1 | 12/2006 | Parce et al. |
| 7,150,999 B1 | 12/2006 | Shuck |
| D535,403 S | 1/2007 | Isozaki et al. |
| 7,160,423 B2 | 1/2007 | Chien et al. |
| 7,161,356 B1 | 1/2007 | Chien |
| 7,169,277 B2 | 1/2007 | Ausserer et al. |
| 7,169,601 B1 | 1/2007 | Northrup et al. |
| 7,169,618 B2 | 1/2007 | Skold |
| D537,951 S | 3/2007 | Okamoto et al. |
| D538,436 S | 3/2007 | Patadia et al. |
| 7,188,001 B2 | 3/2007 | Young et al. |
| 7,192,557 B2 | 3/2007 | Wu et al. |
| 7,195,986 B1 | 3/2007 | Bousse et al. |
| 7,205,154 B2 | 4/2007 | Corson |
| 7,208,125 B1 | 4/2007 | Dong |
| 7,235,406 B1 | 6/2007 | Woudenberg et al. |
| 7,247,274 B1 | 7/2007 | Chow |
| D548,841 S | 8/2007 | Brownell et al. |
| D549,827 S | 8/2007 | Maeno et al. |
| 7,252,928 B1 | 8/2007 | Hafeman et al. |
| 7,255,833 B2 | 8/2007 | Chang et al. |
| 7,270,786 B2 | 9/2007 | Parunak et al. |
| D554,069 S | 10/2007 | Bolotin et al. |
| D554,070 S | 10/2007 | Bolotin et al. |
| 7,276,208 B2 | 10/2007 | Sevigny et al. |
| 7,276,330 B2 | 10/2007 | Chow et al. |
| 7,288,228 B2 | 10/2007 | Lefebvre |
| 7,297,313 B1 | 11/2007 | Northrup et al. |
| D556,914 S | 12/2007 | Okamoto et al. |
| 7,303,727 B1 | 12/2007 | Dubrow et al. |
| D559,995 S | 1/2008 | Handique et al. |
| 7,315,376 B2 | 1/2008 | Bickmore et al. |
| 7,323,140 B2 | 1/2008 | Handique et al. |
| 7,332,130 B2 | 2/2008 | Handique |
| 7,338,760 B2 | 3/2008 | Gong et al. |
| D566,291 S | 4/2008 | Parunak et al. |
| 7,351,377 B2 | 4/2008 | Chazan et al. |
| D569,526 S | 5/2008 | Duffy et al. |
| 7,374,949 B2 | 5/2008 | Kuriger |
| 7,390,460 B2 | 6/2008 | Osawa et al. |
| 7,419,784 B2 | 9/2008 | Dubrow et al. |
| 7,422,669 B2 | 9/2008 | Jacobson et al. |
| 7,440,684 B2 | 10/2008 | Spaid et al. |
| 7,476,313 B2 | 1/2009 | Siddiqi |
| 7,480,042 B1 | 1/2009 | Phillips et al. |
| 7,494,577 B2 | 2/2009 | Williams et al. |
| 7,494,770 B2 | 2/2009 | Wilding et al. |
| 7,514,046 B2 | 4/2009 | Kechagia et al. |
| 7,518,726 B2 | 4/2009 | Rulison et al. |
| 7,521,186 B2 | 4/2009 | Burd Mehta |
| 7,527,769 B2 | 5/2009 | Bunch et al. |
| D595,423 S | 6/2009 | Johansson et al. |
| 7,553,671 B2 | 6/2009 | Sinclair et al. |
| D596,312 S | 7/2009 | Giraud et al. |
| D598,566 S | 8/2009 | Allaer |
| 7,578,976 B1 | 8/2009 | Northrup et al. |
| D599,234 S | 9/2009 | Ito |
| 7,595,197 B2 | 9/2009 | Brasseur |
| 7,604,938 B2 | 10/2009 | Takahashi et al. |
| 7,622,296 B2 | 11/2009 | Joseph et al. |
| 7,628,902 B2 | 12/2009 | Knowlton et al. |
| 7,633,606 B2 | 12/2009 | Northrup et al. |
| 7,635,588 B2 | 12/2009 | King et al. |
| 7,645,581 B2 | 1/2010 | Knapp et al. |
| 7,670,559 B2 | 3/2010 | Chien et al. |
| 7,674,431 B2 | 3/2010 | Ganesan |
| 7,689,022 B2 | 3/2010 | Weiner et al. |
| 7,704,735 B2 | 4/2010 | Facer et al. |
| 7,705,739 B2 | 4/2010 | Northrup et al. |
| 7,723,123 B1 | 5/2010 | Murphy et al. |
| D618,820 S | 6/2010 | Wilson et al. |
| 7,727,371 B2 | 6/2010 | Kennedy et al. |
| 7,727,477 B2 | 6/2010 | Boronkay et al. |
| 7,744,817 B2 | 6/2010 | Bui |
| D621,060 S | 8/2010 | Handique |
| 7,785,868 B2 | 8/2010 | Yuan et al. |
| D628,305 S | 11/2010 | Gorrec et al. |
| 7,829,025 B2 | 11/2010 | Ganesan et al. |
| 7,858,366 B2 | 12/2010 | Northrup et al. |
| 7,867,776 B2 | 1/2011 | Kennedy et al. |
| 7,892,819 B2 | 2/2011 | Wilding et al. |
| D637,737 S | 5/2011 | Wilson et al. |
| 7,955,864 B2 | 6/2011 | Cox et al. |
| 7,987,022 B2 | 7/2011 | Handique et al. |
| 7,998,708 B2 | 8/2011 | Handique et al. |
| 8,053,214 B2 | 11/2011 | Northrup |
| 8,071,056 B2 | 12/2011 | Burns et al. |
| 8,088,616 B2 | 1/2012 | Handique |
| 8,105,783 B2 | 1/2012 | Handique |
| 8,110,158 B2 | 2/2012 | Handique |
| 8,133,671 B2 | 3/2012 | Williams et al. |
| 8,182,763 B2 | 5/2012 | Duffy et al. |
| 8,246,919 B2 | 8/2012 | Herchenbach et al. |
| 8,273,308 B2 | 9/2012 | Handique et al. |
| D669,597 S | 10/2012 | Cavada et al. |
| 8,287,820 B2 | 10/2012 | Williams et al. |
| 8,323,584 B2 | 12/2012 | Ganesan |
| 8,323,900 B2 | 12/2012 | Handique et al. |
| 8,324,372 B2 | 12/2012 | Brahmasandra et al. |
| 8,415,103 B2 | 4/2013 | Handique |
| 8,420,015 B2 | 4/2013 | Ganesan et al. |
| 8,440,149 B2 | 5/2013 | Handique |
| 8,470,586 B2 | 6/2013 | Wu et al. |
| 8,473,104 B2 | 6/2013 | Handique et al. |
| D686,749 S | 7/2013 | Trump |
| D687,567 S | 8/2013 | Jungheim et al. |
| D692,162 S | 10/2013 | Lentz et al. |
| 8,592,157 B2 | 11/2013 | Petersen et al. |
| 8,679,831 B2 | 3/2014 | Handique et al. |
| D702,854 S | 4/2014 | Nakahana et al. |
| 8,685,341 B2 | 4/2014 | Ganesan |
| 8,703,069 B2 | 4/2014 | Handique et al. |
| 8,709,787 B2 | 4/2014 | Handique |
| 8,710,211 B2 | 4/2014 | Brahmasandra et al. |
| 8,734,733 B2 | 5/2014 | Handique |
| D710,024 S | 7/2014 | Guo |
| 8,765,076 B2 | 7/2014 | Handique et al. |

(56) References Cited

U.S. PATENT DOCUMENTS

| | | |
|---|---|---|
| 8,765,454 B2 | 7/2014 | Zhou et al. |
| 8,768,517 B2 | 7/2014 | Handique et al. |
| 8,852,862 B2 | 10/2014 | Wu et al. |
| 8,883,490 B2 | 11/2014 | Handique et al. |
| 8,894,947 B2 | 11/2014 | Ganesan et al. |
| 8,895,311 B1 | 11/2014 | Handique et al. |
| D729,404 S | 5/2015 | Teich et al. |
| 9,028,773 B2 | 5/2015 | Ganesan |
| 9,040,288 B2 | 5/2015 | Handique et al. |
| 9,051,604 B2 | 6/2015 | Handique |
| 9,080,207 B2 | 7/2015 | Handique et al. |
| D742,027 S | 10/2015 | Lentz et al. |
| 9,186,677 B2 | 11/2015 | Williams et al. |
| 9,217,143 B2 | 12/2015 | Brahmasandra et al. |
| 9,222,954 B2 | 12/2015 | Lentz et al. |
| 9,234,236 B2 | 1/2016 | Thomas et al. |
| 9,238,223 B2 | 1/2016 | Handique |
| 9,259,734 B2 | 2/2016 | Williams et al. |
| 9,259,735 B2 | 2/2016 | Handique et al. |
| 9,347,586 B2 | 5/2016 | Williams et al. |
| 9,480,983 B2 | 11/2016 | Lentz et al. |
| 9,528,142 B2 | 12/2016 | Handique |
| 9,618,139 B2 | 4/2017 | Handique |
| D787,087 S | 6/2017 | Duffy et al. |
| 9,670,528 B2 | 6/2017 | Handique et al. |
| 9,677,121 B2 | 6/2017 | Ganesan et al. |
| 9,701,957 B2 | 7/2017 | Wilson et al. |
| 9,745,623 B2 | 8/2017 | Steel |
| 9,765,389 B2 | 9/2017 | Gubatayao et al. |
| 9,789,481 B2 | 10/2017 | Petersen et al. |
| 9,802,199 B2 | 10/2017 | Handique et al. |
| 9,815,057 B2 | 11/2017 | Handique |
| 9,958,466 B2 | 5/2018 | Dalbert et al. |
| 10,065,185 B2 | 9/2018 | Handique |
| 10,071,376 B2 | 9/2018 | Williams et al. |
| 10,076,754 B2 | 9/2018 | Lentz et al. |
| 10,100,302 B2 | 10/2018 | Brahmasandra et al. |
| 10,139,012 B2 | 11/2018 | Handique |
| 10,179,910 B2 | 1/2019 | Duffy et al. |
| 10,234,474 B2 | 3/2019 | Williams et al. |
| 10,351,901 B2 | 7/2019 | Ganesan et al. |
| 10,364,456 B2 | 7/2019 | Wu et al. |
| 10,443,088 B1 | 10/2019 | Wu et al. |
| 10,494,663 B1 | 12/2019 | Wu et al. |
| 10,571,935 B2 | 2/2020 | Handique et al. |
| 10,590,410 B2 | 3/2020 | Brahmasandra et al. |
| 10,604,788 B2 | 3/2020 | Wu et al. |
| 10,619,191 B2 | 4/2020 | Ganesan et al. |
| 10,625,261 B2 * | 4/2020 | Williams ................. B01L 9/06 |
| 10,625,262 B2 * | 4/2020 | Williams ............ F16K 99/0032 |
| 10,632,466 B1 * | 4/2020 | Williams ................ B01L 9/527 |
| 10,695,764 B2 | 6/2020 | Handique et al. |
| 10,710,069 B2 | 7/2020 | Handique et al. |
| 10,717,085 B2 | 7/2020 | Williams et al. |
| 10,731,201 B2 | 8/2020 | Handique et al. |
| 10,781,482 B2 | 9/2020 | Gubatayao et al. |
| 10,799,862 B2 | 10/2020 | Handique et al. |
| 10,821,436 B2 | 11/2020 | Handique et al. |
| 10,821,446 B1 | 11/2020 | Handique et al. |
| 10,822,644 B2 | 11/2020 | Steel et al. |
| 10,843,188 B2 | 11/2020 | Handique et al. |
| 10,844,368 B2 | 11/2020 | Duffy et al. |
| 10,857,535 B2 | 12/2020 | Handique et al. |
| 2001/0005489 A1 | 6/2001 | Roach et al. |
| 2001/0012492 A1 | 8/2001 | Acosta et al. |
| 2001/0016358 A1 | 8/2001 | Osawa et al. |
| 2001/0018513 A1 | 8/2001 | Baker |
| 2001/0021355 A1 | 9/2001 | Baugh et al. |
| 2001/0023848 A1 | 9/2001 | Gjerde et al. |
| 2001/0038450 A1 | 11/2001 | McCaffrey et al. |
| 2001/0045358 A1 | 11/2001 | Kopf-Sill et al. |
| 2001/0046702 A1 | 11/2001 | Schembri |
| 2001/0048899 A1 | 12/2001 | Marouiss et al. |
| 2001/0051340 A1 | 12/2001 | Singh et al. |
| 2001/0055765 A1 | 12/2001 | O'Keefe et al. |
| 2002/0001848 A1 | 1/2002 | Bedingham et al. |
| 2002/0008053 A1 | 1/2002 | Hansen et al. |
| 2002/0009015 A1 | 1/2002 | Laugharn, Jr. et al. |
| 2002/0014443 A1 | 2/2002 | Hansen et al. |
| 2002/0015667 A1 | 2/2002 | Chow |
| 2002/0021983 A1 | 2/2002 | Comte et al. |
| 2002/0022261 A1 | 2/2002 | Anderson et al. |
| 2002/0037499 A1 | 3/2002 | Quake et al. |
| 2002/0039783 A1 | 4/2002 | McMillan et al. |
| 2002/0047003 A1 | 4/2002 | Bedingham et al. |
| 2002/0053399 A1 | 5/2002 | Soane et al. |
| 2002/0054835 A1 | 5/2002 | Robotti et al. |
| 2002/0055167 A1 | 5/2002 | Pourahmadi et al. |
| 2002/0058332 A1 | 5/2002 | Quake et al. |
| 2002/0060156 A1 | 5/2002 | Mathies et al. |
| 2002/0068357 A1 | 6/2002 | Mathies et al. |
| 2002/0068821 A1 | 6/2002 | Gundling |
| 2002/0086443 A1 | 7/2002 | Bamdad |
| 2002/0090320 A1 | 7/2002 | Burow et al. |
| 2002/0092767 A1 | 7/2002 | Bjornson et al. |
| 2002/0094303 A1 | 7/2002 | Yamamoto et al. |
| 2002/0131903 A1 | 9/2002 | Ingenhoven et al. |
| 2002/0141903 A1 | 10/2002 | Parunak et al. |
| 2002/0143297 A1 | 10/2002 | Francavilla et al. |
| 2002/0155010 A1 | 10/2002 | Karp et al. |
| 2002/0155477 A1 | 10/2002 | Ito |
| 2002/0169518 A1 | 11/2002 | Luoma et al. |
| 2002/0173032 A1 | 11/2002 | Zou et al. |
| 2002/0176804 A1 | 11/2002 | Strand et al. |
| 2002/0187557 A1 | 12/2002 | Hobbs et al. |
| 2002/0192808 A1 | 12/2002 | Gambini et al. |
| 2003/0008308 A1 | 1/2003 | Enzelberger et al. |
| 2003/0008320 A1 | 1/2003 | Baker |
| 2003/0019522 A1 | 1/2003 | Parunak |
| 2003/0022392 A1 | 1/2003 | Hudak |
| 2003/0036067 A1 | 2/2003 | Schwartz |
| 2003/0049833 A1 | 3/2003 | Chen et al. |
| 2003/0059823 A1 | 3/2003 | Matsunaga et al. |
| 2003/0064507 A1 | 4/2003 | Gallagher et al. |
| 2003/0072683 A1 | 4/2003 | Stewart et al. |
| 2003/0073106 A1 | 4/2003 | Johansen et al. |
| 2003/0083686 A1 | 5/2003 | Freeman et al. |
| 2003/0087300 A1 | 5/2003 | Knapp et al. |
| 2003/0096310 A1 | 5/2003 | Hansen et al. |
| 2003/0099954 A1 | 5/2003 | Miltenyi et al. |
| 2003/0124611 A1 | 7/2003 | Schwartz |
| 2003/0127327 A1 | 7/2003 | Kurnik |
| 2003/0134333 A1 | 7/2003 | Dehlinger et al. |
| 2003/0136679 A1 | 7/2003 | Bohn et al. |
| 2003/0156991 A1 | 8/2003 | Halas et al. |
| 2003/0180192 A1 | 9/2003 | Seippel |
| 2003/0186295 A1 | 10/2003 | Colin et al. |
| 2003/0190630 A1 | 10/2003 | Blackburn et al. |
| 2003/0199081 A1 | 10/2003 | Wilding et al. |
| 2003/0211517 A1 | 11/2003 | Carulli et al. |
| 2004/0014202 A1 | 1/2004 | King et al. |
| 2004/0014238 A1 | 1/2004 | Krug et al. |
| 2004/0018116 A1 | 1/2004 | Desmond et al. |
| 2004/0018119 A1 | 1/2004 | Massaro |
| 2004/0022689 A1 | 2/2004 | Wulf et al. |
| 2004/0029258 A1 | 2/2004 | Heaney et al. |
| 2004/0029260 A1 | 2/2004 | Hansen et al. |
| 2004/0037739 A1 | 2/2004 | McNeely et al. |
| 2004/0043479 A1 | 3/2004 | Briscoe et al. |
| 2004/0053290 A1 | 3/2004 | Terbrueggen et al. |
| 2004/0063217 A1 | 4/2004 | Webster et al. |
| 2004/0065655 A1 | 4/2004 | Brown |
| 2004/0072278 A1 | 4/2004 | Chou et al. |
| 2004/0072375 A1 | 4/2004 | Gjerde et al. |
| 2004/0076996 A1 | 4/2004 | Kondo et al. |
| 2004/0086427 A1 | 5/2004 | Childers et al. |
| 2004/0086956 A1 | 5/2004 | Bachur |
| 2004/0132059 A1 | 7/2004 | Scurati et al. |
| 2004/0141887 A1 | 7/2004 | Mainquist et al. |
| 2004/0151629 A1 | 8/2004 | Pease et al. |
| 2004/0157220 A1 | 8/2004 | Kurnool et al. |
| 2004/0161788 A1 | 8/2004 | Chen et al. |
| 2004/0171515 A1 | 9/2004 | Hamers et al. |
| 2004/0189311 A1 | 9/2004 | Glezer et al. |

(56) References Cited

U.S. PATENT DOCUMENTS

| | | |
|---|---|---|
| 2004/0197810 A1 | 10/2004 | Takenaka et al. |
| 2004/0200909 A1 | 10/2004 | McMillan et al. |
| 2004/0209331 A1 | 10/2004 | Ririe |
| 2004/0209354 A1 | 10/2004 | Mathies et al. |
| 2004/0224317 A1 | 11/2004 | Kordunsky et al. |
| 2004/0235154 A1 | 11/2004 | Oh et al. |
| 2004/0240097 A1 | 12/2004 | Evans |
| 2005/0009174 A1 | 1/2005 | Nikiforov et al. |
| 2005/0013737 A1 | 1/2005 | Chow et al. |
| 2005/0019902 A1 | 1/2005 | Mathies et al. |
| 2005/0037471 A1 | 2/2005 | Liu et al. |
| 2005/0041525 A1 | 2/2005 | Pugia et al. |
| 2005/0042639 A1 | 2/2005 | Knapp et al. |
| 2005/0048540 A1 | 3/2005 | Inami et al. |
| 2005/0058574 A1 | 3/2005 | Bysouth et al. |
| 2005/0058577 A1 | 3/2005 | Micklash et al. |
| 2005/0064535 A1 | 3/2005 | Favuzzi et al. |
| 2005/0069898 A1 | 3/2005 | Moon et al. |
| 2005/0084424 A1 | 4/2005 | Ganesan et al. |
| 2005/0106066 A1 | 5/2005 | Saltsman et al. |
| 2005/0112754 A1 | 5/2005 | Yoon et al. |
| 2005/0121324 A1 | 6/2005 | Park et al. |
| 2005/0129580 A1 | 6/2005 | Swinehart et al. |
| 2005/0130198 A1 | 6/2005 | Ammann et al. |
| 2005/0133370 A1 | 6/2005 | Park et al. |
| 2005/0135655 A1 | 6/2005 | Kopf-sill et al. |
| 2005/0142036 A1 | 6/2005 | Kim et al. |
| 2005/0158781 A1 | 7/2005 | Woudenberg et al. |
| 2005/0170362 A1 | 8/2005 | Wada et al. |
| 2005/0186585 A1 | 8/2005 | Juncosa et al. |
| 2005/0196321 A1 | 9/2005 | Huang |
| 2005/0202470 A1 | 9/2005 | Sundberg et al. |
| 2005/0202489 A1 | 9/2005 | Cho et al. |
| 2005/0202504 A1 | 9/2005 | Anderson et al. |
| 2005/0205788 A1 | 9/2005 | Itoh |
| 2005/0208676 A1 | 9/2005 | Kahatt |
| 2005/0214172 A1 | 9/2005 | Burgisser |
| 2005/0220675 A1 | 10/2005 | Reed et al. |
| 2005/0227269 A1 | 10/2005 | Lloyd et al. |
| 2005/0233370 A1 | 10/2005 | Ammann et al. |
| 2005/0238545 A1 | 10/2005 | Parce et al. |
| 2005/0239127 A1 | 10/2005 | Ammann et al. |
| 2005/0266489 A1 | 12/2005 | Ammann et al. |
| 2005/0276728 A1 | 12/2005 | Muller-Cohn et al. |
| 2006/0002817 A1 | 1/2006 | Bohm et al. |
| 2006/0003373 A1 | 1/2006 | Ammann et al. |
| 2006/0041058 A1 | 2/2006 | Yin et al. |
| 2006/0057039 A1 | 3/2006 | Morse et al. |
| 2006/0057629 A1 | 3/2006 | Kim |
| 2006/0058519 A1 | 3/2006 | Deggerdal et al. |
| 2006/0062696 A1 | 3/2006 | Chow et al. |
| 2006/0081539 A1 | 4/2006 | Safar et al. |
| 2006/0094004 A1 | 5/2006 | Nakajima et al. |
| 2006/0094108 A1 | 5/2006 | Yoder et al. |
| 2006/0113190 A1 | 6/2006 | Kurnik |
| 2006/0133965 A1 | 6/2006 | Tajima et al. |
| 2006/0134790 A1 | 6/2006 | Tanaka et al. |
| 2006/0148063 A1 | 7/2006 | Fauzzi et al. |
| 2006/0154341 A1 | 7/2006 | Chen |
| 2006/0165558 A1 | 7/2006 | Witty et al. |
| 2006/0165559 A1 | 7/2006 | Greenstein et al. |
| 2006/0177376 A1 | 8/2006 | Tomalia et al. |
| 2006/0177855 A1 | 8/2006 | Utermohlen et al. |
| 2006/0183216 A1 | 8/2006 | Handique |
| 2006/0201887 A1 | 9/2006 | Siddiqi |
| 2006/0205085 A1 | 9/2006 | Handique |
| 2006/0207944 A1 | 9/2006 | Siddiqi |
| 2006/0210435 A1 | 9/2006 | Alavie et al. |
| 2006/0223169 A1 | 10/2006 | Bedingham et al. |
| 2006/0228734 A1 | 10/2006 | Vann et al. |
| 2006/0246493 A1 | 11/2006 | Jensen et al. |
| 2006/0246533 A1 | 11/2006 | Fathollahi et al. |
| 2006/0269641 A1 | 11/2006 | Atwood et al. |
| 2006/0269961 A1 | 11/2006 | Fukushima et al. |
| 2007/0004028 A1 | 1/2007 | Lair et al. |
| 2007/0009386 A1 | 1/2007 | Padmanabhan et al. |
| 2007/0020699 A1 | 1/2007 | Carpenter et al. |
| 2007/0020764 A1 | 1/2007 | Miller |
| 2007/0026421 A1 | 2/2007 | Sundberg et al. |
| 2007/0042441 A1 | 2/2007 | Masters et al. |
| 2007/0048188 A1 | 3/2007 | Bigus |
| 2007/0054413 A1 | 3/2007 | Aviles et al. |
| 2007/0077643 A1 | 4/2007 | Nakamura et al. |
| 2007/0077648 A1 | 4/2007 | Okamoto et al. |
| 2007/0092901 A1 | 4/2007 | Ligler et al. |
| 2007/0098600 A1 | 5/2007 | Kayyem et al. |
| 2007/0099200 A1 | 5/2007 | Chow et al. |
| 2007/0104617 A1 | 5/2007 | Coulling et al. |
| 2007/0116613 A1 | 5/2007 | Elsener |
| 2007/0154895 A1 | 7/2007 | Spaid et al. |
| 2007/0177147 A1 | 8/2007 | Parce |
| 2007/0178607 A1 | 8/2007 | Prober et al. |
| 2007/0184463 A1 | 8/2007 | Molho et al. |
| 2007/0184547 A1 | 8/2007 | Handique et al. |
| 2007/0196237 A1 | 8/2007 | Neuzil et al. |
| 2007/0196238 A1 | 8/2007 | Kennedy et al. |
| 2007/0199821 A1 | 8/2007 | Chow |
| 2007/0215554 A1 | 9/2007 | Kreuwel et al. |
| 2007/0218459 A1 | 9/2007 | Miller et al. |
| 2007/0231213 A1 | 10/2007 | Prabhu et al. |
| 2007/0243626 A1 | 10/2007 | Windeyer et al. |
| 2007/0248958 A1 | 10/2007 | Jovanovich et al. |
| 2007/0261479 A1 | 11/2007 | Spaid et al. |
| 2007/0269861 A1 | 11/2007 | Williams et al. |
| 2007/0292941 A1 | 12/2007 | Handique et al. |
| 2008/0000774 A1 | 1/2008 | Park et al. |
| 2008/0003649 A1 | 1/2008 | Maltezos et al. |
| 2008/0017306 A1 | 1/2008 | Liu et al. |
| 2008/0056948 A1 | 3/2008 | Dale et al. |
| 2008/0069729 A1 | 3/2008 | McNeely |
| 2008/0090244 A1 | 4/2008 | Knapp et al. |
| 2008/0095673 A1 | 4/2008 | Xu |
| 2008/0118987 A1 | 5/2008 | Eastwood et al. |
| 2008/0124723 A1 | 5/2008 | Dale et al. |
| 2008/0176230 A1 | 7/2008 | Owen et al. |
| 2008/0192254 A1 | 8/2008 | Kim et al. |
| 2008/0226502 A1 | 9/2008 | Jonsmann et al. |
| 2008/0240898 A1 | 10/2008 | Manz et al. |
| 2008/0247914 A1 | 10/2008 | Edens et al. |
| 2008/0257882 A1 | 10/2008 | Turner |
| 2008/0280285 A1 | 11/2008 | Chen et al. |
| 2008/0308500 A1 | 12/2008 | Brassard |
| 2009/0047180 A1 | 2/2009 | Kawahara |
| 2009/0066339 A1 | 3/2009 | Glezer et al. |
| 2009/0136385 A1 | 5/2009 | Handique et al. |
| 2009/0148933 A1 | 6/2009 | Battrell et al. |
| 2009/0189089 A1 | 7/2009 | Bedingham et al. |
| 2009/0223925 A1 | 9/2009 | Morse et al. |
| 2009/0325164 A1 | 12/2009 | Vossenaar et al. |
| 2009/0325276 A1 | 12/2009 | Battrell et al. |
| 2010/0009351 A1 | 1/2010 | Brahmasandra et al. |
| 2010/0120129 A1 | 5/2010 | Amshey et al. |
| 2010/0233763 A1 | 9/2010 | Shigeura et al. |
| 2010/0284864 A1 | 11/2010 | Holenstein et al. |
| 2011/0008825 A1 | 1/2011 | Ingber et al. |
| 2011/0027151 A1 | 2/2011 | Handique et al. |
| 2011/0060136 A1* | 3/2011 | Matsunaga ........... H01F 1/0054 536/23.1 |
| 2011/0097493 A1 | 4/2011 | Kerr et al. |
| 2011/0127292 A1 | 6/2011 | Sarofim et al. |
| 2011/0158865 A1 | 6/2011 | Miller et al. |
| 2011/0287447 A1 | 11/2011 | Norderhaug |
| 2011/0300033 A1 | 12/2011 | Battisti |
| 2012/0122231 A1 | 5/2012 | Tajima |
| 2012/0160826 A1 | 6/2012 | Handique |
| 2012/0171678 A1 | 7/2012 | Maltezos et al. |
| 2012/0258463 A1 | 10/2012 | Duffy et al. |
| 2013/0183769 A1 | 7/2013 | Tajima |
| 2013/0210127 A1* | 8/2013 | Williams ................ B01L 7/52 435/287.2 |
| 2013/0217013 A1 | 8/2013 | Steel et al. |
| 2013/0315800 A1 | 11/2013 | Yin et al. |
| 2014/0030798 A1 | 1/2014 | Wu et al. |

(56) References Cited

U.S. PATENT DOCUMENTS

| | | | |
|---|---|---|---|
| 2014/0120544 A1* | 5/2014 | Brahmasandra | B01L 3/502753 435/6.12 |
| 2014/0227710 A1 | 8/2014 | Handique et al. | |
| 2014/0329301 A1 | 11/2014 | Handique et al. | |
| 2015/0045234 A1 | 2/2015 | Stone et al. | |
| 2015/0064702 A1 | 3/2015 | Handique et al. | |
| 2015/0174579 A1 | 6/2015 | Iten et al. | |
| 2015/0315631 A1 | 11/2015 | Handique et al. | |
| 2016/0038942 A1 | 2/2016 | Roberts | |
| 2017/0275702 A1 | 9/2017 | Dahiya et al. | |
| 2018/0112252 A1 | 4/2018 | Handique | |
| 2018/0135102 A1 | 5/2018 | Gubatayao et al. | |
| 2018/0154364 A1 | 6/2018 | Handique et al. | |
| 2018/0333722 A1 | 11/2018 | Handique | |
| 2019/0054467 A1 | 2/2019 | Handique | |
| 2019/0054471 A1 | 2/2019 | Williams et al. | |
| 2019/0144849 A1 | 5/2019 | Duffy et al. | |
| 2019/0145546 A1 | 5/2019 | Handique | |
| 2019/0151854 A1 | 5/2019 | Baum et al. | |
| 2019/0154719 A1 | 5/2019 | LaChance et al. | |
| 2019/0284606 A1 | 9/2019 | Wu et al. | |
| 2019/0324050 A1 | 10/2019 | Williams et al. | |
| 2020/0139363 A1 | 5/2020 | Handique et al. | |
| 2020/0156059 A1 | 5/2020 | Handique et al. | |
| 2020/0156060 A1 | 5/2020 | Handique et al. | |
| 2020/0164363 A1 | 5/2020 | Handique et al. | |
| 2020/0216831 A1* | 7/2020 | Brahmasandra | C12Q 1/6813 |
| 2020/0291388 A1 | 9/2020 | Brahmasandra et al. | |
| 2020/0324293 A1 | 10/2020 | Handique et al. | |
| 2020/0325523 A1 | 10/2020 | Brahmasandra et al. | |
| 2020/0325524 A1 | 10/2020 | Handique et al. | |

FOREIGN PATENT DOCUMENTS

| | | |
|---|---|---|
| AU | 4437602 | 7/2002 |
| AU | 4437702 | 7/2002 |
| AU | 764319 B2 | 8/2003 |
| CA | 2574107 | 9/1998 |
| CA | 2294819 | 1/1999 |
| CN | 1312287 C | 4/2007 |
| CN | 1942590 A | 4/2007 |
| CN | 1968754 A | 5/2007 |
| CN | 101466848 | 6/2009 |
| CN | 101522909 | 9/2009 |
| CN | 103540518 | 1/2014 |
| DE | 19755479 A1 | 6/1999 |
| DE | 19929734 | 12/1999 |
| DE | 19833293 C1 | 1/2000 |
| EP | 0136126 A2 | 4/1985 |
| EP | 0365828 A2 | 5/1990 |
| EP | 0483620 A2 | 5/1992 |
| EP | 0402994 B1 | 11/1994 |
| EP | 0393744 B1 | 1/1995 |
| EP | 0688602 A2 | 12/1995 |
| EP | 0707077 A2 | 4/1996 |
| EP | 0698046 B1 | 3/1997 |
| EP | 0766256 | 4/1997 |
| EP | 0772494 B1 | 5/1997 |
| EP | 0810030 A1 | 12/1997 |
| EP | 1059458 A2 | 12/2000 |
| EP | 1064090 A1 | 1/2001 |
| EP | 1077086 A2 | 2/2001 |
| EP | 1346772 A2 | 9/2003 |
| EP | 1541237 A2 | 6/2005 |
| EP | 1574586 A2 | 9/2005 |
| EP | 1621890 A1 | 2/2006 |
| EP | 1745153 | 1/2007 |
| EP | 1780290 A2 | 5/2007 |
| EP | 1792656 A1 | 6/2007 |
| EP | 2372367 A1 | 10/2011 |
| FR | 2672301 | 8/1992 |
| FR | 2795426 | 12/2000 |
| GB | 2453432 A | 4/2009 |
| JP | S50-100881 | 8/1975 |
| JP | 58212921 A | 12/1983 |
| JP | S62-119460 | 5/1987 |
| JP | H01-502319 | 8/1989 |
| JP | H 03181853 | 8/1991 |
| JP | 04-053555 U | 5/1992 |
| JP | 06-064156 U | 9/1994 |
| JP | 07-020010 | 1/1995 |
| JP | H07-290706 | 11/1995 |
| JP | H08-122336 | 5/1996 |
| JP | H08-173194 | 7/1996 |
| JP | H08-211071 | 8/1996 |
| JP | H08-285859 | 11/1996 |
| JP | H08-337116 | 12/1996 |
| JP | H09-304385 | 11/1997 |
| JP | H09-325151 | 12/1997 |
| JP | 2001-502790 | 1/1998 |
| JP | H01-219669 | 9/1998 |
| JP | H10-327515 | 12/1998 |
| JP | H11-009258 | 1/1999 |
| JP | H11-501504 | 2/1999 |
| JP | H11-503315 | 3/1999 |
| JP | 2000-514928 | 4/1999 |
| JP | H11-156231 | 6/1999 |
| JP | H11-316226 | 11/1999 |
| JP | H11-515106 | 12/1999 |
| JP | 2000-180455 | 6/2000 |
| JP | 2000-266760 | 9/2000 |
| JP | 2000-275255 | 10/2000 |
| JP | 2001-502319 | 2/2001 |
| JP | 2001-204462 | 7/2001 |
| JP | 2001-509437 | 7/2001 |
| JP | 3191150 B2 | 7/2001 |
| JP | 2001-515216 | 9/2001 |
| JP | 2001-523812 | 11/2001 |
| JP | 2001-527220 | 12/2001 |
| JP | 2002-503331 | 1/2002 |
| JP | 2002-085961 | 3/2002 |
| JP | 2002-517735 | 6/2002 |
| JP | 2002-215241 | 7/2002 |
| JP | 2002-540382 | 11/2002 |
| JP | 2002-544476 | 12/2002 |
| JP | 2003-500674 | 1/2003 |
| JP | 2003-047839 A | 2/2003 |
| JP | 2003-047840 A | 2/2003 |
| JP | 2003-516125 | 5/2003 |
| JP | 2003-164279 | 6/2003 |
| JP | 2003-185584 | 7/2003 |
| JP | 2003-299485 | 10/2003 |
| JP | 2003-329693 | 11/2003 |
| JP | 2003-329696 | 11/2003 |
| JP | 2003-532382 A | 11/2003 |
| JP | 2004-003989 | 1/2004 |
| JP | 2004-506179 A | 2/2004 |
| JP | 2004-150797 A | 5/2004 |
| JP | 2004-283728 A | 10/2004 |
| JP | 2004-531360 A | 10/2004 |
| JP | 2004-533838 | 11/2004 |
| JP | 2004-534157 | 11/2004 |
| JP | 2004-361421 | 12/2004 |
| JP | 2004-536291 | 12/2004 |
| JP | 2004-536689 A | 12/2004 |
| JP | 2005-009870 | 1/2005 |
| JP | 2005-010179 | 1/2005 |
| JP | 2005-511264 | 4/2005 |
| JP | 2005-514718 | 5/2005 |
| JP | 2005-518825 | 6/2005 |
| JP | 2005-176613 A | 7/2005 |
| JP | 2005-192439 | 7/2005 |
| JP | 2005-192554 | 7/2005 |
| JP | 2005-519751 | 7/2005 |
| JP | 2005-204661 | 8/2005 |
| JP | 2005-525816 | 9/2005 |
| JP | 2005-291954 A | 10/2005 |
| JP | 2005-532043 | 10/2005 |
| JP | 2005-323519 | 11/2005 |
| JP | 2005-533652 | 11/2005 |
| JP | 2005-535904 | 11/2005 |
| JP | 2006-021156 A | 1/2006 |
| JP | 2006-055837 A | 3/2006 |

(56) References Cited

FOREIGN PATENT DOCUMENTS

| | | |
|---|---|---|
| JP | 2006-094866 A | 4/2006 |
| JP | 2006-145458 | 6/2006 |
| JP | 2006-167569 | 6/2006 |
| JP | 2006-284409 | 10/2006 |
| JP | 2007-024742 A | 2/2007 |
| JP | 2007-074960 | 3/2007 |
| JP | 2007-097477 | 4/2007 |
| JP | 2007-101364 | 4/2007 |
| JP | 2007-510518 | 4/2007 |
| JP | 2007-514405 A | 6/2007 |
| JP | 2007-178328 | 7/2007 |
| JP | 2007-535933 | 12/2007 |
| JP | 2009-515140 | 4/2009 |
| JP | 2009-542207 | 12/2009 |
| JP | 3193848 U | 10/2014 |
| KR | 1020060044489 A | 5/2006 |
| RU | 2418633 C2 | 5/2011 |
| WO | WO 1988/006633 | 9/1988 |
| WO | WO 1990/012350 | 10/1990 |
| WO | WO 1992/005443 | 4/1992 |
| WO | WO 1994/005414 | 3/1994 |
| WO | WO 1994/011103 | 5/1994 |
| WO | WO 1995/033846 | 12/1994 |
| WO | WO 1996/000228 | 1/1996 |
| WO | WO 1996/004547 | 2/1996 |
| WO | WO 1996/018731 | 6/1996 |
| WO | WO 1996/039547 | 12/1996 |
| WO | WO 1997/005492 | 2/1997 |
| WO | WO 1997/016835 | 5/1997 |
| WO | WO 1997/021090 | 6/1997 |
| WO | WO 1997/022825 | 6/1997 |
| WO | WO 1997/027324 | 7/1997 |
| WO | WO 1998/000231 | 1/1998 |
| WO | WO 1998/007019 | 2/1998 |
| WO | WO 1998/022625 | 5/1998 |
| WO | WO 1998/035013 | 8/1998 |
| WO | WO 1998/038487 | 9/1998 |
| WO | WO 1998/049548 | 11/1998 |
| WO | WO 1998/050147 | 11/1998 |
| WO | WO 1998/053311 | 11/1998 |
| WO | WO 1999/001688 | 1/1999 |
| WO | WO 1999/009042 | 2/1999 |
| WO | WO 1999/012016 | 3/1999 |
| WO | WO 1999/017093 | 4/1999 |
| WO | WO 1999/029703 | 6/1999 |
| WO | WO 1999/033559 | 7/1999 |
| WO | WO 1999/060397 | 11/1999 |
| WO | WO 2000/022436 | 4/2000 |
| WO | WO 2000/075623 | 12/2000 |
| WO | WO 2000/078455 | 12/2000 |
| WO | WO 2001/005510 | 1/2001 |
| WO | WO 2001/014931 | 3/2001 |
| WO | WO 2001/027614 | 4/2001 |
| WO | WO 2001/028684 | 4/2001 |
| WO | WO 2001/030995 | 5/2001 |
| WO | WO 2001/041931 | 6/2001 |
| WO | WO 2001/046474 | 6/2001 |
| WO | WO 2001/054813 | 8/2001 |
| WO | WO 2001/089681 | 11/2001 |
| WO | WO 2001/089705 | 11/2001 |
| WO | WO 2001/092569 | 12/2001 |
| WO | WO 2002/048164 | 6/2002 |
| WO | WO 2002/052002 | 7/2002 |
| WO | WO 2002/072264 | 9/2002 |
| WO | WO 2002/078845 | 10/2002 |
| WO | WO 2002/086454 | 10/2002 |
| WO | WO 2002/094185 | 11/2002 |
| WO | WO 2003/007677 | 1/2003 |
| WO | WO 2003/012325 | 2/2003 |
| WO | WO 2003/012406 | 2/2003 |
| WO | WO 2003/048295 | 6/2003 |
| WO | WO 2003/055605 | 7/2003 |
| WO | WO 2003/076661 | 9/2003 |
| WO | WO 2003/078065 | 9/2003 |
| WO | WO 2003/080868 | 10/2003 |
| WO | WO 2003/087410 | 10/2003 |
| WO | WO 2004/007081 | 1/2004 |
| WO | WO 2004/010760 | 2/2004 |
| WO | WO 2004/048545 | 6/2004 |
| WO | WO 2004/055522 | 7/2004 |
| WO | WO 2004/056485 | 7/2004 |
| WO | WO 2004/074848 | 9/2004 |
| WO | WO 2004/094986 | 11/2004 |
| WO | WO 2005/008255 | 1/2005 |
| WO | WO 2005/011867 | 2/2005 |
| WO | WO 2005/030984 | 4/2005 |
| WO | WO 2005/072353 | 8/2005 |
| WO | WO 2005/094981 | 10/2005 |
| WO | WO 2005/107947 | 11/2005 |
| WO | WO 2005/108571 | 11/2005 |
| WO | WO 2005/108620 | 11/2005 |
| WO | WO 2005/116202 | 12/2005 |
| WO | WO 2005/118867 | 12/2005 |
| WO | WO 2005/120710 | 12/2005 |
| WO | WO 2006/010584 | 2/2006 |
| WO | WO 2006/032044 | 3/2006 |
| WO | WO 2006/035800 | 4/2006 |
| WO | WO 2006/043642 | 4/2006 |
| WO | WO 2006/066001 | 6/2006 |
| WO | WO 2006/079082 | 7/2006 |
| WO | WO 2006/081995 | 8/2006 |
| WO | WO 2006/113198 | 10/2006 |
| WO | WO 2006/118420 | 11/2006 |
| WO | WO 2006/119280 | 11/2006 |
| WO | WO 2007/044917 | 4/2007 |
| WO | WO-2007041619 A2 * 4/2007 ........ B01L 3/502761 |
| WO | WO 2007/050327 | 5/2007 |
| WO | WO 2007/064117 | 6/2007 |
| WO | WO 2007/075919 | 7/2007 |
| WO | WO 2007/091530 | 8/2007 |
| WO | WO 2007/112114 | 10/2007 |
| WO | WO 2007/120240 | 10/2007 |
| WO | WO 2007/120241 | 10/2007 |
| WO | WO 2008/005321 | 1/2008 |
| WO | WO 2008/030914 | 3/2008 |
| WO | WO 2008/060604 | 5/2008 |
| WO | WO-2008134470 A2 * 11/2008 ........... C12Q 1/6806 |
| WO | WO 2008/149282 | 12/2008 |
| WO | WO 2009/012185 | 1/2009 |
| WO | WO 2009/054870 | 4/2009 |
| WO | WO 2010/118541 | 10/2010 |
| WO | WO 2010/130310 | 11/2010 |
| WO | WO 2010/140680 | 12/2010 |
| WO | WO 2011/009073 | 1/2011 |
| WO | WO 2011/101467 | 8/2011 |

OTHER PUBLICATIONS

Benters et al., "Dendrimer-Activated Solid Supports for Nucleic Acid and Protein Microarrays" ChemBioChem vol. 2 pp. 686-694 (Year: 2001).*

Allemand et al., "pH-Dependent Specific Binding and Combing of DNA", Biophys J. (1997) 73(4): 2064-2070.

Altet et al., [Eds.] "Thermal Transfer and Thermal Coupling in IC's", Thermal Testing of Integrated Circuits; Chapter 2 (2002) Springer Science pp. 23-51.

Ateya et al., "The good, the bad, and the tiny: a review of microflow cytometry", Anal Bioanal Chem. (2008) 391(5):1485-1498.

Auroux et al., "Miniaturised nucleic acid analysis", Lab Chip. (2004) 4(6):534-546.

Baechi et al., "High-density microvalve arrays for sample processing in PCR chips", Biomed Microdevices. (2001) 3(3):183-190.

Baker M., "Clever PCR: more genotyping, smaller volumes." Nature Methods (May 2010) 70(5):351-356.

Becker H. "Fabrication of Polymer Microfluidic Devices", in Biochip Technology (2001), Chapter 4, pp. 63-96.

Becker H., "Microfluidic Devices Fabricated by Polymer Hot Embossing," in Integrated Microfabricated Biodevices: Advanced Technologies for Genomics, Drug Discovery, Bioanalysis, and Clinical Diagnostics (2002), Chapter 13, 32 pages.

Becker H., "Microfluidics: A Technology Coming of Age", Med Device Technol. (2008) 19(3):21-24.

(56) References Cited

OTHER PUBLICATIONS

Becker et al., "Portable CE system with contactless conductivity detection in an injection molded polymer chip for on-site food analysis", SPIE Proceedings MOEMS-MEMS 2008 Micro and Nanofabrication (2008) vol. 6886 in 8 pages.

Becker H., "Hype, hope and hubris: the quest for the killer application in microfluidics", Lab on a Chip, The Royal Society of Chemistry (2009) 9:2119-2122.

Becker H., "Collective Wisdom", Lab on a Chip, The Royal Society of Chemistry (2010) 10:1351-1354.

Belgrader et al., "Rapid PCR for Identity Testing Using a Battery-Powered Miniature Thermal Cycler", J Forensic Sci. (1998) 43(2):315-319.

Belgrader et al., "A minisonicator to rapidly disrupt bacterial spores for DNA analysis", Anal Chem. (1999) 71 (19):4232-4236.

Belgrader et al., "Real-time PCR Analysis on Nucleic Acids Purified from Plasma Using a Silicon Chip", Micro Total Analysis Systems 2000 (pp. 525-528). Springer, Dordrecht.

Belgrader et al., "A microfluidic cartridge to prepare spores for PCR analysis", Biosens Bioelectron. (2000) 14(10-11):849-852.

Belgrader et al., "A Battery-Powered Notebook Thermal Cycler for Rapid Multiplex Real-Time PCR Analysis", Anal Chem. (2001) 73(2):286-289.

Belgrader et al., "Rapid and Automated Cartridge-based Extraction of Leukocytes from Whole Blood for Microsatellite DNA Analysis by Capillary Electrophoresis", Clin Chem. (2001) 47(10):1917-1933.

Belgrader et al., "A Rapid, Flow-through, DNA Extraction Module for Integration into Microfluidic Systems", Micro Total Analysis Systems (2002) pp. 697-699). Springer, Dordrecht.

Belgrader et al., "Development of a Battery-Powered Portable Instrumentation for Rapid PCR Analysis", in Integrated Microfabricated Devices, (2002) Ch. 8, pp. 183-206, CRC Press.

Bell M., "Integrated Microsystems in Clinical Chemistry", in Integrated Microfabricated Devices (2002) Ch. 16, pp. 415-435, CRC Press.

Berthier et al., "Managing evaporation for more robust microscale assays Part 1. Volume loss in high throughput assays", Lab Chip (2008) 8(6):852-859.

Berthier et al., "Managing evaporation for more robust microscale assays Part 2. Characterization of convection and diffusion for cell biology", Lab Chip (2008) 8(6):860-864.

Berthier et al., "Microdrops," in Microfluidics for Biotechnology (2006), Chapter 2, pp. 51-88.

BIOMERIEUX Press Release: "bioMérieux—2018 Financial Results," dated Feb. 27, 2019, accessed at www.biomerieux.com, pp. 13.

Blanchard et al., "Micro structure mechanical failure characterization using rotating Couette flow in a small gap", J Micromech Microengin. (2005) 15(4):792-801.

Blanchard et al., "Single-disk and double-disk viscous micropumps", Sensors and Actuators A (2005) 122:149-158.

Blanchard et al., "Performance and Development of a Miniature Rotary Shaft Pump", J Fluids Eng. (2005) 127(4):752-760.

Blanchard et al., "Single-disk and double-disk viscous micropump", ASME 2004 Inter'l Mechanical Engineering Congress & Exposition, Nov. 13-20, 2004, Anaheim, CA, IMECE2004-61705:411-417.

Blanchard et al., "Miniature Single-Disk Viscous Pump (Single-DVP), Performance Characterization", J Fluids Eng. (2006) 128(3):602-610.

Bollet, C. et al., "A simple method for the isolation of chromosomal DNA from Gram positive or acid-fast bacteria", Nucleic Acids Research, vol. 19, No. 8 (1991), p. 1955.

Brahmasandra et al., On-chip DNA detection in microfabricated separation systems, SPIE Conference on Microfluidic Devices and Systems, 1998, vol. 3515, pp. 242-251, Santa Clara, CA.

Brahmasandra et al., "Microfabricated Devices for Integrated DNA Analysis", in Biochip Technology by Cheng et al., [Eds.] (2001) pp. 229-250.

Breadmore, M.C. et al., "Microchip-Based Purification of DNA from Biological Samples", Anal. Chem., vol. 75 (2003), pp. 1880-1886.

Brody, et al., Diffusion-Based Extraction in a Microfabricated Device, Sensors and Actuators Elsevier, 1997, vol. A58, No. 1, pp. 13-18.

Broyles et al., "Sample Filtration, Concentration, and Separation Integrated on Microfluidic Devices" Analytical Chemistry (American Chemical Society), (2003) 75(11): 2761-2767.

Bu et al., "Design and theoretical evaluation of a novel microfluidic device to be used for PCR", J Micromech Microengin. (2003) 13(4):S125-S130.

Burns et al., "An Integrated Nanoliter DNA Analysis Device", Science 282:484-487 (1998).

Cady et al., "Real-time PCR detection of Listeria monocytogenes using an integrated microfluidics platform", Sensors Actuat B. (2005) 107:332-341.

Carlen et al., "Paraffin Actuated Surface Micromachined Valve," in IEEE MEMS 2000 Conference, Miyazaki, Japan (Jan. 2000) pp. 381-385.

Carles et al., "Polymerase Chain Reaction on Microchips" in Methods in Molecular Biology—Microfluidic Techniques, Reviews & Protocols by Minteer S.D. [Ed.] Humana Press (2006), vol. 321; Chapter 11, pp. 131-140.

Chang-Yen et al., "A novel integrated optical dissolved oxygen sensor for cell culture and micro total analysis systems", IEEE Technical Digest MEMS International Conference Jan. 24, 2002, 4 pages.

Chang-Yen et al., "A PDMS microfluidic spotter for fabrication of lipid microarrays", IEEE 3rd EMBS Special Topic Conference May 12-15, 2005; 2 pages.

Chang-Yen et al., "Design and fabrication of a multianalyte-capable optical biosensor using a multiphysics approach", IEEE 3rd EMBS Special Topic Conference May 12-15, 2005; 2 pages.

Chang-Yen et al., "A Novel PDMS Microfluidic Spotter for Fabrication of Protein Chips and Microarrays", IEEE J of Microelectromech Sys. (2006) 15(5): 1145-1151.

Chang-Yen et al., "Design, fabrication, and packaging of a practical multianalyte-capable optical biosensor," J Microlith Microfab Microsyst. (2006) 5(2):021105 in 8 pages.

Chang-Yen et al., "Spin-assembled nanofilms for gaseous oxygen sensing." Sens Actuators B: Chemical (2007), 120(2):426-433.

Chaudhari et al., "Transient Liquid Crystal Thermometry of Microfabricated PCR Vessel Arrays", J Microelectro Sys., (1998) 7(4):345-355.

Chen P.-C., "Accelerating micro-scale PCR (polymerase chain reactor) for modular lab-on-a-chip system", LSU Master's Theses—Digital Commons, (2006) 111 pages.

Chen et al., "Total nucleic acid analysis integrated on microfluidic devices," Lab on a Chip. (2007) 7:1413-1423.

Cheng et al., "Biochip-Based Portable Laboratory", Biochip Tech. (2001):269-289.

Cho et al., "A facility for characterizing the steady-state and dynamic thermal performance of microelectromechanical system thermal switches", Rev Sci Instrum. (2008) 79(3):034901-1 to -8.

Chong et al., "Disposable Polydimethylsioxane Package for 'Bio-Microfluidic System'", IEEE Proceedings Electronic Components and Technology (2005); 5 pages.

Chou et al., "A miniaturized cyclic PCR device—modeling and experiments", Microelec Eng. (2002) 61-62:921-925.

Christel et al., "Nucleic Acid Concentration and PCR for Diagnostic Applications", in Micro Total Analysis Systems. (1998) D.J. Harrison et al. [Eds.] pp. 277-280.

Christel et al., "Rapid, Automated Nucleic Acid Probe Assays Using Silicon Microstructures for Nucleic Acid Concentration", J Biomech Eng. (1999) 121(1):22-27.

Christensen et al., "Characterization of interconnects used in PDMS microfluidic systems", J Micromech Microeng. (2005) 15:928 in 8 pages.

Chung, Y. et al., "Microfluidic chip for high efficiency DNA extraction", Miniaturisation for Chemistry, Biology & Bioengineering, vol. 4, No. 2 (Apr. 2004), pp. 141-147.

(56) References Cited

OTHER PUBLICATIONS

Cooley et al., "Applications of Ink-Jet Printing Technology to BioMEMS and Microfluidic Systems", Proceedings, SPIE Conference on Microfluids and BioMEMS, (Oct. 2001), 12 pages.
Crews et al., "Rapid Prototyping of a Continuous-Flow PCR Microchip", Proceedings of the AiChE Annual Meeting (Nov. 15, 2006) (335a) 3 pages.
Crews et al., Thermal gradient PCR in a continuous-flow microchip. In Microfluidics, BioMEMS, and Medical Microsystems V; Jan. 2007; vol. 6465, p. 646504; 12 pages.
Crews et al., "Continuous-flow thermal gradient PCR", Biomed Microdevices. (2008) 10(2):187-195.
Cui et al., "Electrothermal modeling of silicon PCR chips", In MEMS Design, Fabrication, Characterization, and Packaging, (Apr. 2001) (vol. 4407, pp. 275-280.
Cui et al., "Design and Experiment of Silicon PCR Chips," Proc. SPIE 4755, Design, Test, Integration, and Packaging of MEMS/MOEMS 2002, (Apr. 19, 2002) pp. 71-76.
Danaher Press Release: "Danaher to Acquire Cepheid for $53.00 per share, or approximately $4 Billion," dated Sep. 6, 2016, accessed at www.danaher.com, pp. 3.
Demchenko A.P., "The problem of self-calibration of fluorescence signal in microscale sensor systems", Lab Chip. (2005) 5(11):1210-1223.
Dineva et al., "Sample preparation: a challenge in the development of point-of-care nucleic acid-based assays for resource-limited settings", Analyst. (2007) 132(12):1193-1199.
Dishinger et al., "Multiplexed Detection and Applications for Separations on Parallel Microchips", Electophoresis. (2008) 29(16):3296-3305.
Dittrich et al., "Single-molecule fluorescence detection in microfluidic channels—the Holy Grail in muTAS?", Anal Bioanal Chem. (2005) 382(8):1771-1782.
Dittrich et al., "Lab-on-a-chip: microfluidics in drug discovery", Nat Rev Drug Discov. (2006) 5(3):210-208.
Dunnington et al., "Approaches to Miniaturized High-Throughput Screening of Chemical Libraries", in Integrated Microfabricated Devices (2002) Ch. 15, pp. 371-414, CRC Press.
Eddings et al., "A PDMS-based gas permeation pump for on-chip fluid handling in microfluidic devices", J Micromech Microengin. (2006) 16(11):2396-2402.
Edwards, "Silicon (Si)," in "Handbook of Optical Constants of Solids" (Ghosh & Palik eds., 1997) in 24 pages.
Edwards et al., "Micro Scale Purification Systems for Biological Sample Preparation", Biomed Microdevices (2001) 3(3):211-218.
Edwards et al., "A microfabricated thermal field-flow fractionation system", Anal Chem. (2002) 74(6):1211-1216.
Ehrlich et al., "Microfluidic devices for DNA analysis", Trends Biotechnol. (1999) 17(8):315-319.
El-Ali et al., "Simulation and experimental validation of a SU-8 based PCR thermocycler chip with integrated heaters and temperature sensor", Sens Actuators A: Physical (2004) 110(1-3):3-10.
EP Communication dated Aug. 9, 2006 for European Patent Application 02723636.3, filed Mar. 27, 2002.
Erickson et al., "Joule heating and heat transfer in poly(dimethylsiloxane) microfluidic systems", Lab Chip (2003) 3(3):141-149.
Erickson et al., "Integrated Microfluidic Devices", Analytica Chim Acta. (2004) 507:11-26.
Erill et al., "Development of a CMOS-compatible PCR chip: comparison of design and system strategies", J Micromech Microengin. (2004) 14(11):1-11.
European Supplemental Search Report dated Aug. 5, 2010 for Application No. EP 08826342.1, filed Jul. 11, 2008.
Fair R.B., Digital microfluidics: is a true lab-on-a-chip possible? Microfluidics Nanofluid. (2007) 3:245-281.
Fan et al., "Integrated Plastic Microfluidic Devices for Bacterial Detection", in Integrated Biochips for DNA Analysis by Liu et al. [Eds], (2007) Chapter 6, pp. 78-89.
Fiorini et al., "Disposable microfluidic devices: fabrication, function, and application", Biotechniques (2005) 38(3):429-446.

Frazier et al., "Integrated micromachined components for biological analysis systems", J Micromech. (2000) 1(1):67-83.
Gale et al., "Micromachined electrical field-flow fractionation (mu-EFFF) system", IEEE Trans Biomed Eng. (1998) 45(12):1459-1469.
Gale et al., "Geometric scaling effects in electrical field flow fractionation. 1. Theoretical analysis", Anal Chem. (2001) 73(10):2345-2352.
Gale et al., "BioMEMS Education at Louisiana Tech University", Biomed Microdevices, (2002) 4:223-230.
Gale et al., "Geometric scaling effects in electrical field flow fractionation. 2. Experimental results", Anal Chem. (2002) 74(5):1024-1030.
Gale et al., "Cyclical electrical field flow fractionation", Electrophoresis (2005) 26(9):1623-1632.
Gale et al., "Low-Cost MEMS Technologies", Elsevier B.V. (2008), Chapter 1.12; pp. 342-372.
Garst et al., "Fabrication of Multilayered Microfluidic 3D Polymer Packages", IEEE Proceedings Electronic Components & Tech, Conference May/Jun. 2005, pp. 603-610.
Gärtner et al., "Methods and instruments for continuous-flow PCR on a chip", Proc. SPIE 6465, Microfluidics, BioMEMS, and Medical Microsystems V, (2007) 646502; 8 pages.
Giordano et al., "Toward an Integrated Electrophoretic Microdevice for Clinical Diagnostics", in Integrated Microfabricated Biodevices: Advanced Technologies for Genomics, Drug Discovery, Bioanalysis, and Clinical Diagnostics (2002) Chapter 1; pp. 1-34.
Goldmeyer et al., "Identification of *Staphylococcus aureus* and Determination of Methicillin Resistance Directly from Positive Blood Cultures by Isothermal Amplification and a Disposable Detection Device", J Clin Microbiol. (Apr. 2008) 46(4): 1534-1536.
Graff et al., "Nanoparticle Separations Using Miniaturized Field-flow Fractionation Systems", Proc. Nanotechnology Conference and Trade Show (NSTI) (2005); pp. 8-12.
Greer et al., "Comparison of glass etching to xurography prototyping of microfluidic channels for DNA melting analysis", J Micromech Microengin. (2007) 17(12):2407-2413.
Grunenwald H., "Optimization of Polymerase Chain Reactions," in Methods in Molecular Biology, PCR Protocols., Second Edition by Bartlett et al. [Eds.] Humana Press (2003) vol. 226, pp. 89-99.
Guijt et al., "Chemical and physical processes for integrated temperature control in microfluidic devices", Lab Chip. (2003) 3(1):1-4.
Gulliksen A., "Microchips for Isothermal Amplification of RNA", Doctoral Thesis (2007); Department of Mol. Biosciences-University of Oslo; 94 pages.
Guttenberg et al., "Planar chip device for PCR and hybridization with surface acoustic wave pump", Lab Chip. (2005) 5(3):308-317.
Haeberle et al., "Microfluidic platforms for lab-on-a-chip applications", Lab Chip. (2007) 7(9):1094-1110.
Hale et al., "Optical constants of Water in the 200-nm to 200-µm Wavelength Region", Applied Optics, 12(3): 555-563 (1973).
Handal et al., "DNA mutation detection and analysis using miniaturized microfluidic systems", Expert Rev Mol Diagn. (2006) 6(1):29-38.
Handique et al., "Microfluidic flow control using selective hydrophobic patterning", SPIE, (1997) 3224: 185-194.
Handique et al., "On-Chip Thermopneumatic Pressure for Discrete Drop Pumping", Anal. Chem., (2001) 73(8):1831-1838.
Handique et al., "Nanoliter-volume discrete drop injection and pumping in microfabricated chemical analysis systems", Solid-State Sensor and Actuator Workshop (Hilton Head, South Carolina, Jun. 8-11, 1998) pp. 346-349.
Handique et al., "Mathematical Modeling of Drop Mixing in a Slit-Type Microchannel", J. Micromech. Microeng., 11:548-554 (2001).
Handique et al., "Nanoliter Liquid Metering in Microchannels Using Hydrophobic Patterns", Anal. Chem., 72(17):4100-4109 (2000).
Hansen et al., "Microfluidics in structural biology: smaller, faster . . . better", Curr Opin Struct Biol. (2003) 13(5):538-544.
Harding et al., "DNA isolation using Methidium-Spermine-Sepharose", Meth Enzymol. (1992) 216: 29-39.

(56) References Cited

OTHER PUBLICATIONS

Harding et al., "Rapid isolation of DNA from complex biological samples using a novel capture reagent—methidium-spermine-sepharose", Nucl Acids Res. (1989) 17(17): 6947-6958.
He et al., Microfabricated Filters for Microfluidic Analytical Systems, Analytical Chemistry, American Chemical Society, 1999, vol. 71, No. 7, pp. 1464-1468.
Heid et al., "Genome Methods—Real Time Quantitative PCR", Genome Res. (1996) 6(10):986-994.
Henry C.S. [Ed], "Microchip Capillary electrophoresis", Methods in Molecular Biology, Humana Press 339 (2006) Parts I-IV in 250 pages.
Herr et al., "Investigation of a miniaturized capillary isoelectric focusing (cIEF) system using a full-field detection approach", Solid State Sensor and Actuator Workshop, Hilton Head Island (2000), pp. 4-8.
Herr et al., "Miniaturized Isoelectric Focusing (µIEF) As a Component of a Multi-Dimensional Microfluidic System", Micro Total Analysis Systems (2001) pp. 51-53.
Herr et al., Miniaturized Capillary Isoelectric Focusing (cIEF): Towards a Portable High-Speed Separation Method. In Micro Total Analysis Systems (2000) Springer, Dordrecht; pp. 367-370.
Holland et al., "Point-of-care molecular diagnostic systems—past, present and future", Curr Opin Microbiol. (2005) 8(5):504-509.
Hong et al., "Integrated nanoliter systems", Nat Biotechnol. (2003) 21(10):1179-1183.
Hong et al., "Molecular biology on a microfluidic chip", J Phys.: Condens Matter (2006) 18(18):S691-S701.
Hong et al., "Integrated Nucleic Acid Analysis in Parallel Matrix Architecture", in Integrated Biochips for DNA Analysis by Liu et al. [Eds], (2007) Chapter 8, pp. 107-116.
Horsman et al., "Forensic DNA Analysis on Microfluidic Devices: A Review", J Forensic Sci. (2007) 52(4):784-799.
Hsieh et al.,"Enhancement of thermal uniformity for a microthermal cycler and its application for polymerase chain reaction", Sens Actuators B: Chemical. (2008) 130(2):848-856.
Huang et al., "Temperature Uniformity and DNA Amplification Efficiency in Micromachined Glass PCR Chip", TechConnect Briefs; Tech Proc. Of the 2005 NSTI Nanotechnology Conference and Trade Show. (2005) vol. 1:452-455.
Huebner et al., "Microdroplets: A sea of applications?", Lab Chip. (2008) 8(8):1244-1254.
Ibrahim, et al., Real-Time Microchip PCR for Detecting Single-Base Differences in Viral and Human DNA, Analytical Chemistry, American Chemical Society, 1998, 70(9): 2013-2017.
International Preliminary Report on Patentability and Written Opinion dated Jan. 19, 2010 for Application No. PCT/US2008/008640, filed Jul. 14, 2008.
International Preliminary Report on Patentability dated Jan. 19, 2010 for Application No. PCT/US2008/069897, filed Jul. 11, 2008.
International Search Report and Written Opinion dated Apr. 4, 2008 for PCT/US2007/007513, filed Mar. 26, 2007.
International Search Report and Written Opinion dated Jan. 5, 2009 for PCT/US2007/024022, filed Nov. 14, 2007.
International Search Report and Written Opinion, dated Oct. 3, 2008, issued in International Application No. PCT/US2008/069897, filed Jul. 11, 2008.
International Search Report dated Jun. 17, 2009 for Application No. PCT/US2008/008640, filed Jul. 14, 2008.
Iordanov et al., "PCR Array on Chip—Thermal Characterization", IEEE Sensors (2003) Conference Oct. 22-24, 2003; pp. 1045-1048.
Irawan et al., "Cross-Talk Problem on a Fluorescence Multi-Channel Microfluidic Chip System," Biomed Micro. (2005) 7(3):205-211.
Ji et al., "DNA Purification Silicon Chip", Sensors and Actuators A: Physical (2007) 139(1-2):139-144.
Jia et al., "A low-cost, disposable card for rapid polymerase chain reaction", Colloids Surfaces B: Biointerfaces (2007) 58:52-60.

Kaigala et al., "An inexpensive and portable microchip-based platform for integrated RT-PCR and capillary electrophoresis", The Analyst (2008) 133(3):331-338.
Kajiyama et al., "Genotyping on a Thermal Gradient DNA Chip", Genome Res. (2003) 13(3):467-475.
Kang et al., "Simulation and Optimization of a Flow-Through Micro PCR Chip", NSTI-Nanotech (2006) vol. 2, pp. 585-588.
Kantak et al.,"Microfluidic platelet function analyzer for shear-induced platelet activation studies", 2nd Annual International IEEE-EMBS Special Topic Conference on Microtechnologies in Med and Biol. (May 2002) 5 pages.
Kantak et al., "Microfabricated cyclical electrical field flow fractionation", 7th International Conference on Miniaturized Chomical and Biochem Analysis Sys. (2003) pp. 1199-1202.
Kantak et al., "Platelet function analyzer: Shear activation of platelets in microchannels", Biomedical Microdevices (2003) 5(3):207-215.
Kantak et al., "Characterization of a microscale cyclical electrical field flow fractionation system", Lab Chip. (2006) 6(5):645-654.
Kantak et al., "Effect of carrier ionic strength in microscale cyclical electrical field-flow fractionation", Anal Chem. (2006) 78(8):2557-2564.
Kantak et al., "Improved theory of cyclical electrical field flow fractions", Electrophoresis (2006) 27(14):2833-2843.
Karunasiri et al.,"Extraction of thermal parameters of microbolometer infrared detectors using electrical measurement", SPIE's Inter'l Symposium on Optical Science, Engineering, and Instrumentation; Proceedings (1998) vol. 3436, Infrared Technology and Applications XXIV; (1998) 8 pages.
Kelly et al., "Microfluidic Systems for Integrated, High-Throughput DNA Analysis," Analytical Chemistry, (2005), 97A-102A, Mar. 1, 2005, in 7 pages.
Khandurina et al., Microfabricated Porous Membrane Structure for Sample Concentration and Electrophoretic Analysis, Analytical Chemistry American Chemical Society, 1999, 71(9): 1815-1819.
Khandurina et al., "Bioanalysis in microfluidic devices," J Chromatography A, (2002) 943:159-183.
Kim et al., "Reduction of Microfluidic End Effects In Micro-Field Flow Fractionation Channels", Proc. MicroTAS 2003, pp. 5-9.
Kim et al., "Multi-DNA extraction chip based on an aluminum oxide membrane integrated into a PDMS microfluidic structure", 3rd IEEE/EMBS Special Topic Conference on Microtechnology in Med and Biol. (May 2005).
Kim et al., "Electrohydrodynamic Generation and Delivery of Monodisperse Picoliter Droplets Using a Poly(dimethylsiloxane) Microchip", Anal Chem. (2006) 78: 8011-8019.
Kim et al., "Geometric optimization of a thin film ITO heater to generate a uniform temperature distribution", (2006), Tokyo, Japan; pp. 293-295; Abstract.
Kim et al., "Micro-Raman thermometry for measuring the temperature distribution inside the microchannel of a polymerase chain reaction chip", J Micromech Microeng. (2006) 16(3):526-530.
Kim et al., "Patterning of a Nanoporous Membrane for Multi-sample DNA Extraction", J Micromech Microeng. (2006) 16:33-39.
Kim et al., "Performance evaluation of thermal cyclers for PCR in a rapid cycling condition", Biotechniques. (2008) 44(4):495-505.
Kim et al., "Quantitative and qualitative analysis of a microfluidic DNA extraction system using a nanoporous AlO(x) membrane", Lab Chip. (2008) 8(9):1516-1523.
Kogi et al., "Microinjection-microspectroscopy of single oil droplets in water: an application to liquid/liquid extraction under solution-flow conditions", Anal Chim Acta. (2000) 418(2):129-135.
Kopf-Sill et al., "Creating a Lab-on-a-Chip with Microfluidic Technologies", in Integrated Microfabricated Biodevices: Advanced Technologies for Genomics, Drug Discovery, Bioanalysis, and Clinical Diagnostics (2002) Chapter 2; pp. 35-54.
Kopp et al., Chemical Amplification: Continuous-Flow PCR on a Chip, www.sciencemag.org, 1998, vol. 280, pp. 1046-1048.
Kricka L.J., "Microchips, Bioelectronic Chips, and Gene Chips—Microanalyzers for the Next Century", in Biochip Technology by Cheng et al. [Eds]; (2006) Chapter 1, pp. 1-16.

(56) References Cited

OTHER PUBLICATIONS

Krishnan et al., "Polymerase chain reaction in high surface-to-volume ratio SiO2 microstructures", Anal Chem. (2004) 76(22):6588-6593.
Kuo et al., "Remnant cationic dendrimers block RNA migration in electrophoresis after monophasic lysis", J Biotech. (2007) 129: 383-390.
Kuswandi et al., "Optical sensing systems for microfluidic devices: a review", Anal Chim Acta. (2007) 601(2):141-155.
Kutter et al., Solid Phase Extraction on Microfluidic Devices, J. Microcolumn Separations, John Wiley & Sons, Inc., 2000, 12(2): 93-97.
LABCHEM; Sodium Hydroxide, 0,5N (0.5M); Safety Data Sheet, 2015; 8 pages.
Lagally et al., Single-Molecule DNA Amplification and Analysis in an Integrated Microfluidic Device, Analytical Chemistry, American Chemical Society, 2001, 73(3): 565-570.
Lagally et al., "Genetic Analysis Using Portable PCR-CE Microsystem", Proceedings 7th International Conference on Miniaturized Chemical and Biochemical Analysis Systems (2003) pp. 1283-1286.
Lagally et al., "Integrated portable genetic analysis microsystem for pathogen/infectious disease detection", Anal Chem. (2004) 76(11):3152-3170.
Lauerman L.H., "Advances in PCR technology", Anim Health Res Rev. (2004) 5(2):247-248.
Lawyer et al., "High-level Expression, Purification, and Enzymatic Characterization of Full-length Thermus aquaticus DNA Polymerase and a Truncated Form Deficient in 5'to 3'Exonuclease Activity." Genome research (1993) 2(4):275-287.
Lee et al., "Submicroliter-volume PCR chip with fast thermal response and very power consumption", 7th International Conference on Miniaturized Chemical and Biochemical Analysis Systems, (2003) pp. 187-190.
Lee et al., "Bulk-micromachined submicroliter-volume PCR chip with very rapid thermal response and low power consumption", Lab Chip. (2004) 4(4):401-407.
Lewin et al., "Use of Real-Time PCR and Molecular Beacons to Detect Virus Replication in Human Immunodeficiency Virus Type 1-infected Individuals on Prolonged Effective Antiretroviral Therapy". J Virol. (1999) 73(7), 6099-6103.
Li et al., "Effect of high-aspect-ratio microstructures on cell growth and attachment", 1st Annual Inter'l IEEE-EMBS Special Topic Conference on Microtechnologies in Med and Biol. Proceedings Cat. No.00EX451; (Oct. 2000) Poster 66, pp. 531-536.
Li PCH., "Micromachining Methods et al." in Microfluidic Lab-on-a-Chip for Chemical and Biological Analysis and Discovery, CRC Press (2005), Chapter 2-3 to 2-5; pp. 10-49.
Li PCH., "Microfluidic Flow" in Microfluidic Lab-on-a-Chip for Chemical and Biological Analysis and Discovery, CRC Press (2005), Chapter 3, pp. 55-99.
Li PCH., "Detection Methods" in Microfluidic Lab-on-a-Chip for Chemical and Biological Analysis and Discovery, CRC Press (2005), Chapter 7, pp. 187-249.
Li PCH., "Applications to Nucleic Acids Analysis" in Microfluidic Lab-on-a-Chip for Chemical and Biological Analysis and Discovery, CRC Press (2005), Chapter 9; pp. 293-325.
Li et al., "A Continuous-Flow Polymerase Chain Reaction Microchip With Regional Velocity Control", J Microelectromech Syst. (2006) 15(1):223-236.
Liao et al., "Miniature RT-PCR system for diagnosis of RNA-based viruses," Nucl Acids Res. (2005) 33(18):e156 in 7 pages.
Lien et al., "Integrated reverse transcription polymerase chain reaction systems for virus detection", Biosens Bioelectron. (2007) 22(8):1739-1748.
Lien et al., "Microfluidic Systems Integrated with a Sample Pretreatment Device for Fast Nucleic-Acid Amplification", J Microelectro Sys. (2008) 17(2):288-301.
Lifesciences et al., "Microfluidics in commercial applications; an industry perspective." Lab Chip (2006) 6:1118-1121.

Lin et al., "Thermal Uniformity of 12-in Silicon Wafer During Rapid Thermal Processing by Inverse Heat Transfer Method," IEEE Transactions on Semiconductor Manufacturing, (2000) 13(4):448-456.
Lin et al., "Simulation and experimental validation of micro polymerase chain reaction chips", Sens Actuators B: Chemical. (2000) 71(1-2):127-133.
Linder et al., "Microfluidics at the Crossroad with Point-of-care Diagnostics", Analyst (2007) 132:1186-1192.
Liu et al., "Integrated portable polymerase chain reaction-capillary electrophoresis microsystem for rapid forensic short tandem repeat typing", Anal Chem. (2007) 79(5):1881-1889.
Liu et al. [Eds], Integrated Biochips for DNA Analysis—Biotechnology Intelligence Unit; Springer/Landes Bioscience (2007) ISBN:978-0-387-76758-1; 216 pages.
Livache et al., "Polypyrrole DNA chip on a Silicon Device: Example of Hepatitis C Virus Genotyping", Analytical Biochemistry, (1998) 255: 188-194.
Locascio et al., "ANYL 67 Award Address—Microfluidics as a tool to enable research and discovery in the life sciences", Abstract; The 236th ACS National Meeting (Aug. 2008); 2 pages.
Mahjoob et al., "Rapid microfluidic thermal cycler for polymerase chain reaction nucleic acid amplification", Inter'l J Heat Mass Transfer. (2008) 51(9-10):2109-2122.
Malitson, "Interspecimen Comparison of the Refractive Index of Fused Silica," J Optical Society of America, 55:1205-1209 (1965).
Manz et al., "Miniaturized Total Chemical Analysis Systems: a Novel Concept for Chemical Sensing," Sensors and Actuators B1, (1990) 244-248.
Marcus et al., "Parallel picoliter rt-PCR assays using microfluidics", Anal Chem. (2006) 78(3):956-958.
Mariella R.P. Jr., "Microtechnology", Thrust Area Report FY 96 UCRL-ID-125472; Lawrence Livermore National Lab., CA (Feb. 1997) Chapter 3 in 44 pages.
Mariella R., "Sample preparation: the weak link in microfluidics-based biodetection", Biomed Microdevices. (2008) 10(6):777-784.
Mastrangelo et al., Microfabricated Devices for Genetic Diagnostics. Proceedings of the IEEE (1998) 86(8):1769-1787.
Mascini et al., "DNA electrochemical biosensors", Fresenius J. Anal. Chem., 369: 15-22, (2001).
McMillan et al., "Application of advanced microfluidics and rapid PCR to analysis of microbial targets", In Proceedings of the 8th international symposium on microbial ecology (1999), in 13 pages.
Melin et al., "Microfluidic large-scale integration: the evolution of design rules for biological automation", Annu Rev Biophys Biomol Struct. (2007) 36:213-231.
Merugu et al., "High Throughput Separations Using a Microfabricated Serial Electric Split Ssystem" (2003), Proceedings of µTAS 2003, 7th International Conference on Miniaturized Chemical and Biochemical Analysis Systems, Oct. 5-9, 2003, Squaw Valley, California; 1191-1194, in 3 pages.
Meyers, R.A., Molecular Biology and Biotechnology: A Comprehensive Desk Reference; VCH Publishers, Inc. New York, NY; (1995) pp. 418-419.
Miao et al., "Low cost micro-PCR array and micro-fluidic integration on single silicon chip", Int'l J Comput Eng Science (2003) 4(2):231-234.
Miao et al., "Flip-Chip packaged micro-plate for low cost thermal multiplexing", Int'l J Comput Eng Science. (2003) 4(2):235-238.
Micheletti et al., "Microscale Bioprocess Optimisation", Curr Opin Biotech. (2006) 17:611-618.
MicroTAS 2005., "Micro Total Analysis Systems", Proceedings 9th Int. Conference on Miniaturized Systems for Chemistry and Life Sciences; Presentations/Posters/Articles for Conference; Boston, MA in Oct. 10-12, 2005 in 1667 pages.
MicroTAS 2007., "Micro Total Analysis Systems", Proceedings 11th Int. Conference on Miniaturized Systems for Chemistry and Life Sciences; Presentations/Posters/Articles for Conference; Paris, France in Oct. 7-11, 2007 in 1948 pages.
MicroTAS 2007., "Micro Total Analysis Systems", Advance Program for the Proceedings 11th Int. Conference on Miniaturized

(56) References Cited

OTHER PUBLICATIONS

Systems for Chemistry and Life Sciences; Presentations/Posters/Articles for Conference; Paris, France in Oct. 7-11, 2007 in 42 pages.
Minco, "Conductive Heating Technologies for Medical Diagnostic Equipment," (2006) in 13 pages.
Mitchell et al., "Modeling and validation of a molded polycarbonate continuous-flow polymerase chain reaction device," Microfluidics, BioMEMS, and Medical Microsystems, Proc. SPIE (2003) 4982:83-98.
Myers et al., "Innovations in optical microfluidic technologies for point-of-care diagnostics", Lab Chip (2008) 8:2015-2031.
Nakagawa et al., Fabrication of amino silane-coated microchip for DNA extraction from whole blood, J of Biotechnology, Mar. 2, 2005, 116:105-111.
Namasivayam et al., "Advances in on-chip photodetection for applications in miniaturized genetic analysis systems", J Micromech Microeng. (2004) 14:81-90.
Narayanan et al., "A microfabricated electrical SPLITT system," Lab Chip, (2006) 6:105-114.
Neuzil et al., "Disposable real-time microPCR device: lab-on-a-chip at a low cost," Mol. Biosyst., (2006) 2:292-298.
Neuzil et al., "Ultra fast miniaturized real-time PCR: 40 cycles in less than six minutes," Nucleic Acids Research, (2006) 34(11)e77, in 9 pages.
Nguyen et al. [Eds], "Microfluidics for Internal Flow Control: Microfluidics" in Fundamentals and Applications of Microfluidics; 2nd Edition (2006) Introduction Chapter 1, pp. 1-9.
Nguyen et al. [Eds], "Microfluidics for Internal Flow Control: Microvalves" in Fundamentals and Applications of Microfluidics; (2006) 2nd Edition, Chapter 6, pp. 211-254.
Nguyen et al. [Eds], "Microfluidics for Internal Flow Control: Micropumps" in Fundamentals and Applications of Microfluidics; (2006) 2nd Edition, Chapter 7, pp. 255-309.
Nguyen et al. [Eds], "Microfluidics for Life Sciences and Chemistry: Microdispensers" in Fundamentals and Applications of Microfluidics; (2006), Chapter 11, pp. 395-418.
Nguyen et al. [Eds], "Microfluidics for Life Sciences and Chemistry: Microreactors" in Fundamentals and Applications of Microfluidics; (2006) 2nd Edition, Chapter 13, pp. 443-477.
Ning et al., "Microfabrication Processes for Silicon and Glass Chips", in Biochip Technology, CRC-Press (2006) Chapter 2, pp. 17-38.
Northrup et al., "A MEMs-based Miniature DNA Analysis System," Lawrence Livermore National Laboratory, (1995), submitted to Transducers '95, Stockholm, Sweden, Jun. 25-29, 1995, in 7 pages.
Northrup et al., "Advantages Afforded by Miniaturization and Integration of DNA Analysis Instrumentation," Microreaction Technology, (1998) 278-288.
Northrup et al., A Miniature Analytical Instrument for Nucleic Acids Based on Micromachined Silicon Reaction Chambers, Analytical Chemistry, American Chemical Society, 1998, 70(5): 918-922.
Northrup et al., "A New Generation of PCR Instruments and Nucleic Acid Concentration Systems," in PCR Applications: Protocols for Functional Genomics, (1999), Chapter 8, pp. 105-125.
Northrup, "Microfluidics, A few good tricks," Nature materials (2004), 3:282-283.
Northrup et al.,"Microfluidics-based integrated airborne pathogen detection systems," Abstract, Proceedings of the SPIE, (2006), vol. 6398, Abstract in 2 pages.
Oh et al., "World-to-chip microfluidic interface with built-in valves for multichamber chip-based PCR assays," Lab Chip, (2005), 5:845-850.
Oh K.W. et al., "A Review of Microvalves", J Micromech Microeng. (2006) 16:R13-R39.
Ohno et al., "Microfluidics: Applications for analytical purposes in chemistry and biochemistry," Electrophoresis (2008), 29:4443-4453.
Oleschuk et al., Trapping of Bead-Based Reagents within Microfluidic Systems: On-Chip Solid-Phase Extraction and Electrochromatography, Analytical Chemistry, American Chemical Society, 2000, 72(3): 585-590.
Pal et al., "Phase Change Microvalve for Integrated Devices", Anal Chem. (2004) 76: 3740-3748.
Pal et al., "Phase Change Microvalve for Integrated Devices," Anal. Chem. (2004), 76(13):3740-3748, Jul. 1, 2004, in 9 pages.
Pal et al., "An integrated microfluidic for influenza and other genetic analyses," Lab Chip, (2005), 5:1024-1032.
Palina et al., "Laser Assisted Boron Doping of Silicon Wafer Solar Cells Using Nanosecond and Picosecond Laser Pulses," 2011 37th IEEE Photovoltaic Specialists Conference, pp. 002193-002197, IEEE (2011).
Pamme, "Continuous flow separations in microfluidic devices," Lab Chip, (2007), 7:1644-1659.
Pang et al., "A novel single-chip fabrication technique for three-dimensional MEMS structures," Institute of Microelectronics, Tsinghua University, Beijing, P.R. China, (1998), IEEE, 936-938.
Pang et al., "The Study of Single-Chip Integrated Microfluidic System," Tsinghua University, Beijing, P.R. China, (1998), IEEE, 895-898.
Papautsky et al., "Effects of rectangular microchannel aspect ratio on laminar friction constant", in Microfluidic Devices and Systems II (1999) 3877:147-158.
Paulson et al., "Optical dispersion control in surfactant-free DNA thin films by vitamin B2 doping," Nature, Scientific Reports 8:9358 (2018) published at www.nature.com/scientificreports, Jun. 19, 2018.
Petersen, Kurt E., "Silicon as a Mechanical Material." Proceedings of the IEEE, (May 1982) 70(5):420-457.
Petersen et al., "Toward Next Generation Clinical Diagnostic Instruments: Scaling and New Processing Paradigms," Biomedical Microdevices (1998) 1(1):71-79.
Picard et al., Laboratory Detection of Group B *Streptococcus* for Prevention of Perinatal Disease, Eur. J. Clin. Microbiol. Infect. Dis., Jul. 16, 2004, 23: 665-671.
Plambeck et al., "Electrochemical Studies of Antitumor Antibiotics", J. Electrochem Soc.: Electrochemical Science and Technology (1984), 131(11): 2556-2563.
Poser et al., "Chip elements for fast thermocycling," Sensors and Actuators A, (1997), 62:672-675.
Pourahmadi et al., "Toward a Rapid, Integrated, and Fully Automated DNA Diagnostic Assay for Chlamydia trachomatis and Neisseria gonorrhea," Clinical Chemistry, (2000), 46(9):1511-1513.
Pourahmadi et al., "Versatile, Adaptable and Programmable Microfluidic Platforms for DNA Diagnostics and Drug Discovery Assays," Micro Total Analysis Systems, (2000), 243-248.
Raisi et al., "Microchip isoelectric focusing using a miniature scanning detection system," Electrophoresis, (2001), 22:2291-2295.
Raja et al., "Technology for Automated, Rapid, and Quantitative PCR or Reverse Transcriptin-PCR Clinical Testing," Clinical Chemistry, (2005), 51(5):882-890.
Reyes et al., "Micro Total Analysis Systems. 1. Introduction, Theory, and Technology", Anal Chem (2002) 74:2623-2636.
Roche et al. "Ectodermal commitment of insulin-producing cells derived from mouse embryonic stem cells" Faseb J (2005) 19: 1341-1343.
Rodriguez et al., "Practical integration of polymerase chain reaction amplification and electrophoretic analysis in microfluidic devices for genetic analysis," Electrophoresis, (2003), 24:172-178.
Rohsenow et al. [Eds.], Handbook of Heat Transfer, 3rd Edition McGraw-Hill Publishers (1998) Chapters 1 & 3; pp. 108.
Roper et al., "Advances in Polymer Chain Reaction on Microfluidic Chips," Anal. Chem., (2005), 77:3887-3894.
Ross et al., Analysis of DNA Fragments from Conventional and Microfabricated PCR Devices Using Delayed Extraction MALDI-TOF Mass Spectrometry, Analytical Chemistry, American Chemical Society, 1998, 70(10): 2067-2073.
Ross et al., "Scanning Temperature Gradient Focusing for Simultaneous Concentration and Separation of Complex Samples," Micro Total Analysis Systems 2005, vol. 2, (2005), Proceedings of μTAS

(56) References Cited

OTHER PUBLICATIONS

2005, Ninth International Conference on Miniaturized Systems for Chemistry and Life Sciences, Oct. 9-13, 2005, Boston, Massachusetts; 1022-1024.
Ross et al., "Simple Device for Multiplexed Electrophoretic Separations Using Gradient Elution Moving Boundary Electrophoresis with Channel Current Detection," Anal. Chem., (2008), 80(24):9467-9474.
Sadler et al., "Thermal Management of BioMEMS: Temperature Control for Ceramic-Based PCR and DNA Detection Devices," IEEE Transactions on Components and Packaging Technologies, (2003) 26(2):309-316.
Sanchez et al., "Linear-After-The-Exponential (LATE)-PCR: An advanced method of asymmetric PCR and its uses in quantitative real-time analysis", PNAS (2004) 101(7): 1933-1938.
Sant et al., "An Integrated Optical Detector for Microfabricated Electrical Field Flow Fractionation System," Proceedings of μTAS 2003, 7th International Conference on Miniaturized Chemical and Biochemical Analysis Systems, Oct. 5-9, 2003, Squaw Valley, California; pp. 1259-1262.
Sant et al., "Geometric scaling effects on instrumental plate height in field flow fractionation", J Chromatography A (2006) 1104:282-290.
Sant H.J., "Reduction of End Effect-Induced Zone Broadening in Field-Flow Fractionation Channels", Anl Chem. (2006) 78:7978-7985.
Sant et al., "Microscale Field-Flow Fractionation: Theory and Practice", in Microfluidic Technologies for Miniaturized Analysis Systems. (2007) Chapter 12, pp. 4710521.
Schäferling et al., "Optical technologies for the read out and quality control of DNA and protein microarrays," Anal Bioanal Chem, (2006), 385: 500-517.
Serpengüzel et al., "Microdroplet identification and size measurement in sprays with lasing images", Optics express (2002) 10(20):1118-1132.
Shackman et al., "Gradient Elution Moving Boundary Electrophoresis for High-Throughput Multiplexed Microfluidic Devices," Anal. Chem. (2007), 79(2), 565-571.
Shackman et al., "Temperature gradient focusing for microchannel separations," Anal Bioanal Chem, (2007), 387:155-158.
Shadpour et al., "Multichannel Microchip Electrophoresis Device Fabricated in Polycarbonate with an Integrated Contact Conductivity Sensor Array," Anal Chem., (2007), 79(3), 870-878.
Shen et al., "A microchip-based PCR device using flexible printed circuit technology," Sensors and Actuators B (2005), 105:251-258.
Shoffner et al., Chip PCR.I. Surface Passivation of Microfabricated Silicon-Glass Chips for PCR, Nucleic Acids Research, Oxford University Press, (1996) 24(2): 375-379.
Sia et al., "Microfluidic devices fabricated in poly(dimethylsiloxane) for biological studies," Electrophoresis, (2003), 24:3563-3576.
Sigurdson M., "AC Electrokinetic Enhancement for Assay Enhancement", ProQuest LLC (2008) Doctoral Thesis UMI Microform 3319791 in 24 pages.
Singh et al., "PCR thermal management in an integrated Lab on Chip," Journal of Physics: Conference Series, (2006), 34:222-227.
Situma et al., "Merging microfluidics with microarray-based bioassays", Biomol Engin. (2006) 23:213-231.
Smith, K. et al., "Comparison of Commercial DNA Extraction Kits for Extraction of Bacterial Genomic DNA from Whole-Blood Samples", Journal of Clinical Microbiology, vol. 41, No. 6 (Jun. 2003), pp. 2440-2443.
Smith et al., "(576d) Micropatterned fluid lipid bilayers created using a continuous flow microspotter for multi-analyte assays," (2007), Biosensors II, 2007 AIChE Annual Meeting, Nov. 8, 2007, Abstract in 2 pages.
Sommer et al., "Introduction to Microfluidics", in Microfluidics for Biological Applications by Tian et al. [Eds] (2008) Chapter 1, pp. 1-34.
Spitzack et al., "Polymerase Chain Reaction in Miniaturized Systems: Big Progress in Little Devices", in Methods in Molecular Biology—Microfluidic Techniques, Minteer S.D. [Ed.] Humana Press (2006), Chapter 10, pp. 97-129.
Squires et al., "Microfluidics: Fluid physics at the nanoliter scale", Rev Modern Phys. (2005) 77(3):977-1026.
Sundberg et al., "Solution-phase DNA mutation scanning and SNP genotyping by nanoliter melting analysis," Biomed Microdevices, (2007), 9:159-166, in 8 pages.
Supplemental European Search Report dated Jun. 4, 2010 for Application No. 02761632.5, filed Sep. 12, 2002.
Supplementary European Search dated Jan. 10, 2008 for European Patent Application No. 05745564, filed May 3, 2005.
Supplementary European Search Report dated Jun. 3, 2005 for European Patent Application No. 02723636.3, filed Mar. 27, 2002.
Supplementary European Search Report dated May 3, 2010 for European Patent Application No. 02715213.1, filed Mar. 27, 2002.
Tabeling, P. [Ed.], "Physics at the micrometric scale," in Introduction to Microfluidics (2005) Chapter 1, pp. 24-69.
Tabeling, P. [Ed.], "Hydrodynamics of Microfluidic Systems", in Introduction to Microfluidics; (2005) Chapter 2, pp. 70-129.
Tabeling, P. [Ed.], Introduction to Microfluidics; (2005) Chapters 5-7, pp. 216-297.
Tanaka et al., "Improved Method of DNA Extraction from Seeds Using Amine-Dendrimer Modified Magnetic Particles", Proceedings of the 74th Annual Meeting of the Electrochemical Society of Japan; Abstract #2E09 on p. 149, Mar. 29, 2007; Faculty of Engineering, Science University of Tokyo; 4 pages.
Taylor et al., Fully Automated Sample Preparation for Pathogen Detection Performed in a Microfluidic Cassette, in Micro Total Analysis Systems, Springer (2001), pp. 670-672.
Taylor et al., "Lysing Bacterial Spores by Sonication through a Flexible Interface in a Microfluidic System," Anal. Chem., (2001), 73(3):492-496.
Taylor et al., "Microfluidic Bioanalysis Cartridge with Interchangeable Microchannel Separation Components," (2001), The 11th International Conference on Solid-State Sensors and Actuators, Jun. 10-14, 2001, Munich, Germany; 1214-1247.
Taylor et al., "Disrupting Bacterial Spores and Cells using Ultrasound Applied through a Solid Interface," (2002), 2nd Annual International IEEE-EMBS Special Topic Conference on Microtechnologies in Medicine & Biology, May 2-4, 2002, Madison, Wisconsin: 551-555.
Thorsen et al., "Microfluidic Large-scale integration," Science, (2002), 298:580-584.
Toriello et al., "Multichannel Reverse Transcription-Polymerase Chain Reaction Microdevice for Rapid Gene Expression and Biomarker Analysis," Anal. Chem., (2006) 78(23):7997-8003.
Ugaz et al., "Microfabricated electrophoresis systems for DNA sequencing and genotyping applications," Phil. Trans. R. Soc. Lond. A, (2004), 362:1105-1129.
Ugaz et al., "PCR in Integrated Microfluidic Systems", in Integrated Biochips for DNA Analysis by Liu et al. [Eds]; (2007) Chapter 7, pp. 90-106.
Ullman et al., "Luminescent oxygen channeling assay (LOCI™): sensitive, broadly applicable homogeneous immunoassay method". Clin Chem. (1996) 42(9), 1518-1526.
Velten et al., "Packaging of Bio-MEMS: Strategies, Technologies, and Applications," IEEE Transactions on Advanced Packaging, (2005) 28(4):533-546.
Vinet et al., "Microarrays and microfluidic devices: miniaturized systems for biological analysis," Microelectronic Engineering, (2002), 61-62:41-47.
Wang, "Survey and Summary, from DNA Biosensors to Gene Chips", Nucleic Acids Research, 28(16):3011-3016, (2000).
Wang et al., "From biochips to laboratory-on-a-chip system", in Genomic Signal Processing and Statistics by Dougherty et al. [Eds]; (2005) Chapter 5, pp. 163-200.
Wang et al., "A disposable microfluidic cassette for DNA amplification and detection", Lab on a Chip (2006) 6(1):46-53.
Wang et al., "Micromachined Flow-through Polymerase Chain Reaction Chip Utilizing Multiple Membrane-activated Micropumps," (2006), MEMS 2006, Jan. 22-26, 2006, Istanbul, Turkey; 374-377.

(56) References Cited

OTHER PUBLICATIONS

Waters et al., Microchip Device for Cell Lysis, Multiplex PCR Amplification, and Electrophoretic Sizing, Analytical Chemistry, American Chemical Society, 1998, 70(1): 158-162.
Weigl, et al., Microfluidic Diffusion-Based Separation and Detection, www.sciencemag.org, 1999, vol. 283, pp. 346-347.
Woolley A.T., "Integrating Sample Processing and Detection with Microchip Capillary Electrophoresis of DNA", in Integrated Biochips for DNA Analysis by Liu et al. [Eds]; (2007) Chapter 5, pp. 68-77.
Wu et al., "Polycationic dendrimers interact with RNA molecules: polyamine dendrimers inhibit the catalytic activity of Candida ribozymes", Chem Commun. (2005) 3: 313-315.
Xiang et al., "Real Time PCR on Disposable PDMS Chip with a Miniaturized Thermal Cycler," Biomedical Microdevices, (2005), 7(4):273-279.
Xuan, "Joule heating in electrokinetic flow," Electrophoresis, (2008), 298:33-43.
Yang et al., "High sensitivity PCR assay in plastic micro reactors," Lab Chip, (2002), 2:179-187.
Yang et al., "An independent, temperature controllable-microelectrode array," Anal. Chem., (2004), 76(5):1537-1543.
Yang et al., "Cost-effective thermal isolation techniques for use on microfabricated DNA amplification and analysis devices," J Micromech Microeng, (2005), 15:221-230.
Yobas et al., Microfluidic Chips for Viral RNA Extraction & Detection, (2005), 2005 IEEE, 49-52.
Yobas et al., "Nucleic Acid Extraction, Amplification, and Detection on Si-Based Microfluidic Platforms," IEEE Journal of Solid-State Circuits, (2007), 42(8):1803-1813.
Yoon et al., "Precise temperature control and rapid thermal cycling in a micromachined DNA polymer chain reaction chip," J. Micromech. Microeng., (2002), 12:813-823.
Yoza et al., "Fully Automated DNA Extraction from Blood Using Magnetic Particles Modified with a Hyperbranched Polyamidoamine Dendrimer", J Biosci Bioeng, 2003, 95(1): 21-26.
Yoza et al., DNA extraction using bacterial magnetic particles modified with hyperbranched polyamidoamine dendrimer, J Biotechnol., Mar. 20, 2003, 101(3): 219-228.
Zhang et al., "Temperature analysis of continuous-flow micro-PCR based on FEA," Sensors and Actuators B, (2002), 82:75-81.
Zhang et al., "PCR Microfluidic Devices for DNA Amplification," Biotechnology Advances, 24:243-284 (2006).
Zhang et al, "Continuous-Flow PCR Microfluidics for Rapid DNA Amplification Using Thin Film Heater with Low Thermal Mass," Analytical Letters, (2007), 40:1672-1685, in 15 pages.
Zhang et al, "Direct Adsorption and Detection of Proteins, Including Ferritin, onto Microlens Array Patterned Bioarrays," J Am Chem Soc., (2007), 129:9252-9253.
Zhang et al, "Micropumps, microvalves, and micromixers within PCR microfluidic chips: Advances and trens," Biotechnology Advances, (2007), 25:483-514.
Zhang et al., "Miniaturized PCR chips for nucleic acid amplification and analysis: latest advances and future trends," Nucl Acids Res., (2007) 35(13):4223-4237.
Zhao et al, "Heat properties of an integrated micro PCR vessel," Proceedings of SPIE, (2001), International Conference on Sensor Technology, 4414:31-34.
Zhou et al., "Cooperative binding and self-assembling behavior of cationic low molecular-weight dendrons with RNA molecules", Org Biomol Chem. (2006) 4(3): 581-585.
Zhou et al., "PAMAM dendrimers for efficient siRNA delivery and potent gene silencing", Chem Comm. (Camb.) (2006) 22: 2362-2364.
Zou et al., "A Micromachined Integratable Thermal Reactor," technical digest from International Electron Devices Meeting, IEEE, Washington, D.C., Dec. 2-5, 2001 (6 pages).
Zou et al., "Micro-assembled multi-chamber thermal cycler for low-cost reaction chip thermal multiplexing," Sensors and Actuators A, (2002), 102:114-121.
Zou et al., "Miniaturized Independently Controllable Multichamber Thermal Cycler," IEEE Sensors Journal, (2003), 3(6):774-780.
Petition for Inter Partes Review of U.S. Pat. No. 7,998,708 (Paper 1 in IPR2019-00488) dated Dec. 20, 2018 (94 pages).
Declaration of Bruce K. Gale, Ph.D. (Exhibit 1001 in IPR2019-00488 and IPR2019-00490) dated Dec. 20, 2018 (235 pages).
Patent Owner Preliminary Response to Petition for Inter Partes Review of U.S. Pat. No. 7,998,708 and Exhibit List (Papers 5 and 6 in IPR2019-00488) dated Apr. 18, 2019 (79 pages).
Decision instituting Inter Partes Review of U.S. Pat. No. 7,998,708 (Paper 8 in IPR2019-00488) dated Jul. 16, 2019 (20 pages).
Petition for Inter Partes Review of U.S. Pat. No. 8,323,900 (Paper 1 in IPR2019-00490) dated Dec. 20, 2018 (85 pages).
Declaration of Michael G. Mauk, Ph.D. in Support of Patent Owner Preliminary Responses in IPR2019-00488 and IPR2019-00490 dated Apr. 18, 2019 (43 pages).
Patent Owner Preliminary Response to Petition for Inter Partes Review of U.S. Pat. No. 8,323,900 and Exhibit List (Papers 5 and 6 in IPR2019-00490) dated Apr. 18, 2019 (73 pages).
Decision instituting Inter Partes Review of U.S. Pat. No. 8,323,900 (Paper 8 in IPR2019-00490) dated Jul. 16, 2019 (23 pages).
Patent Owner's Response in Inter Partes Review of U.S. Pat. No. 8,323,900 and Exhibit List (Paper 25 in IPR2019-00490) dated Oct. 16, 2019 (80 pages).
Patent Owner's Response in Inter Partes Review of U.S. Pat. No. 7,998,708 and Exhibit List (Paper 25 in IPR 2019-00488) dated Oct. 16, 2019 (93 pages).
Transcript of Deposition of Bruce K. Gale, Ph.D., in Support of Patent Owner's Responses (Exhibit 2012 in IPR2019-00488 and IPR2019-00490), taken Sep. 24, 2019 (124 pages).
Declaration of M. Allen Northrup, Ph.D. in Support of Patent Owner's Responses (Exhibit 2036 in IPR2019-00488 and IPR2019-00490) dated Oct. 16, 2019 (365 pages).
Petitioner's Reply to Patent Owner's Response to Petition in Inter Partes Review of U.S. Pat. No. 7,998,708 and Exhibit List (Paper 32 in IPR 2019-00488) dated Jan. 31, 2020 (34 pages).
Petitioner's Reply to Patent Owner's Response to Petition in Inter Partes Review of U.S. Pat. No. 8,323,900 and Exhibit List (Paper 32 in IPR 2019-00490) dated Jan. 31, 2020 (35 pages).
Second Declaration of Bruce K. Gale, Ph.D. (Exhibit 1026 in IPR2019-00488 and IPR2019-00490) dated Jan. 31, 2020 (91 pages).
Transcript of Deposition of M. Allen Northrup, Ph.D., (Exhibit 1027 in IPR2019-00488 and IPR2019-00490), taken Dec. 19, 2019 (109 pages).
Patent Owner's Sur-Reply in Inter Partes Review of U.S. Pat. No. 8,323,900 (Paper 42 in IPR2019-00490) dated Mar. 12, 2020 (39 pages).
Patent Owner's Sur-Reply in Inter Partes Review of U.S. Pat. No. 7,998,708 (Paper 43 in IPR 2019-00488) dated Mar. 12, 2020 (41 pages).
Transcript of Second Deposition of Bruce K. Gale, Ph.D., (Exhibit 2068 in IPR2019-00488 and IPR2019-00490), taken Feb. 19, 2020 (352 pages).
Complaint filed by Becton, *Dickinson et al.,* v. *NeuModx Molecular, Inc.* on Jun. 18, 2019 in U.S. District Court, Delaware, Case #1:19-cv-01126-LPS, Infringement Action involving U.S. Pat. Nos. 7,998,708; 8,273,308; 8,323,900; 8,415,103; 8,703,069; and 8,709,787 (29 pages).
Answer to Complaint filed by NeuModx Molecular, Inc. on Aug. 9, 2019 in U.S. District Court, Delaware, Case #1:19-cv-01126-LPS (24 pages).
Amended Answer to Complaint filed by NeuModx Molecular, Inc. on Oct. 4, 2019 in U.S. District Court, Delaware, Case #1:19-cv-01126-LPS (31 pages).
Anderson et al., "Microfluidic biochemical analysis system" Proc. 1997 IEEE Int. Conf. Solid-State Sens. Actuat., 1997, pp. 477-480.
Anderson et al., "Advances in Integrated Genetic Analysis" Micro Total Analysis Systems '98 Conference Proceedings, D. Kluwer Academic Publishers, 1998, in 6 pages.
Anderson et al., "A Miniature Integrated Device for Automated Multistep Genetic Assays" Nucleic Acids Research (2000) 28(12), i-vi.

(56) References Cited

OTHER PUBLICATIONS

Burns et al., "Microfabricated Structures for Integrated DNA Analysis" Proc. Natl. Acad. Sci. USA (May 1996) 93: 5556-5561.
Harrison et al., "Capillary Electrophoresis and Sample Injection Systems Integrated on a Planar Glass Chip", Anal. Chem. (1992) 64: 1926-1932.
Hsueh et al., "A microfabricated, electrochemiluminescence cell for the detection of amplified DNA" Proc. 1995 IEEE Int. Conf. Solid-State Sens. Actuators, 1995, pp. 768-771.
Hsueh et al., "DNA quantification with an electrochemiluminescence microcell" Proc. 1997 IEEE Int. Conf. Solid-State Sens. Actuators, 1997, pp. 175-178.
Jiang et al., "Directing cell migration with asymmetric micropatterns" Proc. Natl. Acad. Sci. USA. (2005) 102, 975-978.
Lagally et al., "Monolithic integrated microfluidic DNA amplification and capillary electrophoresis analysis system" Sens Actuator B—Chem (2000) 63:138-146.
Manz et al., "Design of an open-tubular column liquid chromatograph using silicon chip technology" Sensors and Actuators B: Chemical (1990) 1:249-255.
Manz et al., "Planar chips technology for miniaturization and integration of separation techniques into monitoring systems: Capillary electrophoresis on a chip" Journal of Chromatography A (1992) 593:253-258.
Rhee et al., "Drop Mixing in a Microchannel for Lab-on-a-Chip Applications" Langmuir, (2008) 24 (2): 590-601.
Sammarco et al., "Thermocapillary Pumping of Discrete Drops in Microfabricated Analysis Devices" AIChE Journal, (1999) 45(2): 350-366.
Taylor et al., "Optimization of the performance of the polymerase chain reaction in silicon-based microstructures" Nucleic Acids Res., 1997, vol. 25, pp. 3164-3168.
Terry et al., "A Gas Chromatographic Air Analyzer Fabricated on a Silicon Wafer" IEEE T Electron Dev (1979) 26:1880-1886.
Whitesides G.M., "The origins and the future of microfluidics" Nature (2006) 442(7101):368-373.
Woias P., "Micropumps—past, progress and future prospects" Sens. Actuators, B. (2005) 105, 28-38.
Woolley et al., "Functional integration of PCR amplification and capillary electrophoresis in a microfabricated DNA analysis device" Anal. Chem., 1996, vol. 68, pp. 4081-4086.
Wu et al., "Fabrication of Complex Three-dimensional Microchannel Systems in PDMS" J. Am. Chem. Soc. (2003) 125, 554-559.
Record of Oral Hearing in IPR2019-00488 and IPR2019-00490 held Apr. 21, 2020 in 80 pages; Petitioner's Demonstratives for Oral Hearing in IPR2019-00488 and IPR2019-00490 held Apr. 21, 2020 in 72 pages; Patent Owner's Demonstratives for Oral Hearing in IPR2019-00488 and IPR2019-00490 held Apr. 21, 2020 in 88 pages; Patent Owner's Objections to Petitioner's Oral Hearing Demonstratives in IPR2019-00488 and IPR2019-00490 dated Apr. 16, 2020 (4 pages).
Petition for Inter Partes Review of U.S. Pat. No. 8,273,308 (Paper 2 in IPR2020-01083) dated Jun. 12, 2020 (104 pages).
Petition for Inter Partes Review of U.S. Pat. No. 8,273,308 (Paper 2 in IPR2020-01091) dated Jun. 12, 2020 (105 pages).
Petition for Inter Partes Review of U.S. Pat. No. 8,803,069 (Paper 2 in IPR2020-01095) dated Jun. 12, 2020 (84 pages).
Petition for Inter Partes Review of U.S. Pat. No. 8,803,069 (Paper 3 in IPR2020-01100) dated Jun. 12, 2020 (83 pages).
Declaration of Mark A. Burns, Ph.D. (Exhibit N1001 in IPR2020-01083, IPR2020-01091, IPR2020-01095 and IPR2020-01100) dated Jun. 12, 2020 (378 pages).
Petition for Inter Partes Review of U.S. Pat. No. 8,709,787 (Paper 2 in IPR2020-01132) dated Jun. 18, 2020 (96 pages).
Petition for Inter Partes Review of U.S. Pat. No. 8,415,103 (Paper 2 in IPR2020-01133) dated Jun. 18, 2020 (96 pages).
Declaration of Mark A. Burns, Ph.D. (Exhibit N1101 in IPR2020-01132 and IPR2020-01133) dated Jun. 17, 2020 (253 pages).
Petition for Inter Partes Review of U.S. Pat. No. 8,415,103 (Paper 2 in IPR2020-01136) dated Jun. 19, 2020 (85 pages).
Petition for Inter Partes Review of U.S. Pat. No. 8,709,787 (Paper 2 in IPR2020-01137) dated Jun. 19, 2020 (86 pages).
Declaration of Mark A. Burns, Ph.D. (Exhibit N1210 in IPR2020-01136 and IPR2020-01137) dated Jun. 19, 2020 (205 pages).
U.S. File History of U.S. Appl. No. 60/491,264, filed Jul. 31, 2003 (50 pages).
U.S. File History of U.S. Appl. No. 60/491,269, filed Jul. 31, 2003 (59 pages).
U.S. File History of U.S. Appl. No. 60/491,539, filed Aug. 1, 2003 (55 pages).
U.S. File History of U.S. Appl. No. 60/553,553, filed Mar. 17, 2004 (59 pages).
U.S. File History of U.S. Appl. No. 60/726,066, filed Oct. 11, 2005 (68 pages).
U.S. File History of U.S. Appl. No. 60/786,007, filed Mar. 24, 2006 (247 pages).
U.S. File History of U.S. Appl. No. 60/859,284, filed Nov. 14, 2006 (121 pages).
Zhang et al., "Parallel DNA amplification by convective polymerase chain reaction with various annealing temperatures on a thermal gradient device," Analytical Biochemistry, (2009) 387:102-112.
Judgment/Final Written Decision Determining No Challenged Claims Unpatentable in Inter Partes Review of U.S. Pat. No. 7,998,708 (Paper No. 52 in IPR2019-00488) dated Jul. 14, 2020 (43 pages).
Judgment/Final Written Decision Determining No Challenged Claims Unpatentable in Inter Partes Review of U.S. Pat. No. 8,323,900 (Paper No. 51 in IPR2019-00490) dated Jul. 14, 2020 (43 pages).
Petitioner's Notice of Appeal in Inter Partes Review of U.S. Pat. No. 7,998,708 (Paper No. 54 in IPR2019-00488) dated Sep. 9, 2020 (48 pages).
Petitioner's Notice of Appeal in Inter Partes Review of U.S. Pat. No. 8,323,900 (Paper No. 53 in IPR2019-00490) dated Sep. 9, 2020 (48 pages).
Patent Owner's Preliminary Response to Petition for Inter Partes Review of U.S. Pat. No. 8,703,069 (Paper 13 in IPR2020-01095) dated Sep. 17, 2020 (77 pages).
Patent Owner's Preliminary Response to Petition for Inter Partes Review of U.S. Pat. No. 8,273,308 (Paper 13 in IPR2020-01091) dated Sep. 17, 2020 (70 pages).
Patent Owner's Preliminary Response to Petition for Inter Partes Review of U.S. Pat. No. 8,703,069 (Paper 14 in IPR2020-01100) dated Sep. 17, 2020 (59 pages).
Declaration of M. Allen Northrup, Ph.D. in Support of Patent Owner Preliminary Responses in IPR2020-01091, IPR2020-01095 and IPR2020-01100 (Exhibit H2003) dated Sep. 16, 2020 (137 pages).
Patent Owner's Preliminary Response to Petition for Inter Partes Review of U.S. Pat. No. 8,273,308 (Paper 13 in IPR2020-01083) dated Oct. 22, 2020 (88 pages).
Declaration of M. Allen Northrup, Ph.D. in support of Patent Owner Preliminary Responses in IPR2020-01083, IPR2020-01091, IPR2020-01095 and IPR2020-01100 (Exhibit H2003) dated Oct. 21, 2020 (171 pages).
First Amended and Supplemental Complaint filed by Becton, Dickinson and Company et al. on Jun. 25, 2020 in U.S. District Court, Delaware, Case #1:19-cv-01126-LPS, Infringement Action involving U.S. Pat. Nos. 7,998,708; 8,273,308; 8,323,900; 8,415,103; 8,703,069; 8,709,787; 10,494,663; 10,364,456; 10,443,088; 10,604,788; 10,625,261; 10,625,262; and 10,632,466 (55 pages).
Answer to First Amended and Supplemental Complaint filed by NeuModx Molecular, Inc. on Jul. 16, 2020 in U.S. District Court, Delaware, Case #1:19-cv-01126-LPS (42 pages).
Defendant NeuModx's Initial Invalidity Contentions filed Sep. 30, 2020 in U.S. District Court, Delaware, Case #1:19-cv-01126-LPS (47 pages).
Northrup et al., "A MEMS-based Miniature DNA Analysis System." Transducers '95—Eurosensors in Proc. 1995 (8th) IEEE Int. Conf. Solid-State Sens. Actuators, pp. 764-767.
Petition for Inter Partes Review of U.S. Pat. No. 10,625,262 (Paper 2 in IPR2021-00250) dated Nov. 25, 2020 (107 pages).
Petition for Inter Partes Review of U.S. Pat. No. 10,625,261 (Paper 2 in IPR2021-00251) dated Nov. 25, 2020 (117 pages).
Petition for Inter Partes Review of U.S. Pat. No. 10,632,466 (Paper 2 in IPR2021-00253) dated Nov. 25, 2020 (121 pages).

(56) References Cited

OTHER PUBLICATIONS

Declaration of Mark A. Burns, Ph.D. (Exhibit N1001 in IPR2021-00250, IPR2021-00251 and IPR2021-00253) dated Nov. 24, 2020 (311 pages).
Declaration of James L. Mullins, Ph.D. (Exhibit N1029 in IPR2021-00250, IPR2021-00251, and IPR2021-00253) dated Nov. 18, 2020 (54 pages).
Decision Denying Institution of Inter Partes Review of U.S. Pat. No. 8,273,308 (Paper 14 in IPR2020-01091) dated Dec. 4, 2020 (21 pages).
Decision Denying Institution of Inter Partes Review of U.S. Pat. No. 8,703,069 (Paper 14 in IPR2020-01095) dated Dec. 4, 2020 (22 pages).
Decision Denying Institution of Inter Partes Review of U.S. Pat. No. 8,703,069 (Paper 15 in IPR2020-01100) dated Dec. 4, 2020 (19 pages).
Defendant NeuModx's Joint Claim Construction Chart [Exhibit N1023] filed Oct. 21, 2020 in U.S. District Court, Delaware, Case #1:19-cv-01126-LPS (25 pages).
Defendant NeuModx's Initial Amended Answer, Affirmative Defenses, and Counterclaims to Plaintiffs' First Amended and Supplemental Complaint filed Nov. 23, 2020 in U.S. District Court, Delaware, Case #1:19-cv-01126-LPS (97 pages).

\* cited by examiner

POLYNUCLEOTIDE CAPTURE MATERIALS, AND SYSTEMS USING SAME

CLAIM OF PRIORITY

This application is a continuation of U.S. application Ser. No. 16/818,458, filed on Mar. 13, 2020, which is a continuation of U.S. application Ser. No. 16/158,752, filed on Oct. 12, 2018 (now U.S. Pat. No. 10,590,410), which is a continuation of U.S. application Ser. No. 14/976,746, filed on Dec. 21, 2015 (now U.S. Pat. No. 10,100,302), which is a continuation of U.S. application Ser. No. 14/262,525, filed on Apr. 25, 2014 (now U.S. Pat. No. 9,217,143), which is a continuation of U.S. application Ser. No. 13/692,980, filed on Dec. 3, 2012 (now U.S. Pat. No. 8,710,211), which is a continuation of U.S. application Ser. No. 12/172,214, filed on Jul. 11, 2008 (now U.S. Pat. No. 8,324,372), which claims the benefit of priority under 35 U.S.C. § 119(e) to U.S. Provisional Application Ser No. 60/959,437, filed Jul. 13, 2007, all of which are incorporated herein by reference in their entirety.

TECHNICAL FIELD

The technology described herein generally relates to methods for processing biological samples, and more particularly relates to materials for capturing polynucleotide molecules such as RNA and DNA from such samples, and permitting quantitative determination thereof.

BACKGROUND OF THE INVENTION

Field of the Invention

The analysis of a biological sample such as a clinical sample or a test sample of food, for presence of a pathogen such as a virus, or to determine the presence of a particular gene, will typically include detecting one or more polynucleotides present in the sample. One type of detection is qualitative detection, which relates to a determination of the presence or absence of a target polynucleotide and/or the determination of information related to, for example, the type, size, presence or absence of mutations, and/or the sequence of the target polynucleotide. Another type of detection is quantitative detection, which relates to a determination of the amount of a particular polynucleotide present in the sample, expressed for example as a concentration or as an absolute amount by weight or volume. Detection may also include both qualitative and quantitative aspects. Quantitative detection is typically, however, a more challenging pursuit than is a simple qualitative determination of presence or absence of a polynucleotide.

Detecting polynucleotides often involves the use of an enzyme. For example, some detection methods include polynucleotide amplification by polymerase chain reaction (PCR) or a related amplification technique. Other detection methods that do not amplify the polynucleotide to be detected also make use of enzymes. However, the functioning of enzymes used in such techniques may be inhibited by the presence of materials (known as inhibitors) that accompany the polynucleotide in many biological—particularly clinical—samples. The inhibitors may interfere with, for example, the efficiency and/or the specificity of the enzymes.

Polynucleotide detection today is moving towards ever more rapid, and ever more sensitive techniques. For example, rapid and accurate diagnosis of viral infections is invaluable for accurate patient management by directing the administration of appropriate antiviral therapy, eliminating the unnecessary utilization of antibiotics and monitoring individual response to the prescribed regimen. Given its significant advantages of sensitivity, specificity and time to result, polynucleotide detection (or nucleic acid testing) has become the presumptive international standard for viral diagnosis.

However, the application of nucleic acid testing to routine diagnosis of viral targets has been limited to large clinical reference labs and major hospital labs due to the high cost, complexity and skill level requirements for implementing such testing. While significant improvements have been made in recent years, the successful detection of RNA viruses in particular requires extremely laborious extraction procedures frequently relying on the use of toxic chemicals. Furthermore, RNA molecules can be very unstable and hence can require delicate processing/handling during their determination. These issues to date have been overcome with the use of large, expensive, time consuming robotic equipment.

With the current demands on practice of medicine, laboratories that carry out diagnostic testing on patient samples see substantial benefits from having extremely high throughput, which in itself is assisted if the time to arrive at a diagnostic outcome for a given sample is made as short as possible. Testing may also be made more rapid if the actual sample on which the tests are run is made as small as possible. More recently, there has been a growing need for a small, easy to use, low-cost, automated platform for the extraction of high quality RNA from viral targets in clinical specimens.

Correspondingly, then, the need to be able to isolate minute quantities of polynucleotides from complex biological samples in a manner that effectively avoids the presence of, or reduces the detrimental impact of, inhibitors is ever more important. Furthermore, given the availability of various stand-alone automated amplification apparatuses, it is desirable to be able to routinely and reliably extract from a raw clinical sample a quantity of polynucleotide that is ready—in terms of purity and quantity—for amplification.

The discussion of the background herein is included to explain the context of the technology. This is not to be taken as an admission that any of the material referred to was published, known, or part of the common general knowledge as at the priority date of any of the claims found appended hereto.

Throughout the description and claims of the specification the word "comprise" and variations thereof, such as "comprising" and "comprises", is not intended to exclude other additives, components, integers or steps.

SUMMARY OF THE INVENTION

The process and materials herein are applicable to a number of testing targets, in particular those that are RNA based, such as Influenza (A & B), RSV, HSV, CMV, Adenovirus, and Enterovirus.

The technology herein provides excellent RNA—as well as DNA—capture and recovery via use of micro-particles having a high RNA and DNA binding capacity, such as 100 µg/mg beads, and a >90% release efficiency. In exemplary embodiments, 8-10 µg RNA can be extracted from an overnight culture. Processes, as described herein, permit very fast (15-20 minutes including lysis) RNA extraction from cellular or viral material, via a single tube process. Processes, as described herein, comprise a streamlined procedure having fewer steps (such as six) to proceed from raw sample to purified RNA. Such processes therefore provide an extremely effective clean-up of RNA from raw biological samples, thereby permitting PCR to be performed thereon. The methods and processes are applicable across a wide variety of sample matrices, as well as clinical buffers used when collecting raw samples, e.g., M4, UTM, and Todd Hewit Broth.

Suitable targets, that have assays used in clinical testing, and that may be the subject of sample preparation processes as described herein, include, but are not limited to: *Chlamydia Trachomatis* (CT); *Neisseria Gonorrhea* (GC); Group B *Streptococcus*; HSV; HSV Typing; CMV; Influenza A & B; MRSA; RSV; TB; *Trichomonas*; Adenovirus; *Bordatella*; BK; JC; HHV6; EBV; Enterovirus; and *M. pneumoniae*.

One aspect of the present invention relates to a method for processing one or more RNA and/or DNA compounds (e.g., to concentrate the RNA and/or DNA compound(s) and/or to separate the RNA and/or DNA compound(s) from inhibitor compounds (e.g., hemoglobin, peptides, faecal compounds, humic acids, mucousol compounds, DNA binding proteins, or a saccharide) that might inhibit detection and/or amplification of the RNA and/or DNA compounds).

In some embodiments, the method includes contacting the sample containing the RNA and/or DNA compounds and PAMAM (Generation 0) that preferentially associates with (e.g., retains) the RNA and/or DNA compounds as opposed to inhibitors. The PAMAM (Generation 0) is typically bound to a surface (e.g., a surface of one or more particles). The PAMAM (Generation 0) retains the RNA and/or DNA compounds so that the RNA and/or DNA compounds and inhibitors may be separated, such as by washing the surface with the compound and associated RNA and/or DNA compounds. Upon separation, the association between the RNA and/or DNA compound and the PAMAM(Generation 0) may be disrupted to release (e.g., separate) the RNA and/or DNA compounds from the compound and surface.

The present disclosure provides for a method for isolating polynucleotides from a cell-containing sample, the method comprising: contacting the sample with a lysis solution and a plurality of binding particles coated in PAMAM(Generation 0), so that the polynucleotides are liberated from the cells and become bound to the PAMAM(Generation 0), thereby creating binding particles bound with polynucleotides and a solution containing residual cellular matter; compacting the binding particles bound with polynucleotides; removing the solution containing residual cellular matter; washing the binding particles; and releasing the polynucleotides from the binding particles.

The present disclosure further includes a process for concentrating RNA from a sample containing polymerase chain reaction inhibitors, the method comprising: contacting between 500 µl and 1 ml of the sample with a plurality of RNA binding particles, the binding particles configured to preferentially retain the RNA in the sample as compared to the polymerase chain reaction inhibitors; concentrating the plurality of particles having the one or more polynucleotides bound thereto into an effective volume between 50 nanoliters and 5 microliters; and releasing the one or more polynucleotides into <30 µl of solution.

The present disclosure still further includes a composition comprising: carboxyl modified microparticles; and PAMAM (Generation 0) bound via one or more amine groups per molecule to one or more of the carboxylic acid groups on the microparticles.

The present disclosure additionally includes a kit, comprising: a number of sealed tubes, each containing lysis buffer; a tube containing lyophilized microparticles having PAMAM(Generation 0) bound thereto; a tube containing liquid wash reagents, sufficient to analyze the number of samples; and a tube containing liquid release reagents, sufficient to analyze the number of samples, wherein each component of the kit is stored in an air-tight container.

The present disclosure still further includes a kit, comprising: a first air-tight pouch enclosing a number of tubes, each tube containing lyophilized microparticles having PAMAM(Generation 0) bound thereto; a second air-tight pouch enclosing a number of reagent holders, each holder comprising: a tube containing liquid lysis reagents; a tube containing liquid wash reagents; and a tube containing liquid release reagents.

The present disclosure additionally includes a method of making a polynucleotide retention member, the method comprising: washing a quantity of microspheres with carbonate and MES buffer; preparing sulfo-NHS and EDAC; incubating the microspheres with sulfo-NHS and EDAC for 30 minutes; washing the microspheres with MES and borate buffer; contacting the microspheres with PAMAM(0) for 8-10 hours; and rinsing unbound PAMAM(0) from the microspheres.

BRIEF DESCRIPTION OF THE DRAWINGS

Like reference symbols in the various drawings indicate like elements.

DETAILED DESCRIPTION

Figure 1:
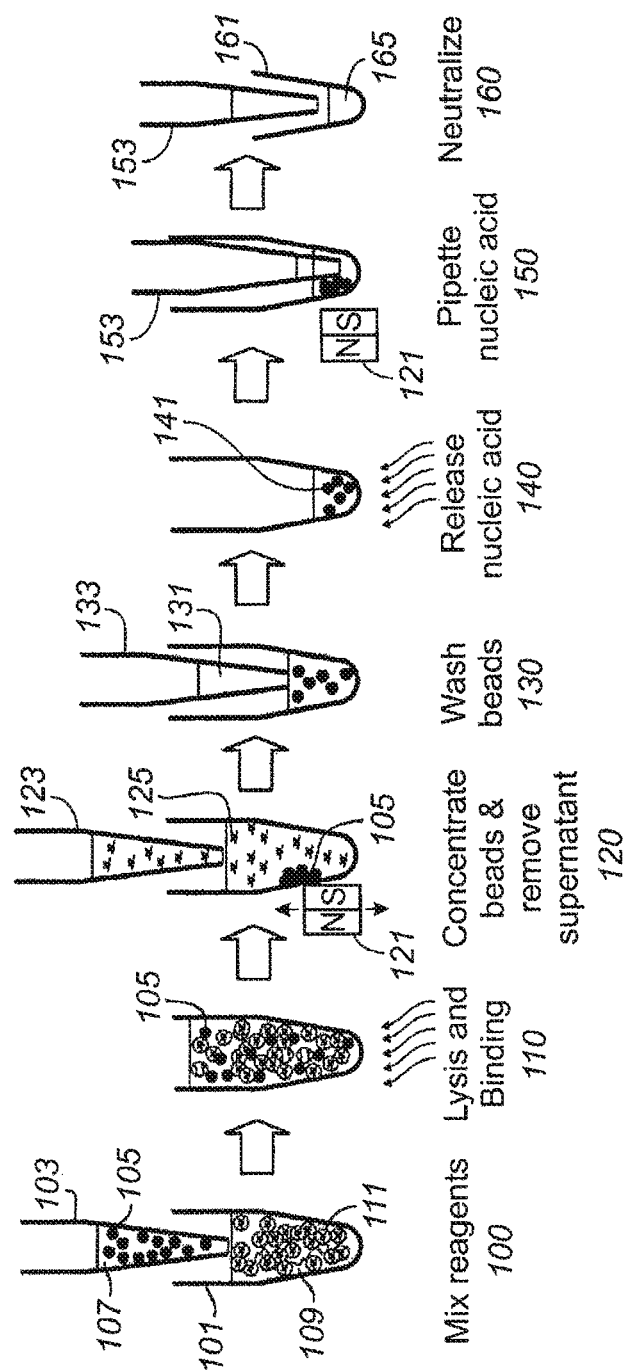
FIG. 1 shows schematically a typical process as described herein.

Analysis of biological samples often includes determining whether one or more polynucleotides (e.g., a DNA, RNA, mRNA, or rRNA) is present in the sample. The technology described herein has applicability to determining both RNA and DNA that is present in a sample. For example, a sample may be analyzed to determine whether the RNA of a particular pathogen is present, and also whether DNA of another or the same pathogen is present. If present, the RNA or the DNA may together or separately be indicative of a corresponding disease or condition.

Accordingly, the technology described herein is directed to materials that bind polynucleotides, and use of such materials in isolating polynucleotides, such as DNA and RNA, from biological samples. The materials, in conjunction with methods of using the materials, provide for rapid and reliable extraction of RNA and DNA from many different types of biological samples, including quantitative determination of both the RNA and the DNA. Such methods are typically referred to as "sample preparation" methods. What is meant by such a term is the liberation, extraction, concentration, and/or isolation, of RNA and/or DNA of a target organism from a raw sample—such as obtained directly from a patient or an agricultural or food product—where the raw sample contains the target RNA and/or target DNA bound in cellular form. The liberated target RNA and/or target DNA is placed, at the culmination of the process, in a form suitable for amplification and/or detection.

The terms DNA (deoxyribonucleic acid) and RNA (ribonucleic acid), and together as polynucleotides, as used herein can mean an individual molecule or population of molecules, such as identifiable by having a specific nucleotide sequence common to all, or can mean collectively molecules of DNA or RNA having different sequences from one another. For example, a biological sample from a human patient may contain DNA from the patient's cells, having one sequence, and DNA or RNA from cells of a pathogen, having a different sequence from that of the patient's DNA. The sample is thus referred to as containing DNA and RNA (or, together, polynucleotides), even though there are molecules of DNA (or RNA) in the sample that are different (chemically distinct) from one another. The methods herein can be used to liberate, collectively, molecules of DNA and RNA from both the patient's and the pathogen's cells in such a sample. Typically, however, in such an instance, it will usually be the DNA or RNA of the pathogen that will be of interest, and which will be selectively amplified from amongst all the DNA and RNA that is ultimately isolated from the sample. The DNA and RNA that is best suited for extraction by the methods herein has a size less than 7.5 Mbp, though it would be understood that larger DNA and RNA molecules may be susceptible to extraction and detection by the methods herein.

Typically, biological samples are complex mixtures. For example, a sample may be provided as a blood sample, a tissue sample (e.g., a swab of, for example, nasal, buccal, anal, or vaginal tissue), a biopsy aspirate, a lysate, as fungi, or as bacteria. The RNA and/or DNA to be determined is normally contained within particles (e.g., cells such as white blood cells, or red blood cells), tissue fragments, bacteria (e.g., gram positive bacteria, or gram negative bacteria), fungi, or spores. One or more liquids (e.g., water, a buffer, blood, blood plasma, saliva, urine, cerebral spinal fluid (CSF), or organic solvent) is typically part of the sample and/or is added to the sample during a processing step. The materials and methods described herein are compatible with a variety of clinical matrices, at least including blood, urine, CSF, swab, and plasma.

Methods for analyzing biological samples include releasing RNA and/or DNA from the particles (e.g., bacteria) in the sample, amplifying one or more of the released RNA and/or DNA (e.g., by polymerase chain reaction (PCR)), and determining the presence (or absence) of the amplified polynucleotide(s) (e.g., by fluorescence detection).

Clinical samples present a variety of challenges especially in the detection of target RNA and DNA through PCR or similar technologies. A target nucleic acid could be present in a concentration as low as 10 copies per milliliter as measured against a background of millions or billions of copies of competing nucleic acids (such as from a patient's normal cells). Moreover, a variety of other biochemical entities present in the clinical sample inhibit PCR. The inhibitors may also frustrate isolation of RNA or DNA from the sample, such as by being captured by a material designed to retain the RNA or DNA. If the concentration of inhibitors is not reduced relative to the RNA or DNA to be determined, the analysis can produce false negative results. Examples of these inhibitors, dependent upon the biological sample in question, are cellular debris such as membrane fragments, humic acids, mucousal compounds, hemoglobin, other proteins such as DNA binding proteins, salts, DNAases, fecal matter, meconium, urea, amniotic fluid, blood, lipids, saccharides, and polysaccharides. For example, such inhibitors can reduce the amplification efficiency of DNA and RNA by PCR and other enzymatic techniques for determining the presence of DNA and RNA.

Therefore, an effective sample preparation method should lead to a concentration of the target RNA or DNA, and should minimize presence of inhibitory substances. The methods described herein may increase the concentration of the DNA and/or RNA to be determined and/or reduce the concentration of inhibitors relative to the concentration of DNA and/or RNA to be determined.

In addition, cells of some target organisms, such as gram positive bacteria (e.g. Group B Strep), are very hard to lyse, meaning that lysing conditions can be very severe. Such organisms may require additional chemicals for lysing, such as mutanolysin, and may also require higher temperatures for optimal lysis. Such conditions may be accommodated by the materials and methods described herein.

Sample Preparation Process

A typical sample preparation process may be carried out in a processing chamber that includes a plurality of particles (e.g., beads, microspheres) configured to retain RNA and/or DNA of the sample under a first set of conditions (e.g., a first temperature and/or first pH) and to release the RNA under a second set of conditions (e.g., a second, higher temperature and/or a second, more basic, pH), and to release DNA under a third set of conditions (e.g., a third, different temperature and/or a third, more basic, pH than that used in the first and second conditions). Typically, the DNA and RNA are retained preferentially as compared to inhibitors that may be present in the sample.

An exemplary sample preparation process is illustrated in FIG. 1. The various reagents referred to in connection with FIG. 1 are described in further detail elsewhere herein. At 100, a process tube 101, such as a standard laboratory 1.7 ml microcentrifuge tube, contains a biological sample comprising a liquid 109, such as an aqueous solution, and cellular materials 111, wherein at least some of the cellular materials may contain RNA and/or DNA of a target of interest. The biological sample may be any of those described elsewhere herein, and process tube 101 may be any tube or suitable vessel, as further described herein. It is to be understood that, although the process is illustrated with respect to FIG. 1, the process is not limited to be carried out in a tube. The sample and various reagents may be, for example, delivered to, and mixed and reacted within, chambers of a microfluidic device such as a microfluidic cartridge, as further described in U.S. patent application Ser. No. 11/281,247, filed Nov. 16, 2005 and incorporated herein by reference.

A first pipette tip 103 contains a solution 107 of microparticles 105, that are delivered to the process tube and contacted with the biological sample contained therein. The surfaces of particles 105 are modified to have PAMAM(0) attached, as further described herein, so that they retain RNA and/or DNA in preference to inhibitors in solution. Solution 107 may be a lysis solution, as further described herein. The lysis solution may contain a detergent, in addition to various enzymes, as described elsewhere herein. Thorough mixing of the microparticles, the solution, and the biological sample may occur simply by turbulent combination of the two solutions upon release of the microparticle containing solution from the pipette tip, or may occur via mechanical or manual agitation of process tube 101.

First pipette tip 103 is positioned above process chamber 101, such as by manual operation by a user, or such as by an automated pipetting head, an example of which is described in U.S. provisional patent application Ser. No. 60/959,437, filed Jul. 13, 2007, which is incorporated herein by reference.

At 110, using the same process tube 101, the microparticles, biological sample, and lysis reagents are incubated, such as by applying heat from an external source, as shown, so that the cells in the biological sample are lysed, and liberate RNA and/or DNA. Under these conditions, the DNA molecules bind to suitably configured surfaces of the microparticles, as further described herein. Typically, the particles retain RNA and/or DNA from liquids having a pH about 9.5 or less (e.g., about 9.0 or less, about 8.75 or less, about 8.5 or less). It is to be noted that the binding of DNA to the affinity microparticles happens concurrently with the lysis process, and the binding is not adversely affected by the presence of detergents and, in some instances, lytic enzymes in the lysis solution. The choice of temperature is dictated by what is required to lyse the cells in question, and heat is not required to effectuate binding of the RNA or DNA to the particles. Typically, those cells having tougher cell walls (e.g., lysteria, or anthrax) will require higher temperatures. For example, *Chlamydia* determination utilizes a temperature of 37° C. for a duration of 5-10 minutes for lysis and binding, whereas Group B *Streptococcus* determination utilizes a temperature of 60° C. for a duration of 5-10 minutes. Generally, the liquid is heated to a temperature insufficient to boil liquid in the presence of the particles.

At 120, the microparticles are concentrated or compacted, and the remaining solution containing residual cellular matter 125 is removed, for example by a second pipette tip 123. By compacted is meant that the microparticles, instead of being effectively uniformly distributed through a solution, are brought together at a single location in the process tube, in contact with one another. Where the microparticles are magnetic, compaction of the microparticles may be achieved by, for example, bringing a magnet 121 into close proximity to the outside of the process chamber 101, and moving the magnet up and down outside the chamber. The magnetic particles are attracted to the magnet and are drawn towards the inside of the wall of the process chamber adjacent the magnet.

Pipette tip 123 removes as much of the remaining solution (sometimes referred to as supernatant, or solution having residual cellular matter) as is practical without drawing up significant quantities of microparticles. Typically a pipette tip may slide into process chamber 105 without contacting the microparticles. In this way the microparticles are concentrated, by being present in a smaller volume of solution than hitherto. Pipette tip 123 may be a different tip from pipette tip 103, or may be the same tip. In some embodiments, after removal of the solution containing residual cellular matter, less than 10 microliters of solution is left along with the particles. Typically this is achieved by both compaction of the microparticles to a small pellet, but also positioning that pellet away from the location wherein the pipette will be introduced for removal of the supernatant. The positioning of the pipette in relation to the bottom of the tube is also important so that almost all of the supernatant is removed. The pipette tip should be almost close to the bottom of the tube (within 1-2 mm) but without completely sealing the pipette tip against the tube bottom. A stellated pattern may also be used at the bottom of the lysis tube, (as described in U.S. provisional patent application Ser. No. 60/959,437, filed Jul. 13, 2007, and incorporated herein by reference), but the positioning of the patterns in relation to the location of the magnet becomes important so that the sliding of the compacted microparticles is not hindered and the crevices between vertices of the stellated pattern do not trap microparticles.

At 130, a third pipette tip 133 delivers a wash solution 131 to the process chamber 101 containing compacted microparticles. The wash solution may comprise, e.g., a buffer such as Tris-EDTA with a surfactant such as 1% Triton X 100, and having an overall pH 8.0. Typically, the volume of wash buffer is 100 microliters or less, where the sample is 2 ml or less in volume. The wash solution is used to wash off any non-DNA and non-RNA molecules, such as inhibitors, that may have become bound to the microparticles. The wash solution is chosen to preferentially wash off non-RNA and non-DNA molecules while leaving in place those RNA and/or DNA molecules bound to the microparticles. Pipette tip 133 may be a different tip from either or both of pipette tips 103 and 123, or may be one of those tips being re-used.

In order to release the RNA and, separately, the DNA from the particles, the wash solution 131 is replaced with an alkaline (pH ~9.0) release solution, e.g., a buffer solution having a pH different from that of the wash solution. This can be done by pipetting out as much of the wash solution as possible, for example, having a residual volume <5 microliters, and then dispensing release buffer with a new pipette tip. In case the same tip is used, the liquid should be completely drained off so as not to dilute the release solution. For example, at 140, a release solution 141 is delivered to process chamber 101 so that the RNA bound to the micro-particles can be liberated from those micro-particles. In general, the PAMAM(Generation 0) on the particles (as further described herein) most efficiently releases RNA when the pH is about 9. Consequently, RNA can be released from the particles into the surrounding liquid. In some instances, heat may be applied to the process tube, such as to heat the solution to 85° C., to facilitate release of the RNA. Generally, the liquid is heated to a temperature insufficient to boil liquid in the presence of the particles. In some embodiments, the temperature is 100° C. or less (e.g., less than 100° C., about 97° C. or less). In some embodiments, the temperature is about 65° C. or more (e.g., about 75° C. or more, about 80° C. or more, about 90° C. or more). In some embodiments, the temperature is maintained for about 1 minute or more (e.g., about 2 minutes or more, about 5 minutes or more, about 10 minutes or more). In some embodiments, the temperature is maintained for about 30 minutes (e.g., about 15 minutes or less, about 10 minutes or less, about 5 minutes or less). In some embodiments, the process tube is heated to between about 65 and 90° C. (e.g., to about 70° C.) for between about 1 and 7 minutes (e.g., for about 2 minutes). In other embodiments, the heating is to 85° C. for 3 minutes. In still other embodiments, the heating is to 65° C. for 6 minutes. In general, a longer heating time is required for a lower temperature. Alternatively, or in combination, particles with retained RNA are heated to release the RNA without assistance of a release solution. When heat alone is used to release the RNA, the release solution may be identical with the wash solution.

Typically, the RNA from a 2 ml sample, and according to the description of the lysis, binding, and washing described elsewhere therein, is released into about 20 microliters or less (e.g., about 10 microliters or less, about 5 microliters or less, or about 2.5 microliters or less) of liquid.

While releasing the RNA has been described as including heating, the RNA may be released without heating. For example, in some embodiments, the release solution has an ionic strength, pH, surfactant concentration, composition, or combination thereof that releases the RNA from the retention member without requiring heat.

It is to be noted that excessive shearing, such as is caused by rapid movements of the liquid during suck-and-dispense mixing operations during wash and release (typically during DNA release) in the sample preparation process may release PAMAM(Generation 0) from the surface of the particles, which itself causes downstream inhibition of PCR. The mixing steps should be limited to less than 10 suck-and-dispense operations, where the amount moved back and forth ranges from 1-20 microliters moved in the pipette, performed over 1-10 seconds per suck-and-dispense operations.

At 150 the microparticles, now having essentially no RNA bound thereto, can be compacted or concentrated in a similar manner to that described for 120, but in this case to facilitate removal of the release solution containing the RNA dissolved therein. For example, magnetic beads can be collected together on the interior of the process chamber wall by bringing magnet 121 into close proximity to the outside of the process chamber. In FIG. 1, magnet 121 is used to compact the microparticles at both stages 120 and 150, though it would be understood that a different magnet could be used in both instances.

In instances where a sample contains both RNA and DNA, and it is desired to determine both a particular RNA and a particular DNA, the procedures at 140 and 150, as described herein, may be repeated, using a second release solution that is designed to release DNA. As described further in U.S. patent application Ser. No. 12/172,208, filed on even date herewith, and entitled "POLYNUCLEOTIDE CAPTURE MATERIALS, AND METHODS OF USING SAME", a solution designed to release DNA typically has a pH of about 12 or greater. Such a procedure relies on the fact that RNA and DNA have different pKa's and therefore will elute from the surface of a particle to which they are non-covalently bound, at different pH's from one another. Similar considerations, such as release conditions (temperature, reagent concentrations, etc.) apply to release of DNA as to RNA.

It is to be noted that, thus far, all of the processing steps have taken place in a single tube. This is advantageous for a number of reasons: first, that unnecessary liquid transfer steps will necessarily lead to some loss of target material. Additional liquid transfer steps will also add to the overall time of the protocol. It should be noted that performing all the liquid processing in a single tube is not an easy task primarily because of the residual volumes left between successive liquid transfers. It becomes even more difficult when the final elution volume is very low, such as less than 30 microliters, or less than 20 microliters or less than 10 microliters, or less than 5 microliters. Nevertheless, with the protocols described herein, very good yields may be obtained.

The RNA, and/or subsequently the DNA, liberated from the microparticles can each be drawn up into a fourth pipette tip 153 in solution in the release solution. Pipette tip 153 need not be different from all of pipette tips 103, 123, and 133 and may therefore represent a re-use of one of those tips. Although it is desirable to use magnetic beads, non-magnetic beads may also be used herein, and separated by, e.g., centrifugation, rather than by use of a magnet.

In certain embodiments, the ratio of the volume of original sample introduced into the processing tube to the volume of liquid into which the RNA or DNA is released is at least about 10 (e.g., at least about 50, at least about 100, at least about 250, at least about 500, at least about 1,000). In some embodiments, RNA or DNA from a sample having a volume of about 2 ml can be retained within the processing tube, and released, after binding and washing, into about 4 microliters or less (e.g., about 3 microliters or less, about 2 microliters or less, about 1 microliter or less) of liquid.

In some embodiments, the sample has a volume larger than the concentrated volume of the binding particles having the RNA or DNA bound thereto by a factor of at least about 10.

In other embodiments, the sample has a volume of 100 μ-1 ml, and the compacted particles occupy an effective volume of less than 2 microliters.

The liquid into which the RNA or DNA is released typically includes at least about 50% (e.g., at least about 75%, at least about 85%, at least about 90%, or at least about 95%) of the RNA or DNA respectively present in the sample 109. Thus, for example, ~8-10 μg DNA can be liberated from 1 ml of overnight culture, and 2-4 μg DNA can be extracted from one buccal swab. The concentration of RNA or DNA present in the release liquid may be higher than the respective concentration in the original sample because the volume of release liquid is typically less than the volume of the original liquid sample. For example, the concentration of DNA in the release liquid may be at least about 10 times greater (e.g., at least about 25 times greater, at least about 100 times greater) than the concentration of DNA in the sample 109. The concentration of inhibitors present in the liquid into which the RNA or DNA is released is generally less than the concentration of inhibitors in the original fluidic sample by an amount sufficient to increase the amplification efficiency for the RNA or DNA over that which could be obtained from an unpurified sample.

In general, although the processes and materials described herein are capable of performing well—usually with only routine adaptation—over a wide range of sample sizes, and reagent volumes, for most practical applications (considering the size of most biological samples subject to diagnostic analysis), the volume of compacted particles having RNA and/or DNA bound thereto that results (prior to release) is in the range 2-3 μl, and is independent of the sample volume, up to about 2 ml of sample. Typically the quantity of microparticles required is determined by the quantity of RNA and/or DNA in the sample. It is found that, given the efficiency of binding to the particles, 0.5 mg of particles is sufficient for most manual applications, and most involving automated pipetting, regardless of sample size. Thus, for example, for samples having volumes from 0.5 microliters to 3 milliliters, the volume of the compacted particles is 2-3 μl. For example, for Chlamydia, the sample size is typically 1 ml, and 0.5 mg of particles is sufficient. For other applications, DNA from a 2 ml sample can also be extracted with 0.5 mg particles, or in some instances 1 mg beads can be used. For smaller samples, such as having a volume of 5 μl, it is still typical to use only 0.5 mg particles.

In order to agitate the solution at various stages during the manual process, the solution may be pipetted up and down a number of times, such as 10 times, 15 times, or 20 times. Such a procedure is acceptable during the release step as well as the wash steps. Vortexing also works for these steps. However, for the automated process, cannot tolerate any mix steps, the number of mixing operations is kept at a minimum as this was possibly causing some PAMAM(0) to come off and inhibit downstream PCR.

The process described herein represents an extremely effective clean-up of a sample in preparation for PCR and provides the capability to detect as few as 25 copies of RNA or DNA from 1 milliliter of clinical sample. The RNA or DNA is present in a high level of concentration because the elution volume can be as low as 3 microliters. There is also a low residual sample liquid and/or wash volume in the concentrated microspheres, thereby minimizing dilution by sample or wash buffer, as well as minimizing inhibition from residual sample.

The time interval between introducing the polynucleotide containing sample to processing tube 101, and releasing the RNA or DNA into the release liquid is usually between 10 and 30 minutes, and is typically about 15-20 minutes, or may be 15 minutes or less (e.g., about 10 minutes or less, about 5 minutes or less). These times include the lysis time (which doubles up as a sample-binding time), and are extremely fast. To release both RNA and DNA, separately, from a single sample, it is only necessary to add an additional release procedure, as in 140 in FIG. 1.

Optionally, at 160 in FIG. 1, the released RNA or DNA in solution may be neutralized by contacting it with a neutralization solution 165 (e.g., an equal volume of 25-50 mM Tris-HCl buffer pH 8.0). For example, the RNA or DNA in solution in pipette tip 153 may be released into a second process chamber, or vessel, 161 such as a standard laboratory PCR tube, in which the neutralization solution is present. The PCR tube may be removed and introduced into a PCR machine for further analysis. Typically, the solutions for extracting RNA are close enough to neutrality that a separate neutralization step is not required.

The RNA or DNA in solution in vessel 161 is in a state that it can be amplified, such as by PCR, and detected. Furthermore, the foregoing process steps are extremely reliable and robust, and enable quantitative assays of the extracted RNA or DNA over 7 log dilutions (10-$10^7$ copies of target RNA or DNA/ml of sample).

The process of FIG. 1 has demonstrated effectiveness in manual as well as automated formats.

The process shown in FIG. 1 may be carried out in conjunction with a reagent holder, in which the process chamber may be situated, and in which are found appropriate quantities of microparticles, lysis solution, wash solution, release solution, and neutralization solution, each of which is accessible to one or more pipette tips and for use as shown in FIG. 1. An exemplary reagent holder is described in U.S. provisional patent application Ser. No. 60/959,437, filed Jul. 13, 2007, and incorporated by reference herein.

Where a magnet is shown in FIG. 1 for use in compacting magnetic microparticles, a magnetic separator, as described in U.S. provisional patent application Ser. No. 60/959,437, filed Jul. 13, 2007, and incorporated by reference herein, may be used.

Where it is shown in FIG. 1 that heat may be applied to process chamber 101, a heater assembly, as described in U.S. provisional patent application Ser. No. 60/959,437, filed Jul. 13, 2007, and incorporated by reference herein, may be used.

The process shown in FIG. 1 is optimally used to prepare highly pure and concentrated RNA or DNA for use in low-volume (e.g. 4 µl) PCR reactions, such as may be carried out in a microfluidic cartridge, for example a microfluidic cartridge described in U.S. provisional patent application Ser. No. 60/959,437, filed Jul. 13, 2007, and incorporated herein by reference.

Figure 2:
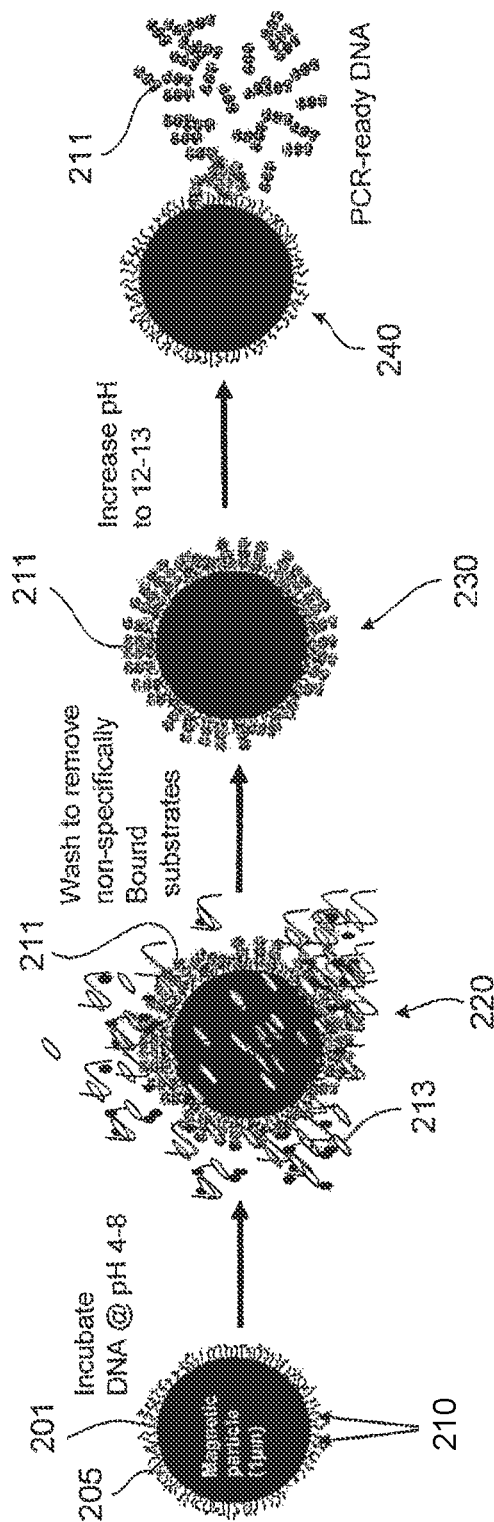
FIG. 2 shows schematically the action of DNA affinity beads as further described herein.

FIG. 2 shows, schematically, a sample preparation process at the molecular level. At 210, a typical magnetic particle 201, having a diameter of 1 µm, is shown. Attached to the surface of particle 201 are molecules 205 having a binding affinity for polynucleotides in solution surrounding the particle. Attachment of molecules 205 is usually via covalent bonds. Such molecules are further described herein and in some embodiments are molecules of PAMAM(Generation 0). From 210 to 220, the magnetic particle is incubated in a solution containing RNA and/or DNA, at a pH of 4-8, lower than the pKa of molecules 205. At 220, particle 201 is shown having polynucleotide (i.e., DNA and/or RNA) molecules 211 attached to the affinity molecules 205. Also shown are various other non-specifically bound substrates 213, denoted by small ovals, cigar-shapes, and curved lines.

Moving from 220 to 230 in FIG. 2, the particle 201, to which is bound both RNA and/or DNA molecules 211, and non-specifically bound molecules 213, is washed to remove the non-specifically bound substrates, leaving a particle coated in affinity molecules 205 and RNA and/or DNA molecules 211 bound thereto. From 230 to 240, the RNA and/or DNA molecules 211 are released from the surface of the particle by increasing the pH of the solution surrounding the particle to a pH of 9 (RNA) and, subsequently a pH of 12-13 (to release DNA). The released RNA and/or DNA molecules can be separately collected in a PCR-ready format.

While samples and various solutions have been described herein as having microliter scale volumes, other volumes can be used. For example, processing tubes with surfaces (e.g., particles) configured to preferentially retain RNA and/or DNA as opposed to inhibitors may have large volumes (e.g., many tens of microliters or more, at least about 1 milliliter or more).

In some embodiments, the processing tube has a benchtop scale, and other solutions are correspondingly scaled up.

Polynucleotide Capture Material

Suitable polynucleotide affinity molecules are those that offer a very high density of positively ionizable charges at a low pH, and enable strong attraction and binding of polynucleotides, including RNA and DNA from a clinical lysate, within a few minutes.

A typical embodiment of the materials herein uses: Polyamidoamine (PAMAM) Generation 0, available from the Sigma-Aldrich Chemical Company ("Sigma-Aldrich"), product number 412368. This material, referred to hereinafter as "PAMAM(Generation 0)" or "PAMAM(0)" of "PAMAM(G0)", is a dendrimer whose molecules have the following structure.

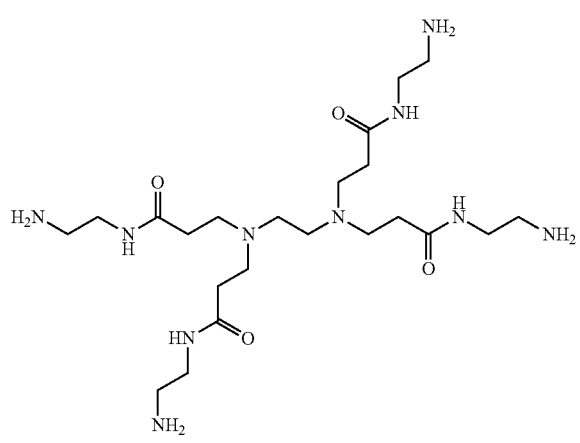

PAMAM Generation 0

The core of the molecule is an ethylene diamine substituted twice on both nitrogen atoms by an acetyl group. Each acetyl group has itself reacted with ethylene diamine monomers to yield amino-substituted amide groups.

The form of PAMAM(0) suitable for use herein is not limited to that product available from Sigma-Aldrich, however. PAMAM(0), being dendrimeric in nature, admits of a wide range of forms, controlled at least in part by the extent of dendrimerization permitted during its synthesis. Thus, many variants of PAMAM(0), having variously, different numbers of substituting units, are suitable for use herein. In general, there is a range of sizes of dendrimer molecule (or PAMAM(0) derivative) that is suitable for polynucleotide capture: smaller sizes don't capture enough RNA or DNA, whereas larger sizes retain the RNA or DNA too strongly, and do not permit easy release. Additionally, different monomers from ethylene diamine may be used to make a variant of PAMAM suitable for use herein. Such monomers may include, without limitation, 1,2-propylene diamine, 1,3-propylene diamine, 1,2-butylene diamine, 1,3-butylene diamine, and 1,4-butylenediamine.

Molecules of PAMAM suitable for use herein may also be characterized by molecular weight. In particular, PAMAM (0) has a molecular weight of 516; other suitable PAMAM molecules have weights in the range 500-600 Da.

PAMAM(0) can itself function as an inhibitor of enzymatic processes such as DNA and RNA amplification, and therefore it is important that it be used in a manner in which it does not reside in solution together with the released RNA and/or DNA. Aspects of this are further described in the Examples, hereinbelow.

Support Materials

During use, PAMAM(0) is typically immobilized on, such as bound to the surface of, a solid support such as carboxylated beads, or magnetic or non-magnetic beads. In many embodiments, such a solid support comprises microparticles, such as beads, and microspheres. These terms, microparticles, beads, and microspheres may be used interchangeably herein. The particles are typically formed of a material to which the PAMAM(0) can be easily associated. Exemplary materials from which such particles can be formed include polymeric materials that can be modified to attach a ligand. Typically, such a solid support itself may be derivatized to yield surface functional groups that react easily with PAMAM(0) molecules to create a chemical bond between the surface and the PAMAM(0). A frequently-employed—and desirable—surface functional group is the carboxylic acid (COOH) group. Exemplary polymeric materials that provide, or can be modified to provide, carboxylic groups and/or amino groups available to attach PAMAM(0) include, for example, polystyrene, latex polymers (e.g., polycarboxylate coated latex), polyacrylamide, polyethylene oxide, and derivatives thereof. Polymeric materials that can used to form suitable particles are described in U.S. Pat. No. 6,235,313 to Mathiowitz et al., which patent is incorporated herein by reference. Other materials include glass, silica, agarose, and amino-propyl-tri-ethoxy-silane (APES) modified materials.

During the process of reaction of a PAMAM(0) molecule with a carboxylated particle, such as a magnetic particle, one of the amine groups out of the total possible amine groups on a PAMAM(0) molecule, such as 6 possible groups in the aforementioned product from Sigma Aldrich, is consumed to react with the COOH group of the surface of the particle to form a carbodiimide bond. (See, e.g., U.S. application Ser. No. 11/281,247, page 40). The remainder of the total number amine groups, such as 5 groups in the aforementioned product from Sigma Aldrich, are available for protonation.

In some embodiments, a synthetic protocol comprises: washing a quantity of microspheres with carbonate and MES buffer; preparing sulfo-NHS and EDAC; incubating the microspheres with sulfo-NHS and EDAC for 30 minutes; washing the microspheres with MES and borate buffer; contacting the microspheres with PAMAM(0) for 8-10 hours; and rinsing unbound PAMAM(0) from the microspheres. An example of synthetic protocols for making PAMAM(0)-bound microparticles, is given in the Examples, hereinbelow.

There are a variety of sources of bead or particle that can be used to bind PAMAM(0), and used in the processes described herein, for example: Seradyn Magnetic carboxyl modified magnetic beads (Part #3008050250, Seradyn), Polysciences BioMag carboxyl beads, Dynal polymer encapsulated magnetic beads with a carboxyl coating, and Polybead carboxylate modified microspheres available from Polyscience, catalog no. 09850.

The high density of the PAMAM(0) molecules on bead surfaces permits even a small quantity of beads (0.5 mg) to be used for clinical samples as large as a milliliter, and permits binding of even low levels of target RNA or DNA (<100 copies) in a background of billions of copies of other polynucleotides.

In some embodiments, at least some (e.g., all) of the particles are magnetic. In alternative embodiments, few (e.g., none) of the particles are magnetic. Magnetic particles are advantageous because centrifugation is generally not required to separate them from a solution in which they are suspended.

Particles typically have an average diameter of about 20 microns or less (e.g., about 15 microns or less, about 10 microns or less). In some embodiments, particles have an average diameter of at least about 4 microns (e.g., at least about 6 microns, at least about 8 microns). Magnetic particles, as used herein, typically have an average diameter of between about 0.5 microns and about 3 microns. Non-magnetic particles, as used herein, typically have an average diameter of between about 0.5 microns and about 10 microns.

The particle density is typically at least about $10^7$ particles per milliliter (e.g., about $10^8$ or about $10^9$ particles per milliliter). For example, a processing region, such as present in a microfluidic device configured for used in sample preparation, with a total volume of about 1 microliter, may include about $10^3$ beads.

In some embodiments, at least some (e.g., all) the particles are solid. In some embodiments, at least some (e.g., all) the particles are porous (e.g., the particles may have channels extending at least partially within them).

The microparticles described herein are not only suitable for use in process tubes that are handled by manual pipetting operations, but they can be used in a microfluidic devices, such as in sample concentrator, thereby enabling even sub-microliter elution volumes to be processed, as applicable.

The microparticles having PAMAM(0) bound thereto are particularly effective at capturing, and releasing RNA, and also DNA. In some embodiments, the ratio by weight of the RNA captured by the binding particles, to the binding particles prior to contact with the RNA, is 5-20%. In other embodiments, the ratio is 7-12%. In still other embodiments, the ratio is about 10%, corresponding to, e.g., 100 μg of RNA for each mg of particles.

The microparticles having PAMAM(0) bound thereto are particularly effective at capturing RNA, and/or DNA, consistently over a wide range of concentrations, thereby permitting quantitative analysis of the RNA and/or DNA to be carried out. In some embodiments, the binding particles capture 90% or more of the RNA or DNA liberated from cells into a solution in contact with the binding particles, over a range of 1 to $10^7$ copies of target RNA or DNA/milliliter of sample.

In some embodiments, the binding particles release 90% or more of the DNA bound thereto when certain release conditions are deployed.

Sample Preparation Kits

Microparticles, coated with PAMAM(0), can be provided to a user in solid form, such as in lyophilized form, or in solution. It is desirable that the reagent, however provided, can be used immediately by a user for whatever intended purpose, without any preparatory steps. Microparticles prepared by the methods described herein can be lyophilized by methods known in the art, and applicable to microparticles of the sizes and characteristics described herein.

In each of the kits described herein, neutralization reagents are not required in the event that the kits are only to be used for determining RNA compounds. Thus neutralization reagents may be provided but are optional. Neutralization reagents are typically deployed in instances when the kits are used for DNA determination or for determining both RNA and DNA.

Such microparticles can also be provided in kit form, in conjunction with other reagents that are used, for example, in sample preparation. One embodiment of a kit comprises a number of, such as 24, sealed tubes, each containing lysis buffer; a tube containing lyophilized microparticles having PAMAM(0) bound thereto; a tube containing liquid wash reagents, sufficient to analyze the number of samples; a tube containing liquid neutralization reagents, sufficient to analyze the number of samples; and a tube containing liquid release reagents, sufficient to analyze the number of samples, wherein each component of the kit is stored in an air-tight container. Other numbers of tubes available in kit form include 12, 25, 30, 36, 48, 50, 60, and 100. Still other numbers are also permissible and consistent with the description herein.

Furthermore, in other embodiments of such a kit, the tube containing lyophilized microparticles can additionally contain particles of reagents selected from the group consisting of: proteinase-k; proteinase-k and mutanolysin; and proteinase-k, mutanolysin, and an internal control DNA. The additional enzymes are often used in cell-specific lysis applications.

In other embodiments, a kit comprises: a first air-tight pouch enclosing a number of—such as 24—tubes, each tube containing lyophilized microparticles having PAMAM(0) bound thereto; a second air-tight pouch enclosing a number of reagent holders, each holder comprising: a tube containing liquid lysis reagents; a tube containing liquid wash reagents; a tube containing liquid neutralization reagents; and a tube containing liquid release reagents. Other numbers of tubes available in kit form include 12, 25, 30, 36, 48, 50, 60, and 100. Still other numbers are also permissible and consistent with the description herein.

Furthermore, in other embodiments of such a kit, the tube containing lyophilized microparticles can additionally contain particles of reagents selected from the group consisting of: proteinase-k; proteinase-k and mutanolysin; and proteinase-k, mutanolysin, and an internal control DNA. The additional enzymes are often used in cell-specific lysis applications.

Conditions of DNA Binding and Elution

One factor to consider when assessing the efficacy of a DNA-capture material is the material's pKa. The pKa of an acid, HA, is an equilibrium constant for the equilibrium

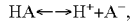

given by pKa=$-\log_{10}$ Ka, where Ka=[H$^+$] [A$^-$]/[HA]. It can be shown that, when the pH (=$-\log_{10}$ [H$^+$]) of the solution is numerically equal to the pKa of the acid, the acid is 50% dissociated at equilibrium. Therefore, knowing the pKa of a material gives an indication of the pH, below which it is largely dissociated (in anion form), and above which it is largely unionized.

The pKa for an amino group is defined for its conjugate base, as follows: a protonated amine, R—NH$_3^+$ is in dissociative equilibrium:

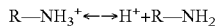

and its pKa is given by $-\log_{10}$ Ka, where Ka=[H$^+$] [R—NH$_2$]/[R—NH$_3^+$].

Because a nitrogen atom is trivalent, and due to the conditions of dendrimerization, each molecule of PAMAM (0) has a mixture of primary, tertiary amine groups. Therefore, PAMAM(0) molecules exhibit multiple pK's over a range of values roughly consonant with the range of pKa's spanned by primary, and tertiary aliphatic amines, whose pKa's typically lie in the range 10-11, as evidenced by, for example, Table 12.2 of *Organic Chemistry, 2$^{nd}$* Ed., Allinger, et al., Eds., Worth Publishers, Inc. (1976). However, according to information provided by the manufacturer of PAMAM (0), Dendritech of Midland, Mich., PAMAM is in fact likely to have pKa's in the range of 5.5 (for the tertiary amines in the interior of the molecule)-9.5 (for the primary amines on the surface of the PAMAM molecules). A journal article that references this data is Tomalia, et al., Angew. Chem. Int. Ed. Engl., 29, 138-175 (1990), at page 163, right-hand column.

PAMAM(0) is effective as a binder for DNA in the processes described herein at least in part because the amine groups of the PAMAM(0) have a pKa of between 5-9. Thus, at low pH it is typically positively charged—and may even carry multiple positive charges per molecule arising from protonations of the amine groups at pH's lower than its pKa—and is therefore able to bind strongly to polynucleotides such as DNA and RNA, which typically comprise polyanions (are predominantly negatively charged) in solution.

During the use of the PAMAM(0) molecule in the processes described herein, the pH of the binding buffer (typically TRIS) used to lyse cells at the same time as binding liberated DNA to the particles, is approximately 7-8. At this pH, all the amines (6 possible groups per PEI molecule, as available from Sigma) remain protonated (positively charged) and hence strongly attract negative charged DNA molecules to bind towards the beads.

PAMAM(0) molecules are also advantageous because they are resistant to, e.g., are immune to, degradation by lytic enzymes, protease enzymes (e.g., mixtures of endo- and exo-proteases such as pronase that cleave peptide bonds), harsh chemicals such as detergents, and heat up to 95° C., and as such are able to bind RNA and DNA during the lysis process as well. Thus, cell lysis and RNA and/or DNA binding can be combined into a single (synchronous) step, thereby both saving time and at least one processing step. The strong binding of RNA and/or DNA molecules to PAMAM(0) enables rapid washing of affinity beads coated in PAMAM(0) to remove PCR inhibitors using a wash solution. The release of RNA and/or DNA from the affinity beads is effected by an elevation of temperature in the presence of a proprietary release reagent. As the quantity of beads used is very small (<1 µl), the RNA and/or DNA can be released in a final volume as low as 3 microliters. The released RNA and/or DNA is neutralized to a final volume of 5-50 microliters using a neutralization reagent and is now ready for downstream PCR.

Typically, the amount of sample introduced is about 500 microliters or less (e.g., about 250 microliters or less, about 100 microliters or less, about 50 microliters or less, about 25 microliters or less, about 10 microliters or less). In some embodiments, the amount of sample is about 2 microliters or less (e.g., about 0.5 microliters or less).

PAMAM(0) gives excellent RNA and DNA recovery, based in part on its high binding capacity, and its high release efficiency. In general, the ratio of mass of particles to the mass of RNA or DNA retained by the particles is no more than about 25 or more (e.g., no more than about 20, no more than about 10). For example, in some embodiments, about 1 gram of particles retains about 100 milligrams of RNA or DNA; when used in smaller quantities, similar ratios can be obtained (e.g., a binding capacity of 100 µg of RNA or DNA/mg beads).

Other Apparatus for DNA Capture

In other embodiments, the solid support can be configured as a retention member (e.g., porous member such as a column, filter, a porous membrane, a microporous filter, or a gel matrix, having multiple openings such as pores and/or channels, through which RNA and/or DNA passes) through which sample material (containing the RNA and/or DNA) must pass. Such a retention member may be formed of multiple surface-modified particles constrained into a suitable geometry. In some embodiments, the retention member comprises one or more filter membranes available from, for example, Osmonics, which are formed of polymers that may also be surface-modified and used to retain RNA and/or DNA. In some embodiments, a retention member is configured as a plurality of surfaces (e.g., walls or baffles) across which a sample passes. The walls or baffles are modified to retain RNA and/or DNA in preference to, e.g., PCR inhibitors. Such a retention member is typically used when the microparticles are non-magnetic.

As a sample solution moves through a processing region containing such a retention member (suitably modified to preferentially retain RNA and/or DNA), RNA and/or DNA is retained while the liquid and other solution components (e.g., inhibitors) are less retained (e.g., not retained) and exit the processing region. Typically, such a retention member retains at least about 50% of RNA and/or DNA molecules (at least about 75%, at least about 85%, at least about 90%) of the RNA and/or DNA molecules present in the sample that entered the processing region. The processing region is typically at a temperature of about 50° C. or less (e.g., 30° C. or less) during introduction of the sample. Processing can continue by washing the retention member with a wash solution to separate remaining inhibitors from RNA and/or DNA retained by the retention member.

In some embodiments, the sample preparation processes described herein are performed within a microfluidic device, such as a microfluidic cartridge configured to receive a sample, and to capture RNA and/or DNA molecules from the sample on a solid support contained within it. Exemplary microfluidic cartridges are described in U.S. Patent Application Publication No. 2006/0166233, and WO2008/ 061165, both of which are incorporated herein by reference. Such cartridges may include one or more actuators configured to move microdroplets of various liquid solutions within the cartridge, a chamber configured to lyse cells in the sample, and one or more channels and associated valves configured to direct, disrupt, and divert liquid flow within the cartridge.

While sample preparation has been described as being a sequence of operations carried out in a single location, such as in a process tube or a microfluidic cartridge, other configurations can be used. For example, in some embodiments, the retention member carrying a polynucleotide-affinity material can be removed from a region where DNA and/or RNA capture occurs, for subsequent processing elsewhere. For example, the retention member may be contacted with a mixture comprising DNA and/or RNA and inhibitors in one location, and then moved to another location at which the RNA and/or DNA are removed from the retention member.

Other Advantages of the DNA Capture Material Described Herein

The extraction reagents and sample preparation processes described herein offer superior performances compared to currently available off-the-shelf kits for sample preparation. Advantages of the materials and methods herein include the following.

A streamlined sample preparation procedure having fewer steps (as few as six from raw sample to purified RNA and/or DNA) and utilizing fewer containers than other procedures.

Extraction control (cellular, plasmid, or naked) DNA can also be included along with the affinity beads. An internal control DNA can be included with the lysis reagents so that the internal control DNA gets co-purified with the other DNA (such as the target DNA) present in the clinical sample, and gets eluted amongst the final released DNA. During amplification of the eluted DNA, the internal control DNA is also amplified, and can subsequently be detected using a separate fluorophore from the target DNA. This gives an extra confirmation that the sample prep process worked as required.

The description herein has included a characterization of properties and use of microparticles coated in PAMAM (Generation 0). It would be understood by one of ordinary skill in the art that other affinity molecules may suitably be used in the processes described herein, as described elsewhere (e.g., U.S. patent application publication 2006-0166233, incorporated herein by reference).

EXAMPLES

Example 1

Sample Preparation Process

The following six steps can be accomplished in as little as 20 minutes for a single sample, to 30 minutes for a batch of 12 samples, using a reagent kit as further described herein. The steps are also easily automated as in a system described in U.S. provisional patent application Ser. No. 60/959,437, filed Jul. 13, 2007, incorporated herein by reference. The steps are also shown, schematically, in FIG. 1, and described elsewhere herein.

One exemplary process is as follows.

1. Mix ~500 µl of the clinical sample with 500 µl of lysis buffer and magnetic affinity beads, surface-bound with PAMAM(0). Kits for detecting viruses such as EV13 include some lytic enzymes as well dissolved in the lysis buffer.

2. Incubate the mixture of sample, lysis buffer, and beads at a temperature between room temperature and 60° C. for 5-10 minutes, to lys the cells and bind the RNA and/or DNA to the affinity beads.

3. Separate the magnetic beads and remove as much of the supernatant solution as possible.

4. Wash the beads with a wash reagent.

5. Release the RNA and/or DNA from the beads by heating the beads for 3 minutes at 85° C. in the presence of as little as 3 microliters of release solution.

6. Remove the released RNA and/or DNA and neutralize the solution with a neutralization reagent, such as a Tris buffer, to create PCR-ready RNA and/or DNA.

Another exemplary process is as follows.

Sample: Mix 500 µl Plasma w 500 µl Prep Buffer, or Dip Swab in 1 mL RNA Prep Buffer.

The mixture may optionally be pre-filtered.

Incubate @ 60° C. for 10 min.; clean up with proteolytic enzymes if necessary (swab only) and effect RNA and/or DNA capture by PAMAM(G0) coated affinity beads (magnetic) as further described herein.

Optionally, in a case where RNA is desired to be determined, apply DNAse treatment (such as with 7U DNase @ 37 deg C. for 10 min.) to the mixture.

Wash RNA bound beads with 100 µl Wash Reagent (2×) as further described herein.

Release RNA from beads with heat (85° C.; 3 min.) in the presence of Release Reagent, as further described herein, thereby liberating RT-PCR ready RNA.

Example 2

Application to a Wide Variety of Matrices

The procedures described herein work for a variety of sample matrices, including both clinical and non-clinical samples, as shown by the following non-exhaustive list:
Nasal swab
CSF
Nasal swab in M4
Nasal swab in UTM
Plasma Example 3

Representative Results

Figure 3:
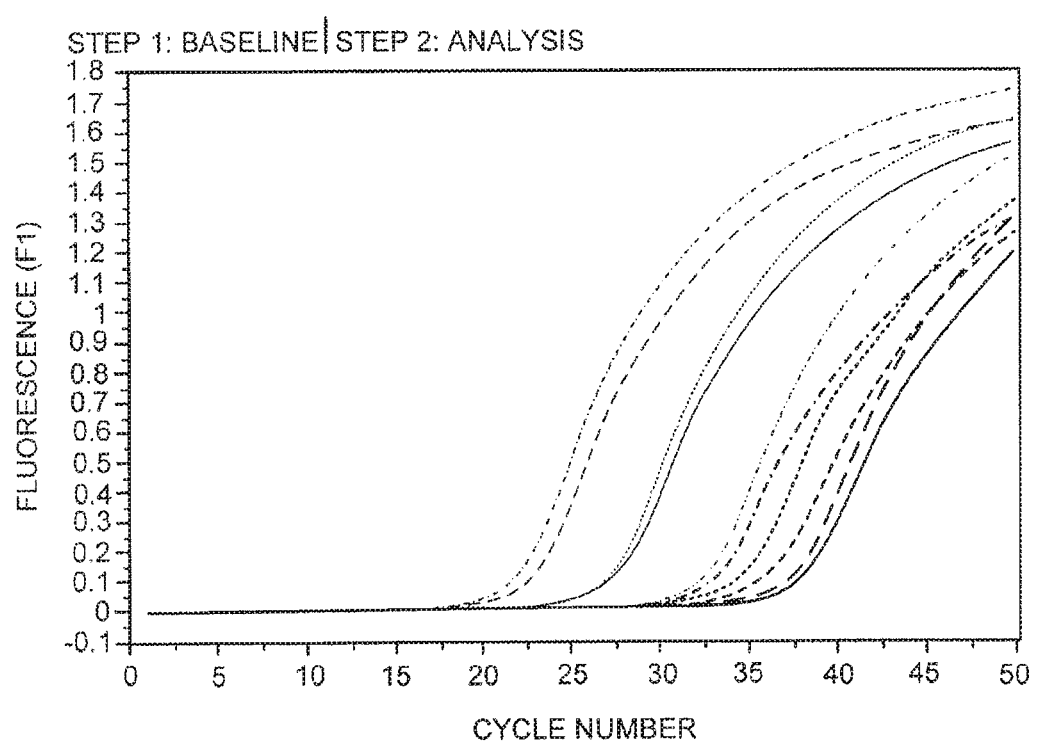
FIG. 3 shows PCR curves for EV13 RNA extraction from nasal swabs.

FIG. 3 shows the use of RNA extraction reagent, PAMAM (0), and a process as further described herein, to isolate and purify Enterovirus 13 (EV13) RNA from Nasal Swabs, using a lysis buffer as described elsewhere herein. The graph shows PCR curves for various samples spiked with each of $2 \times 10^4$, 2000, 200, 50, and 20 copies/1 mL of RNA Prep buffer. The RNA was released into 10 µl, but only 2 µl of released RNA was used for RT-PCR, which was performed using a Qiagen RT-PCR kit. PCR curves rise from the axis in order of decreasing concentration, from left to right.

Figure 4:
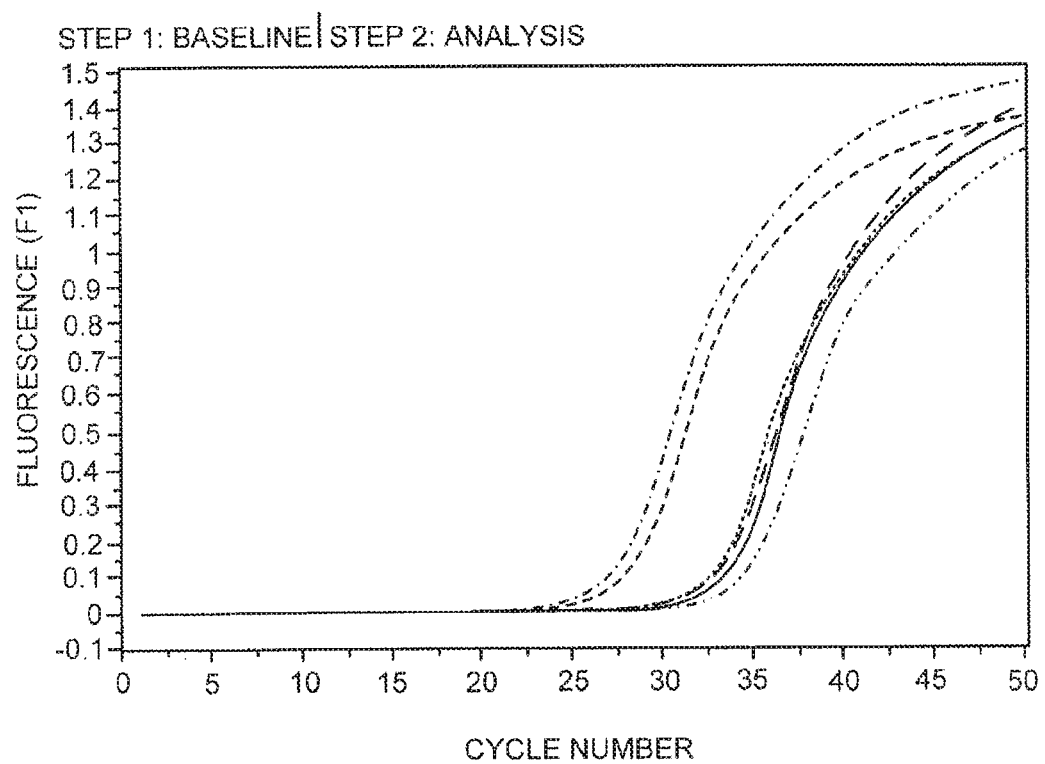
FIG. 4 shows PCR curves for EV13 RNA extraction in M4 media.

FIG. 4 shows the use of RNA extraction reagent, PAMAM (0), and a process as further described herein, to isolate and purify Enterovirus 13 (EV13) RNA from Nasal Swabs collected in M4 media. The graph shows PCR curves for various samples spiked with each of 1000, 100, and 50, copies/1 mL of sample. PCR curves rise from the axis in order of decreasing concentration, from left to right.

Figure 5:
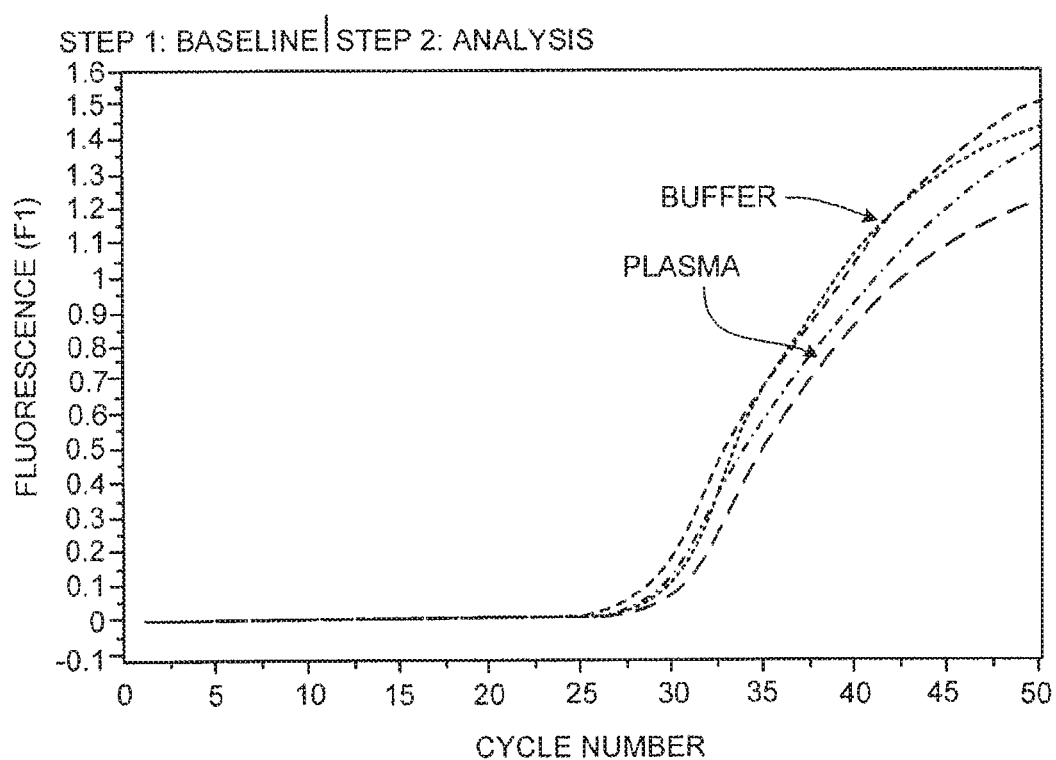
FIG. 5 shows a comparison of PCR curves from RNA extracted from a buffer to one obtained from plasma.

FIG. 5 shows a comparison of RNA extraction using PAMAM(0) beads between buffer samples and plasma. 500 copies of EV13 RNA per 1 mL were used in both buffer and plasma samples, according to a process as further described herein.

Figure 6:
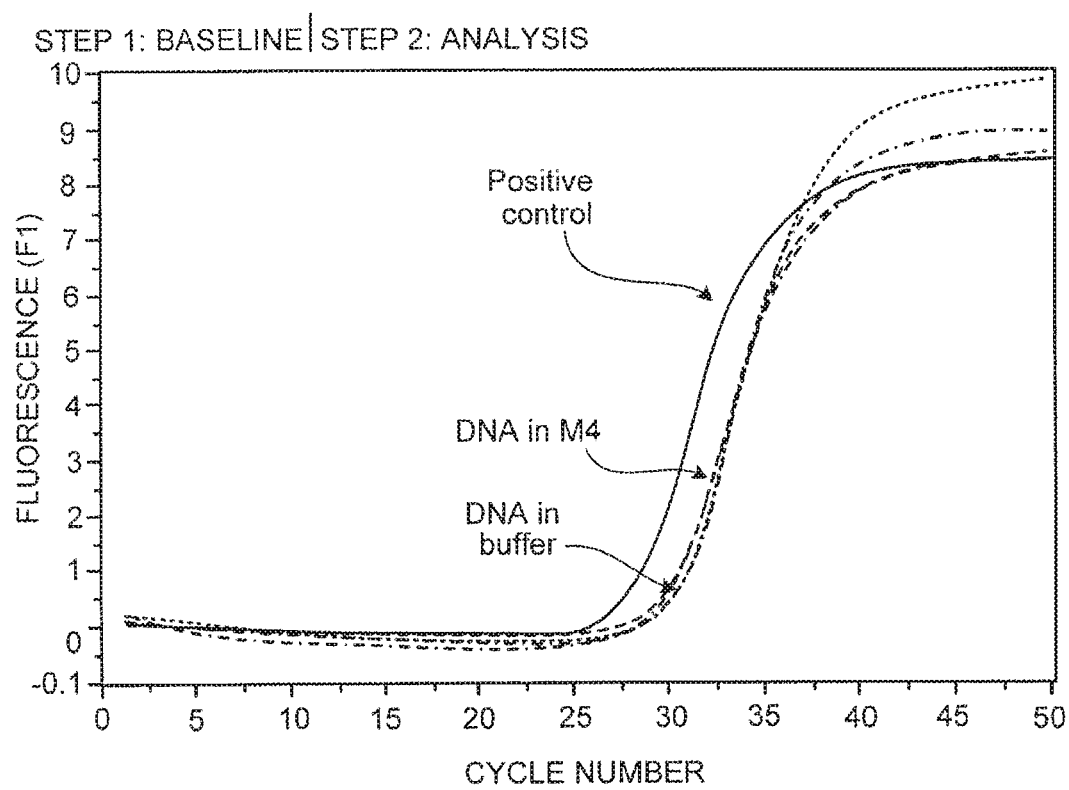
FIG. 6 shows RNA extraction using beads.

FIG. 6 shows extraction of DNA, using PAMAM(0) beads. 2.5 pg DNA spiked into an M4 buffer, or a lysis buffer as described herein, were extracted using a process for extracting RNA from an M4 collection buffer as further described herein.

Figure 7:
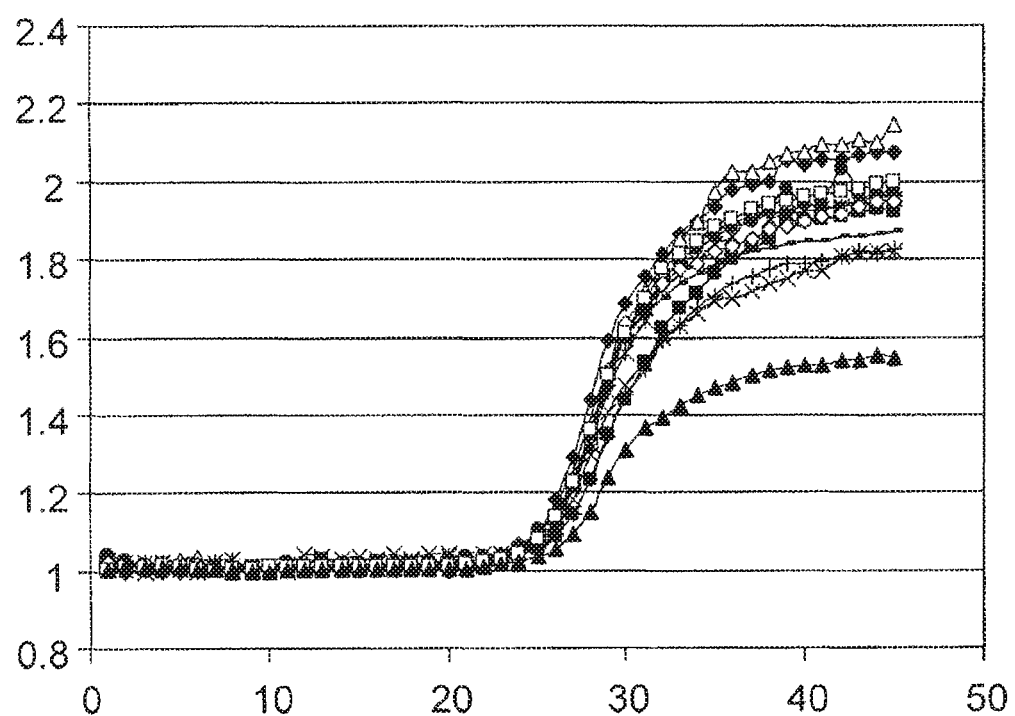
FIG. 7 shows RNA extraction from plasma.

FIG. 7 shows PCR curves for RNA extraction from a 500 µl plasma sample containing 200 copies EV13 RNA, using 7U DNAse treatment.

Figure 8:
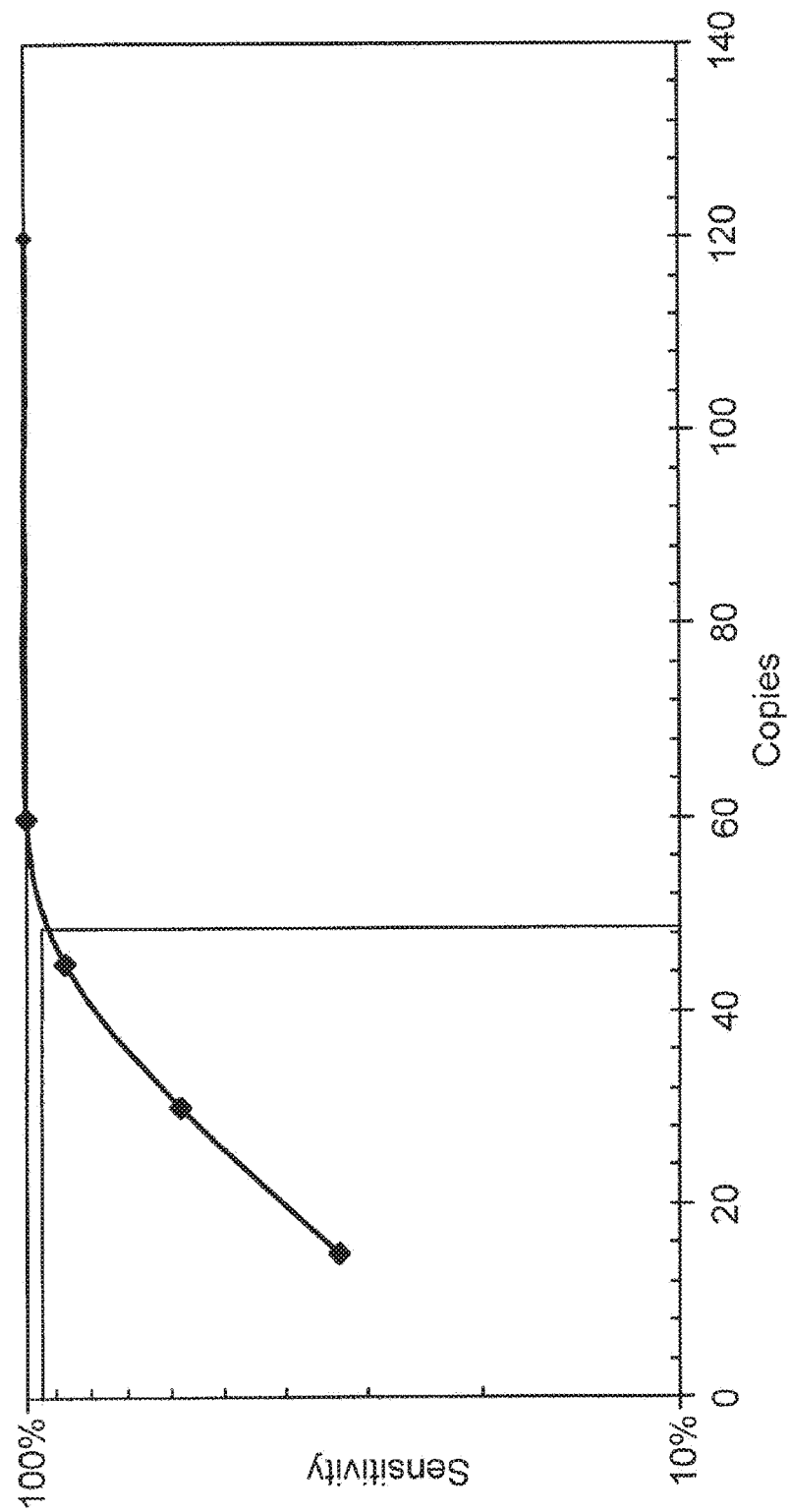
FIG. 8 illustrates extraction sensitivity.

FIG. 8 shows illustrates the sensitivity of the process. Process analysis reveals an LoD of 50 copies/200 µl CSF.

Example 4

Exemplary Protocol for the Extraction of RNA from M4, Dry Swab in 1× TCEP Buffer, THB Samples Sample Preparation Pre-Processing (Only Swab Samples Require Filtration)

| Step | Action |
|---|---|
| 1 | Pipette 500 µL of specimen into a tube (1.7 ml DOT snap cap tube) containing 500 µL of TCEP buffer |
| 2 | Pipette up and down 2x, and then pipette entire amount into 3 ml syringe |
| 3 | Insert plunger into syringe, and filter contents into a clean tube (1.7 ml DOT snap cap tube), applying pressure until all liquid is expelled, and foam starts to come out of filter (avoid getting foam into sample). |

RNA Extraction and PCR Prep

| Step | Action |
|---|---|
| 1 | Pipette sample (500 µL of specimen, plus 500 µL TCEP buffer) into a 1.7 ml DOT snap cap tube containing 30 µL of RNA magnetic beads. Cap and invert Reaction Tube 5 times, or until beads are dispersed (or dissolved, in the case of lyophilized beads). |
| 2 | Immediately place samples in a 60° C. water bath, and incubate for 10 min (10.5 min maximum). |
| 3 | Remove samples from water bath, and dry outsides of tubes with a Absorbent wipe. |
| 4 | Place tubes on magnetic rack, and allow separation to proceed for 1 minute (1.5 min max). |
| 5 | Using a fresh pipette for each sample, carefully aspirate 1 ml of supernatant from each sample (without disturbing beads), using a 1 ml pipettor. Discard supernatant. Be sure to remove any liquid that remains in the tube cap. |
| 6 | After initial removal of supernatants from all samples, remove any remaining liquid using a fresh 1 ml pipette tip for each sample. |

| Step | Action |
|---|---|
| 7 | Place tubes in a non-magnetic tube rack, and add 100 μL of Wash Buffer (0.1 mM Tris, pH 7.5) to each tube using a 200 ul pipette tip. Pipette up and down 10 times, or until all magnetic beads are resuspended, and no beads remain stuck to pipette tip. |
| 8 | Place tubes on magnetic rack for 30 seconds, allowing beads to separate. |
| 9 | Carefully aspirate supernatant from all samples using a 200 ul pipette tip. Discard Supernatant. Using a fresh 20 μl tip for each sample, aspirate any remaining liquid left in the sample (ie-liquid that has "settled" following the first aspiration step), and discard the liquid. |
| 10 | Place tubes in a non-magnetic tube rack, and add 10 μL of Release Buffer (20 mM Bis- Tris Propane or 20 mM Tris pH 9). Vortex for 10 seconds, or until beads are resuspended. |
| 11 | Place samples in a heat block at 85° C. for 3 minutes (3.5 min max). Remove samples from heat block, and place on magnetic rack for 30 seconds (1 min max). |
| 12 | Remove samples from heat block, and place on magnetic rack for 30 seconds (1 min max). |
| 13 | Keeping tubes on the magnetic rack, remove all liquid, carefully avoiding magnetic beads on side of tube, and place in 0.65 ml DOT tube. |
| 14 | Mix sample by pipetting up and down once. Sample is now ready for PCR. |
| 15 | Make PCR mix using Quantitect kit spiked with 0.6 uM primers and extra platinum taq. |
| 16 | Add 8 uL of mix into Rotorgene or LC capillaries, add 2 μL of RNA. |
| 17 | Run RT PCR program as follows: 50 degrees for 20 min (RT step), 95 degrees for 5 min (denaturation), cycling at 95-2 sec, 58-50 sec (50 cycles). |

Example 5

Exemplary Protocol for the Extraction of RNA from Plasma Samples RNA Extraction and PCR Prep

| Step | Action |
|---|---|
| 1 | Pipette sample (500 ul of specimen, plus 500 ul TCEP buffer + 70 uL 10% SDS) into a 1.7 ml DOT snap cap tube containing 30 ul of RNA magnetic beads. Cap and invert Reaction Tube 5 times, or until beads are dispersed (or dissolved, in the case of lyophilized beads). |
| 2 | Immediately place samples in a 60° C. water bath, and incubate for 10 min (10.5 min maximum). |
| 3 | Remove samples from water bath, and dry outsides of tubes with a Absorbent wipe. |
| 4 | Place tubes on magnetic rack, and allow separation to proceed for 1 minute (1.5 min max). |
| 5 | Using a fresh pipette for each sample, carefully aspirate 1 ml of supernatant from each sample (without disturbing beads), using a 1 ml pipettor. Discard supernatant. Be sure to remove any liquid that remains in the tube cap. |
| 6 | After initial removal of supernatants from all samples, remove any remaining liquid using a fresh 1 ml pipette tip for each sample. |
| 7 | Add 250 uL DNAse buffer with 1 Dnase pellet or 5 units of liquid DNAse. Resuspend beads by vortexing or pipetting. |
| 8 | Incubate at 37 for 10 min. |
| 9 | Place tubes on magnetic rack, and allow separation to proceed for 1 minute (1.5 min max). |
| 10 | Using a fresh pipette for each sample, carefully aspirate 1 ml of supernatant from each sample (without disturbing beads), using a 1 ml pipettor. Discard supernatant. Be sure to remove any liquid that remains in the tube cap. |
| 11 | Place tubes in a non-magnetic tube rack, and add 100 μl of Wash Buffer (0.1 mM Tris, pH 7.5) to each tube using a 200 ul pipette tip. Pipette up and down 10 times, or until all magnetic beads are resuspended, and no beads remain stuck to pipette tip. |
| 12 | Place tubes on magnetic rack for 30 seconds, allowing beads to separate. |
| 13 | Carefully aspirate supernatant from all samples using a 200 ul pipette tip. Discard Supernatant. Using a fresh 20 ul tip for each sample, aspirate any remaining liquid left in the sample (ie-liquid that has "settled" following the first aspiration step), and discard the liquid. |
| 14 | Place tubes in a non-magnetic tube rack, and add 10 μL of Release Buffer (20 mM Bis- Tris Propane or 20 mM Tris pH 9). Vortex for 10 seconds, or until beads are resuspended. |

| Step | Action |
|------|--------|
| 15 | Place samples in a heat block at 85° C. for 3 minutes (3.5 min max). |
| 16 | Remove samples from heat block, and place on magnetic rack for 30 seconds (1 min max). |
| 17 | Keeping tubes on the magnetic rack, remove all liquid, carefully avoiding magnetic beads on side of tube, and place in 0.65 ml DOT tube. |
| 18 | Mix sample by pipetting up and down once. Sample is now ready for PCR. |
| 19 | Make PCR mix using Quantitect kit spiked with 0.6 uM primers and extra platinum taq. |
| 20 | Add 8 uL of mix into Rotorgene or LC capillaries, add 2 uL of RNA. |
| 21 | Run RT PCR program as follows: 50 degrees for 20 min (RT step), 95 degrees for 5 min (denaturation), cycling at 95-2 sec, 58-50 sec (50 cycles). |

Example 6

Assembly Process for 2×TCEP Buffer for RNA Extractions

The procedure in this example provides a method appropriate for preparing up to 50 mL of a 2×TCEP Buffer (20 mM Tris HCl pH 7.0, 2% Tx-100, 10 mM TCEP) used in RNA extractions, as further described herein. The following is a list of reagents utilized in the process.

1 M Tris-HCl pH 7.0
100% Triton X-100 (Tx-100')
TCEP (Tris(2-carboxyethyl)phosphine hydrochloride)
Ultrapure Water The following is a list of equipment utilized in the process.

Laminar flow hood
Serological pipette filler
Serological pipette
Vortexer
Appropriate size container
New, sterile graduated cylinder
Appropriate Personal Protective Equipment (PPE)
Product Label An operator performing this procedure must know how to prepare buffers, and possess an excellent pipetting technique, and should exercise general lab sterile techniques, prepare the solution in a laminar flow hood for sterility, and be cautious to not contaminate stock reagents. Gloves and lab coat should be worn by operator at all times.

Preparation of 50 mL of the 2× TCEP Buffer (20 mM Tris HCl pH 7.0, 2% Tx-100, 10 mM TCEP)

| Step | Action | For 50 mls |
|------|--------|------------|
| 1 | Verify reagent availability and expiration. Also perform a visual inspection of stock reagents. | |
| 2 | Affix the product label to the appropriate container. | |
| 3 | Using a serological pipette or a new graduated cylinder dispense ultrapure water into the container. | 45 mL H20 |
| 4 | Using a serological pipette or a new graduated cylinder, 1 mL Tris-HCl dispense 1M Tris-HCl pH 7.0 into container. | 1M Tris-HCl |
| 5 | Weigh out appropriate amount of TCEP and add to container. | 143 mg |
| 6 | Vortex/shake well to mix. Do not add Triton until the TCEP has completely dissolved. | |
| 7 | Using a serological pipette, add Triton X-100 to container being careful to get all of solution out of pipette. | 4 mL |
| 8 | Vortex/shake well to mix. | |
| 9 | Store at room temperature. | |

Example 7

Exemplary Process for the Preparation of Magnetic RNA Affinity Microspheres

Figure 9:
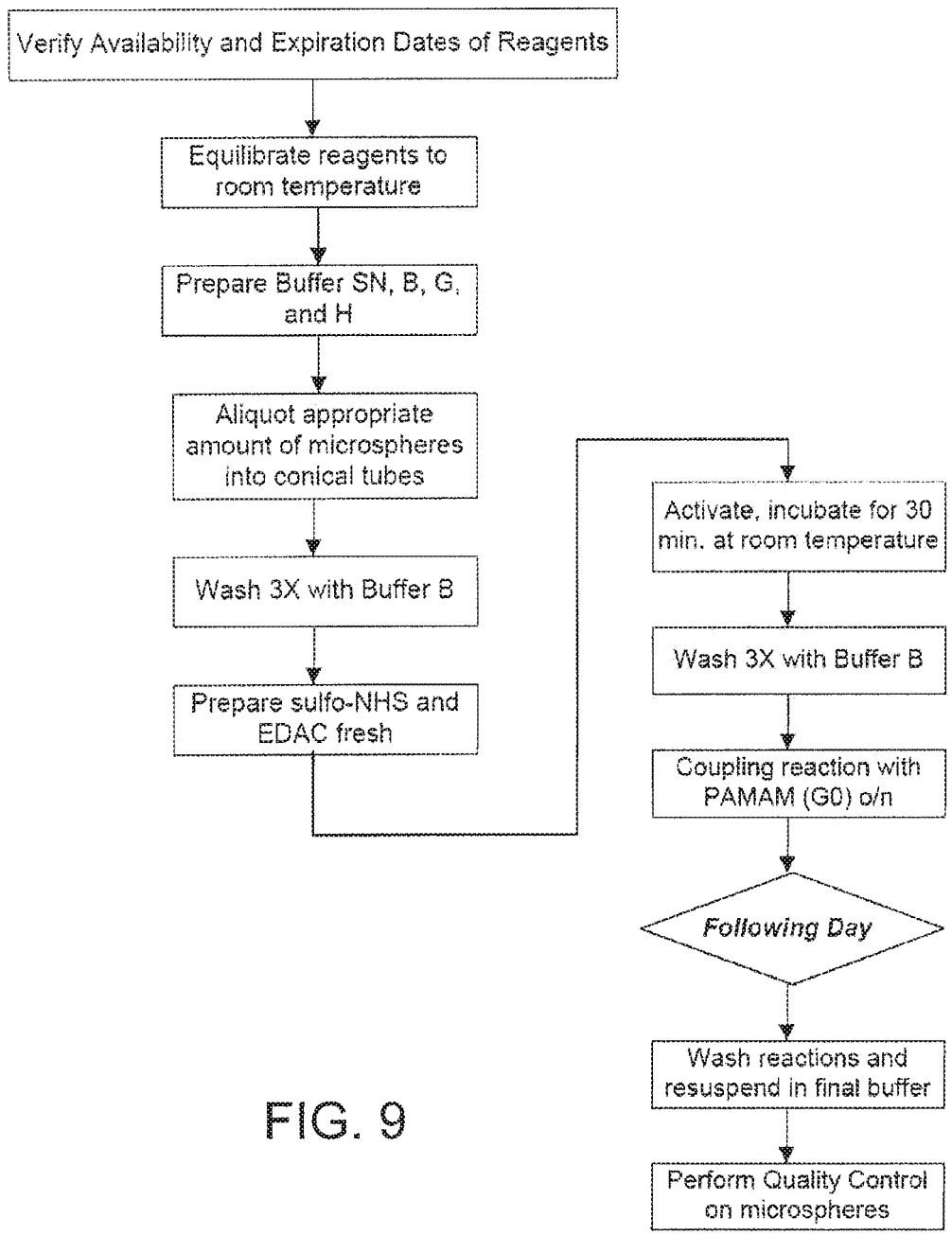
FIG. 9 shows a flow-chart for a process of making PAMAM(Generation 0) coated microparticles.

This procedure provides an appropriate method for one batch of PAMAM(G0) coated magnetic microspheres, commonly referred to as Magnetic RNA-Affinity Microspheres. One batch consists of 1-10 ml synthesis resulting in 6 mL of magnetic RNA affinity microspheres. A flow-chart of the process is shown in FIG. 9. The following is a list of equipment utilized in the process.

Vortexer
Microcentrifuge
Magnetic Rack
1.7 mL microcentrifuge tubes
4-oz specimen containers
50 mL conical tubes
15 mL conical tubes
Centrifuge
pH meter
Pipettors
Pipettor tips
Ultrasonic dismembrator
dH20 wash bottle
Task Wipers
Balance
Laboratory marker
Gloves and Labcoat
Orbital shaker
Labeling tape
Pipette filler
Serological pipettes An operator performing this procedure must be competent with a microbalance, pipettors, pH meter, ultrasonic dimembrator and a microcentrifuge, and must know how to prepare buffers and possess an excellent pipetting technique. Gloves, labcoat, and eye protection should be worn by the operator at all times. Ear protection must be worn during sonication steps. All solutions are prepared in a laminar flow hood.

Procedure—Preparation of Buffers

| Step | Action |
|---|---|
| 1 | Verify availability and check expiration dates of all solutions and reagents. |
| 2 | Visually inspect all stock solutions and reagents for precipitation or color change. Do not use if precipitation occurs or color changes. |
| 3 | Equilibrate all aliquoted stock solutions and reagents to RT. Take out EDAC and NHS from −20° C. and equilibrate to RT before use, this should take approximately one hour. |

Preparation of 70 mL Buffer SN—B (50 mM MES Buffer pH 6.1, 0.15% Triton X-100)

| Step | Action | For 70 mls |
|---|---|---|
| 1 | Label a 4-oz or 500 ml container with "Buffer SN-B", date, and initials. | |
| 2 | Using a serological pipette Buffer SN-C to bottle. | 7 mL |
| 3 | With a P5000, 10% Triton X-100 to bottle. | 420 uL |
| 4 | Using a graduated cylinder, add ultrapure water to bottle. | 62.5 mL |
| 5 | Mix well by inversion. | |
| 6 | Check pH of solution, which should be between 5.8-6.5. | |
| 7 | Store at 4° C. during overnight incubation but discard after lot manufacture is complete. | |

Preparation of 50 mL Buffer SN—G (50 mM Tris pH 7.5, 0.1% Triton X-100)

| Step | Action | For 50 mls |
|---|---|---|
| 1 | Labe a 50 mL conical tube with "Buffer SN-G", date, and initials | |
| 2 | Using a serological pipette add 1M Tris pH 7.5 to bottle | 2.5 mL |
| 3 | With a P5000, 10% Triton X-100 to bottle. | 200 uL |
| 4 | Using a graduated cylinder, add ultrapure water to bottle. | 47.3 mL |
| 5 | Mix well by inversion. | |
| 6 | Chek pH of solution, which should be between 7.2-7.7 | |
| 7 | Store at RT for the duration of lot manufacture but discard after lot manufacture is complete. | |

Preparation of 10 mL Buffer SN—H (50 mM MES pH 6.1, no Tx)

| Step | Action | For 10 mls |
|---|---|---|
| 1 | Label a 15 mL conical tube with "Buffer SN-H", date, and initials. | |
| 2 | Using a serological pipette add Buffer C to bottle | 1 mL |
| 3 | Using a graduated cylinder, add ultrapure water to bottle. | 9 mL |
| 4 | Mix well by inversion. | |
| 5 | Check pH of solution, which should be between 5.8-6.5 | |
| 6 | Store at RT for the duration of lot manufacture but discard after lot manufacture is complete. | |

Steps to be performed on Day 1, include the following.

| Step | Action |
|---|---|
| 1 | Calculate required amount of carboxylated microspheres. Divide 10 mL by % solids to calculate amount of microspheres needed per reaction. 5 reactions per set. Multiply this number by 5 to get the total amount of microspheres for the full set. |
| 2 | Vortex the vial containing the microspheres very well (for approx 1 minute). |
| 3 | Label 1-50 mL conical tubes with Lot number, date, and initials. |
| 4 | Pipette the appropriate amount of microspheres into 50 mL conical tube. |
| 5 | Place conical tubes onto magnetic rack and let sit until beads are fully captured by magnet. Remove supernatant carefully. |

| MES buffer wash | | For 30 mls |
|---|---|---|
| 6 | Add Buffer SN-B to each tube and vortex to mix | 10 mls |
| | Place conical tubes onto magnetic rack and let sit until beads are fully captured by magnet. | |
| | Remove supernatant carefully. Repeat wash 2 more times. | |
| Prepare sulfo-NHS | | |
| 7 | Weigh out small amount of sulfo-NHS on weigh paper and multiply weight (in mg) by 20 to calculate μL of ultrapure water to add to make 50 mg/ml solution. Need 1.5 mL for 1 reactions (75 mg). Add to 1.7 mL tube and mix well. Weight (mg) × 20 = μL ultrapure water needed. Add ultrapure water and vortex well to resuspend. NHS solution should be prepared right before use, discard after 15 min. | |
| For 30 mls Activation (Prepare EDAC in hood) | | |
| 8 | Add reagents in the following order to each conical tube: | For 30 mls |
| | (i) ddH$_2$O | 5000 μL |
| | (ii) Buffer SN-C | 1000 μL |
| | (iii) 50 mg/mL sulfo-NHS | 1500 μL |

| | | |
|---|---|---|
| | Sonicate using ultrasonic dismembrator at a power output of 12 for the appropriate time making sure that the probe is submerged at all time. Clean probe with dH$_2$O and wipe with absorbent wipe before and after sonication. | 10 seconds |
| 9 | Immediately prepare 5 mg/ml EDAC in hood. EDAC solution should be prepared right before use, discard after 15 min. Weigh out small amount of EDAC onto weigh paper and multiply weight (in mg) by 200 to calculate μL of ultrapure water needed to make 5 mg/ml solution.<br>Need 2480 μl total (12.4 mg).<br>Prepare in 50 mL conical tube.<br>Weight (mg) × 200 = (μL) ultrapure water to add.<br>Vortex well after addition of ultrapure H2O. | |
| 10 | Add the following:<br>(i) 10% Triton X-100 10 μL<br>(ii) 5 mg/mL EDAC (add EDAC solution carefully; drop by drop 2480 μL while vortexing the solution at very low speed)<br>(iii) 50 mg/mL sulfo-NHS<br>Mix well by vortexing. | 10 μL<br>2480 μL<br><br><br>1500 μL |
| 11 | Record number of times EDAC opened on bottle. Discard after 5 uses. | |
| 12 | Secure tubes to orbital shaker with labeling tape and incubate at room temperature at setting 6 (or at setting where microspheres are mixing well). | 30 mins. |
| 13 | After incubation, centrifuge for 5 min at maximum speed and then place on magnet. Remove supernatant carefully but completely. | 5 mins. |
| MES buffer wash | | For 30 mls |
| 14 | Add Buffer SN-B to each tube and vortex to mix<br>Place conical tubes onto magnetic rack and let sit until beads are fully captured by magnet. Remove supernatant carefully.<br>Repeat wash 2 more times. | 10 mls |
| Coupling | | |
| 15 | Prepare coupling reaction:<br>(i) Add Buffer H<br>Sonicate using ultrasonic dismembrator at power output 9 for the appropriate time making sure that the probe is submerged. Clean probe with dH$_2$O and wipe with absorbent wipe before and after sonication.<br>(ii) Add PAMAM(G0) (add solution carefully, drop by drop while vortexing the solution on low speed).<br>(iii) Mix by vortexing | For 10 mls<br>6 mL<br>10 sec<br><br><br><br>250 μL |
| 16 | Secure tube to orbital shaker with labeling tape. Incubate overnight at a setting of 6 at room temperature (or at setting where microspheres are mixing well). | |
| 17 | Store buffers SN-B, H and G at 4° C. overnight.<br>Return NHS and EDAC stocks to −20° C. Return buffer SN-C to 4° C. | |

Steps to be performed on Day 2, include the following.

| Step | Action | |
|---|---|---|
| 18 | After overnight incubation, remove buffers SN-B and G from 4° C. and equilibrate to RT (approximately 1 hr). | |
| 19 | Centrifuge tubes for 5 min at maximum speed and place on magnetic rack. Remove supernatant carefully but completely. | |
| Tri Washes | | For 30 mls |
| 20 | Add Buffer SN G to each tube and vortex to mix. Clean probe with dH20 and wipe with absorbent wipe before and after sonication.<br>Place conical tubes onto magnetic rack and let sit until beads are fully captured by magnet. Remove supernatant carefully.<br>Repeat wash 2 more times. | 10 mL |
| Final Resuspension | | |
| 21 | Resuspend each reaction in Buffer SN-B by sonication using ultrasonic dismembrator at power output of 12 for 10 seconds (ensure that probe is submerged). Clean probe with dH2O and wipe with absorbent wipe before and after sonication. | 6 mL |
| 22 | Affix appropriate label to tube. | |
| 23 | Discard all buffers. Store Buffer SN-C at 4° C. | |
| 25 | Store at 4° C. Stable for 1 month if stored appropriately. | |

The foregoing description is intended to illustrate various aspects of the instant technology. It is not intended that the examples presented herein limit the scope of the appended claims. The invention now being fully described, it will be apparent to one of ordinary skill in the art that many changes and modifications can be made thereto without departing from the spirit or scope of the appended claims.

What is claimed is:

1. A system comprising:
   a container comprising:
      a plurality of magnetic beads coated with polycationic polyamine dendrimers, the polycationic polyamine dendrimers being covalently bonded to carboxyl groups on the plurality of magnetic beads, and
      a lytic enzyme,
      wherein the container is configured to receive a biological sample containing polynucleotides and allow the biological sample to come in contact with the plurality of magnetic beads, and
      wherein the plurality of magnetic beads in the container are configured to reversibly bind polynucleotides of the biological sample, through ionic bonding with the polycationic polyamine dendrimers, thereby producing a set of polynucleotide-retained beads;
   a release solution, wherein the set of polynucleotide-retained beads are configured to release the polynucleotides when contacted with the release solution and heated;
   a multi-lane microfluidic cartridge comprising:
      a plurality of separate microfluidic networks, wherein at least two of the separate microfluidic networks comprise:
         an opening for receiving polynucleotides released from the set of polynucleotide-retained beads into the microfluidic network;
         an amplification reaction chamber; and
         one or more channels leading from the opening to the amplification reaction chamber; and
      a heater located external to the multi-lane microfluidic cartridge and configured to be in thermal communication with the amplification reaction chamber.

2. The system of claim 1, wherein the polycationic polyamine dendrimers comprise six amine groups prior to covalently bonding to carboxyl groups on the magnetic beads.

3. The system of claim 1, wherein the polycationic polyamine dendrimers comprise at least four dendrimer branches having primary amine terminals prior to covalently bonding to carboxyl groups on the magnetic beads.

4. The system of claim 1, wherein the polycationic polyamine dendrimers comprise at least five amine groups when covalently bonded to carboxyl groups on the magnetic beads.

5. The system of claim 1, wherein the polycationic polyamine dendrimers comprise at least three dendrimer branches having primary amine terminals when covalently bonded to carboxyl groups on the magnetic beads.

6. The system of claim 1, wherein the polycationic polyamine dendrimers are amide-bonded to the magnetic beads.

7. The system of claim 1, wherein the polycationic polyamine dendrimers comprise polyamide dendrimers.

8. The system of claim 7, wherein the polyamide dendrimers comprise PAMAM dendrimers.

9. The system of claim 1, wherein the plurality of magnetic beads and the lytic enzyme are in solid form in the container prior to receiving the biological sample in the container.

10. The system of claim 1, wherein the plurality of magnetic beads and the lytic enzyme are in dry form in the container prior to receiving the biological sample in the container.

11. The system of claim 1, wherein the container further comprises sample process control polynucleotides prior to receiving the biological sample in the container.

12. The system of claim 9, wherein the lytic enzyme comprises proteinase K.

13. The system of claim 10, wherein the lytic enzyme comprises proteinase K.

14. The system of claim 1, wherein the polycationic polyamine dendrimers comprise an initial monomer core of ethylene diamine.

15. A kit comprising:
   a plurality of containers, at least one container comprising:
      a plurality of magnetic beads coated with polycationic polyamine dendrimers, the polycationic polyamine dendrimers being covalently bonded to the plurality of magnetic beads via amide bonds and comprising at least three dendrimer branches having primary amine terminals; and
      a lytic enzyme,
      wherein the at least one container is configured to receive a biological sample containing polynucleotides and to allow the biological sample to come in contact with the plurality of magnetic beads,
      wherein the plurality of magnetic beads and the lytic enzyme are in dry form in the at least one container prior to receiving the biological sample in the at least one container,
      wherein the plurality of magnetic beads in the at least one container are configured to reversibly bind polynucleotides of the biological sample, thereby producing a set of polynucleotide-retained beads, and
      wherein the set of polynucleotide-retained beads are configured to release the polynucleotides when contacted with a release solution and heated.

16. The kit of claim 15, wherein the polycationic polyamine dendrimers comprise six amine groups prior to covalently bonding to the plurality of magnetic beads.

17. The kit of claim 15, wherein the polycationic polyamine dendrimers have a molecular weight of less than about 600 Da prior to covalently bonding to the plurality of magnetic beads.

18. The kit of claim 15, wherein the polycationic polyamine dendrimers comprise at least four dendrimer branches having primary amine terminals prior to covalently bonding to the plurality of magnetic beads.

19. The kit of claim 15, wherein the polycationic polyamine dendrimers comprise at least five amine groups when covalently bonded to the plurality of magnetic beads.

20. The kit of claim 15, wherein the at least one container further comprises sample process control polynucleotides in dry form prior to receiving the biological sample in the at least one container.

21. The kit of claim 15, wherein the lytic enzyme comprises proteinase K.

22. The kit of claim 15, wherein the polycationic polyamine dendrimers comprise an initial monomer core of ethylene diamine.

23. The kit of claim 15, wherein the plurality of magnetic beads are configured to release the polynucleotides at an extraction efficiency of at least 90%.

* * * * *